US012059444B2

(12) United States Patent
Coffin

(10) Patent No.: US 12,059,444 B2
(45) Date of Patent: *Aug. 13, 2024

(54) ALTERED VIRUS

(71) Applicant: Replimune Limited, Oxfordshire (GB)

(72) Inventor: Robert Stuart Coffin, Oxfordshire (GB)

(73) Assignee: Replimune Limited (GB)

( * ) Notice: Subject to any disclaimer, the term of this patent is extended or adjusted under 35 U.S.C. 154(b) by 300 days.

This patent is subject to a terminal disclaimer.

(21) Appl. No.: 16/466,612

(22) PCT Filed: Jan. 9, 2018

(86) PCT No.: PCT/GB2018/050048
§ 371 (c)(1),
(2) Date: Jun. 4, 2019

(87) PCT Pub. No.: WO2018/127713
PCT Pub. Date: Jul. 12, 2018

(65) Prior Publication Data
US 2019/0343903 A1 Nov. 14, 2019

(30) Foreign Application Priority Data
Jan. 9, 2017 (GB) .................................. 1700350

(51) Int. Cl.
*A61K 35/768* (2015.01)
*A61K 35/763* (2015.01)
*A61K 45/06* (2006.01)
*A61P 35/00* (2006.01)
*C07K 16/28* (2006.01)

(52) U.S. Cl.
CPC .......... *A61K 35/768* (2013.01); *A61K 35/763* (2013.01); *A61P 35/00* (2018.01); *C07K 16/2818* (2013.01); *A61K 45/06* (2013.01)

(58) Field of Classification Search
CPC .... A61K 35/768; A61K 35/763; A61K 45/06; A61K 35/765; A61K 35/761; A61K 35/766; A61K 2039/505; A61K 2039/507; A61K 2039/5256; A61P 35/00; C07K 16/2818; C07K 2317/622; C12N 2710/16632; C12N 2710/16643; C12N 7/00; C12N 15/86
See application file for complete search history.

(56) References Cited

U.S. PATENT DOCUMENTS

| | | | |
|---|---|---|---|
| 5,122,458 A | 6/1992 | Post et al. | |
| 5,168,062 A | 12/1992 | Stinski | |
| 5,288,641 A | 2/1994 | Roizman | |
| 5,328,688 A | 7/1994 | Roizman | |
| 5,385,839 A | 1/1995 | Stinski | |
| 5,599,691 A | 2/1997 | Roizman | |
| 5,602,007 A | 2/1997 | Dunn et al. | |
| 5,698,531 A | 12/1997 | Nabel et al. | |
| 5,824,318 A | 10/1998 | Mohr et al. | |
| 5,846,707 A | 12/1998 | Roizman | |
| 6,040,169 A | 3/2000 | Brown et al. | |
| 6,071,692 A | 6/2000 | Roizman | |
| 6,120,773 A | 9/2000 | Roizman | |
| 6,172,047 B1 | 1/2001 | Roizman et al. | |
| 6,297,219 B1 | 10/2001 | Nabel et al. | |
| 6,340,673 B1 | 1/2002 | Roizman et al. | |
| 6,423,528 B1 | 7/2002 | Brown et al. | |
| 6,428,968 B1 | 8/2002 | Molnar-Kimber et al. | |
| 6,649,157 B2 | 11/2003 | Coffey et al. | |
| 6,770,274 B1 | 8/2004 | Martuza et al. | |
| 7,063,835 B2 | 6/2006 | Coffin | |
| 7,223,593 B2 | 5/2007 | Coffin | |
| 7,537,924 B2 | 5/2009 | Coffin | |
| 7,749,745 B2 | 7/2010 | Johnson et al. | |
| 7,981,669 B2 | 7/2011 | Coffin et al. | |
| 8,273,568 B2 | 9/2012 | Martuza et al. | |
| 8,277,818 B2 | 10/2012 | Coffin | |
| 8,361,978 B2 | 1/2013 | Rabkin et al. | |
| 8,470,577 B2 | 6/2013 | Johnson et al. | |
| 8,679,830 B2 | 3/2014 | Coffin et al. | |
| 8,680,068 B2 | 3/2014 | Coffin | |
| 8,703,120 B2 | 4/2014 | Martuza et al. | |
| 8,871,193 B2 | 10/2014 | Johnson et al. | |
| 8,986,672 B2 | 3/2015 | Zhang et al. | |
| 9,487,581 B2 | 11/2016 | Abate et al. | |
| 9,492,482 B2 | 11/2016 | Beech et al. | |
| 9,789,182 B2 * | 10/2017 | Graziano | A61K 39/3955 |
| 9,827,307 B2 | 11/2017 | Rabkin et al. | |

(Continued)

FOREIGN PATENT DOCUMENTS

| EP | 1235853 B1 | 7/2009 |
|---|---|---|
| JP | 2013511549 A | 4/2013 |

(Continued)

OTHER PUBLICATIONS

Du, et al Cancer Gene Therapy, vol. 21, No. 8 Jul. 18, 2014 (Year: 2014).*
Du, et al., Cancer Gene Therapy (2014) 21, 340-348 (Year: 2014).*
Simpson, et al., Cancer Res. 2006; 66: (9) May 1, 2006 (Year: 2006).*
Grandi, et al., Cancer Gene Therapy (2010) 17, 655-663 (Year: 2010).*
Schirrmann, et al., Antibody Engineering vol. 2 ® Springer-Verlag Berlin Heidelberg 2010; Chapter 30, p. 387-398 (Year: 2010).*
Shan, et al., Journal of Immunology, 1999, 162:6589-6595 (Year: 1999).*
Inouye et al., Protein Expression and Purification, 2015, 109:47-54 (Year: 2015).*
TakaraBio, 2000 URL: https://www.takarabio.com/documents/Vector%20Documents/PT3155-5.pdf; Accessed Apr. 20, 2022 (Year: 2000).*

(Continued)

*Primary Examiner* — Julie Wu
*Assistant Examiner* — Sydney Van Druff
(74) *Attorney, Agent, or Firm* — Norton Rose Fulbright LLP

(57) ABSTRACT

The present invention relates to an oncolytic virus encoding a CTLA-4 inhibitor, such as an anti-CTLA-4 antibody, or an antigen binding fragment thereof.

37 Claims, 13 Drawing Sheets

Specification includes a Sequence Listing.

(56) References Cited

U.S. PATENT DOCUMENTS

| | | | |
|---|---|---|---|
| 9,868,961 | B2 | 1/2018 | Allison et al. |
| 10,039,796 | B2 | 8/2018 | Zhang et al. |
| 10,287,252 | B2 | 5/2019 | Cowley et al. |
| 10,301,600 | B2 | 5/2019 | Coffin |
| 10,570,377 | B2* | 2/2020 | Coffin .................. C12N 7/00 |
| 10,612,005 | B2* | 4/2020 | Coffin ............. A61K 39/39558 |
| 10,626,377 | B2* | 4/2020 | Coffin ................ C07K 16/2818 |
| 10,765,710 | B2 | 9/2020 | Zitvogel et al. |
| 10,947,513 | B2* | 3/2021 | Coffin ................ C07K 16/2818 |
| 11,427,810 | B2* | 8/2022 | Coffin ................ C07K 16/2818 |
| 11,473,063 | B2* | 10/2022 | Coffin ................ A61K 39/3955 |
| 2003/0091537 | A1 | 5/2003 | Coffin |
| 2008/0014175 | A1 | 1/2008 | Hallahan et al. |
| 2010/0297072 | A1 | 11/2010 | DePinho |
| 2011/0044953 | A1 | 2/2011 | Allison et al. |
| 2013/0202639 | A1 | 8/2013 | Kousoulas et al. |
| 2014/0154216 | A1 | 6/2014 | Coffin |
| 2014/0271677 | A1 | 9/2014 | Palese et al. |
| 2015/0232812 | A1 | 8/2015 | Coffin |
| 2015/0283234 | A1 | 10/2015 | Graziano et al. |
| 2016/0040186 | A1* | 2/2016 | Liu .................. C12N 15/85 |
| | | | 435/69.1 |
| 2021/0252135 | A1* | 8/2021 | Coffin .................. C12N 7/00 |
| 2021/0254019 | A1* | 8/2021 | Coffin ................ C07K 16/2818 |

FOREIGN PATENT DOCUMENTS

| | | | |
|---|---|---|---|
| JP | 2015/508156 A | 3/2015 | |
| JP | 2016509045 A | 3/2016 | |
| WO | 97/12623 A1 | 4/1997 | |
| WO | WO-9830707 A2 * | 7/1998 | ............ A61P 25/16 |
| WO | 01/53505 | 7/2001 | |
| WO | 01/53505 A2 | 7/2001 | |
| WO | 01/53506 A2 | 7/2001 | |
| WO | 2005/011715 A1 | 2/2005 | |
| WO | 2006/002394 A2 | 1/2006 | |
| WO | 2006/048749 A1 | 5/2006 | |
| WO | 2007/052029 A1 | 5/2007 | |
| WO | 2007123737 A2 | 11/2007 | |
| WO | WO-2007123737 A2 * | 11/2007 | ......... C07K 16/2818 |
| WO | 2010042189 A2 | 4/2010 | |
| WO | 2011063309 A1 | 5/2011 | |
| WO | 2011/118866 A1 | 9/2011 | |
| WO | 2012/038606 A1 | 3/2012 | |
| WO | 2013/038066 A1 | 3/2013 | |
| WO | 2013112942 A1 | 8/2013 | |
| WO | 2014022138 A2 | 2/2014 | |
| WO | 2014/036412 A2 | 3/2014 | |
| WO | 2014066532 A1 | 5/2014 | |
| WO | 2014128235 A1 | 8/2014 | |
| WO | 2015032755 A1 | 3/2015 | |
| WO | 2015/059303 A1 | 4/2015 | |
| WO | 2015/077624 A1 | 5/2015 | |
| WO | 2015066042 A1 | 5/2015 | |
| WO | 2015/128313 A1 | 9/2015 | |
| WO | 2015/153417 A1 | 10/2015 | |
| WO | 2016008976 A1 | 1/2016 | |
| WO | WO-2016008976 A1 * | 1/2016 | ........... A61K 9/0019 |
| WO | 2016/118865 A1 | 7/2016 | |
| WO | 2017/118864 A1 | 7/2017 | |
| WO | 2017118866 A1 | 7/2017 | |
| WO | 2017118867 A1 | 7/2017 | |
| WO | WO-2017118865 A1 * | 7/2017 | ........... A61K 35/763 |
| WO | 2017/181420 A1 | 10/2017 | |
| WO | 2018127713 A1 | 7/2018 | |

OTHER PUBLICATIONS

Robinson, et al., Gene Therapy 2003 10:292-303 (Year: 2003).*
Bateman et al. Cancer Res. Mar. 15, 2000;60(6):1492-7.
Bateman et al. Cancer Res. Nov. 15, 2002;62(22):6566-78.
Haswell et al Eur J Immunol 2001 31 3094-3100.
Hetrologous Expression. In Binder, Hirokawa and Windorst (eds.)—Encyclopedia of Neuroscience. (2009) Springer, Berlin, Heidelberg Https://Doi.org/10.1007/978-3-540-29678-2_2190.
Hoffmann et al. World J Gastroenterol. Mar. 28, 2008 14(12):1842-1850.
Huang et al., Mol Ther, Feb. 2010, vol. 18, No. 2, pp. 264-274.
IGI Global "What is Heterologous Expression" retrieved from https://www.igiglobal.com/dictionary/heterologousexpression/49470.
Kanagavelu et al PlosOne 2014, 9, 2, e90100.
Kanagavelu et al Vaccine 2012 30 691-701.
Kasuya et al., Journal of Japan Surgical Society, 2006, 107, Extra Issue (2), p. 369, No. PS-005-8.
Kim et al Cancer Res 2009, 69, 21, 8516-8525.
Li et al. Int. J. Cancer 2008, 123: 493-499.
Nakano et al., Journal of Japan Surgical Society, 2001,102, Extra Issue, p. 82, No. SF4e-4.
Patentee's response to EPO communication dtd Sep. 25, 2009, EP No. 17701910.6.
Terada, K. et al: "Development of a rapid method to generate multiple oncolytic HSV vectors and their in vivo evaluation using syngeneic mouse tumor models", Gene Therapy, vol. 13, No. 8, Apr. 1, 2006 (Apr. 1, 2006), pp. 705-714, Nature Publishing Group, London, GB.
Yi et al Cancer Res 2007, 67 20 10027-10037.
Altschul, S F et al (1990) J Mol Biol 215:403-10.
Altschul, S.F. (1993) J Mol Evol 36:290-300.
Chou et al. (1990) Science 250: 1262-1266.
Devereux et al (1984) Nucleic Acids Research 12, p. 387-395.
Diefenbach et al., "Oncolytic virotherapy using herpes simplex virus: how far have we come?" Oncolytic Virotherapy, Nov. 1, 2015 (Nov. 1, 2015), p. 207.
Du et al. "Tumor-specific oncolytic adenoviruses expressing granulocyte macrophage colony-stimulating factor or anti-CTLA4 antibody for the treatment of cancers", Cancer Gene Therapy, vol. 21, No. 8, Jul. 18, 2014 (Jul. 18, 2014), pp. 340-348.
Gangi et al., "The safety of talimogene laherparepvec for the treatment of advanced melanoma", Expert Opinion on Drug Safety, Dec. 28, 2016 (Dec. 28, 2016), pp. 1-5.
Gibney et al., "Preliminary results from a phase A study of INCB024360 combined with ipilimumab (ipi) in patients (pts) with melanoma." 2014 ASCO Annual Meeting, No. 3010.
Heinkoff and Heinkoff (1992) Proc. Natl. Acad. Sci. USA 89:10915-10919.
Hoffmann et al., World J Gastroenterol. Jun. 14, 2007;13(22):3063-70.
Karlin and Altschul (1993) Proc. Natl. Acad. Sci. USA 90:5873-5787.
Liu et al. (2003) Gene Therapy 10:292-303.
Loskog, Angelica, "Immunostimulatory Gene Therapy Using Oncolytic Viruses as Vehicles," Viruses, 2015, 7:5780-5791.
MacLean et al. (1991) J. Gen. Virol. 72:631-639.
Piasecki et al., "Talimogene laherparepvec increases the anti-tumor efficacy of the anti-PD-1 immune checkpoint blockade," AACR Annual Meeting Presentation Abstract, Apr. 19, 2015.
Reese: "Abstract IA24: New frontiers in oncolytic virus therapy", Cancer Immunology Research, vol. 4, No. 11 Supplement, Nov. 1, 2016 (Nov. 1, 2016), pp. IA24-IA24.
Robinson et al., "Novel Immunocompetent Murine Tumor Model for Evaluation of Conditionally Replication-Competent (Oncolytic) Murine Adenoviral Vectors," Journal of Virology, 2009, 83(8):3450-3462.
Senzer et al., "Phase II Clinical Trial of a Granulocyte-Macrophage Colony-Stimulating Factor-Encoding, Second-Generation Oncolytic herpesvims in Patients with Unresectable Metastatic Melanoma" Journal of Clinical Oncology, 2009, 27(34):5763-5771.
Simpson, G.R. "Combination of a Fusogenic Glycoprotein, Prodrug Activation, and Oncolytic Herpes Simplex Virus for Enhanced Local Tumor Control", Cancer Research, vol. 66, No. 9, May 1, 2006 (May 1, 2006), pp. 4835-4842.
Sokolowski et al., "Oncolytic virotherapy using herpes simplex vims: how far have we come?" Oncolytic Virotherapy, 2015, 4:207-219.

(56) References Cited

OTHER PUBLICATIONS

Third Party Submission submitted in Related U.S. Appl. No. 16/068,823, dated Jul. 18, 2019.
Third Party Submission submitted in Related U.S. Appl. No. 16/068,826, dated Aug. 7, 2019.
Third Party Submission submitted in Related U.S. Appl. No. 16/068,830, dated Jul. 30, 2019.
Third Party Submission submitted in Related U.S. Appl. No. 16/068,816, dated Jul. 18, 2019.
Todo, "Special Focus: Glioma Therapy 'Armed' oncolytic herpes simplex vimses for C4 brain tumor therapy," Cell Adhesion & Migration, 2008, 2(3):208-213.
Yan et al., "Developing Novel Oncolytic Adenovimses through Bioselection," Journal of Virology, 2003, 77(4):2640-2650.
Output from Antibodypedia search for CTLA-4 Antibodies (performed Nov. 24, 2021), available at https://www.antibodYPedia.eom/gene/1 9961/CTLA4.
Output from Biocompare search for CTLA-4 Antibodies (performed Nov. 24, 2021), available at https://www.biocompare.com/Search-Antibodies/?search=CTLA-4&said=0.
Output from the National Institutes of Health (NIH) National Center for Biotechnology Information (NCBI) Taxonomy Browser searches for "herpesviridae", "poxviridae", "adenovirdae", "retroviridae", "rhabdoviridae", "paramyxoviridae", and "reoviridae" (performed Nov. 3, 2021), available at: https://www.ncbi.nlm.nih.gov/Taxonomy/Browser/wwwtax.cgi7mode =Root.
Pentcheva-Hoang et al. B7-1 and B7-2 Selectively Recruit CTLA-4 and CD28 to the Immunological Synapse, 21 Immunity 401-413 (Sep. 2004).
Petition for Post-Grant Review of U.S. Pat. No. 10,947,513, filed Dec. 15, 2021 with the TTAB, Petitioner—Transgene and Bioinvent International AB.
Yen et al. Vaccinia virus infection & temporal analysis of virus gene expression: Part 2, 2009(26) J. Vis. Exp. 1169 (Apr. 2009).
Reoviridae Information from Virus Pathogen Resource (ViPR) retrieved on Nov. 4, 2021, available at https://www.viprbrc.org/brc/aboutPathogen.spg?decorator=reo.
Ribas, Clinical Development of the Anti-CTLA-4 Antibody Tremelimumab, 37(5) Seminars in Oncology 450-454 (Oct. 2010).
Riedel et al. Components and Architecture of the Rhabdovirus Ribonucleoprotein Complex, 12(9) Viruses 2020 959 (Aug. 2020).
Rojas et al. Defining Effective Combinations of Immune Checkpoint Blockade and Oncolytic Virotherapy, 21(24) Clin. Cancer Res. 5543-51 (Dec. 2015).
Saha et al. The Adenovirus Genome Contributes to the Structural Stability of the Virion, 6(9) Viruses 2014 3563-3583 (Sep. 24, 2014).
Salzberg, Open questions: How many genes do we have? 16 BMC Biology 94 (Aug. 20, 2018).
Sharp and Li, The codon adaptation index—a measure of directional synonymous codon usage bias, and its potential applications, 15(3) Nucleic Acids Research 1281-95 (1987).
Singh et al. Oncolytic viruses & their specific targeting to tumour cells, 136 Indian J. Med. Res. 571-584 (Oct. 2012).
Sinkovics and Horvath, Natural and genetically engineered viral agents for oncolysis and gene therapy of human cancers, 56 Arch. Immunol. Ther. Exp. 3-59 (2008).
Smith et al. Studies on the Use of Viruses in the Treatment of Carcinoma of the Cervix, 9(6) Cancer 1211-18 (Nov.-Dec. 1956).
Species list extracted from International Committee on Taxonomy of Viruses (ICTY) Master Species List (Jul. 20, 2021), available at: https://talk.ictvonline.org/taxonomy/vmr/.
Study Details for Clinical Trial NCT02272855 "A Study of Combination Treatment With HF10 and Ipilimumab in Patients With Unresectable or Metastatic Melanoma", last updated Sep. 26, 2018, available at: https://clinicaltrials.gov/ct2/show/NCT02272855.
Study Details for Clinical Trial NCT02620423 "Study of Pembrolizumab with REOLYSIN® and Chemotherapy in Patients With Advanced Pancreatic Adenocarcinoma", last updated Sep. 13, 2018, available at: https://clinicaltrials.gov/ct2/show/NCT02620423.

Summary of Characteristics of Commercial Viral Vectors from ThermoFisher Scientific, retrieved Nov. 4, 2021, available at https://www.thermofisher.com/us/en/home/references/gibco-cell-culture-basics/transfection-basics/gene-delivery-technologies/viral-delivery/viral-vectors.html.
Tan et al. Combination therapy of oncolytic herpes simplex virus HF10 and bevacizumab against experimental model of human breast carcinoma xenograft, 136 Int. J. Cancer 1718-30 (2015).
Tesfay et al. PEGylation of Vesicular Stomatitis Virus Extends Virus Persistence in Blood Circulation of Passively Immunized Mice, 87(7) Journal of Virology 3752-59 (Apr. 2013).
Van den Wollenberg et al. Replicating reoviruses with a transgene replacing the codons for the head domain of the viral spike, 22 Gene Therapy 267-279 (2015).
Wennier et al. Bugs and Drugs: Oncolytic Virotherapy in Combination with Chemotherapy, 13(9) Curr. Pharm. Biotechnol. 1817-33 (Jul. 2012).
Wertz et al. Adding genes to the RNA genome of vesicular stomatitis virus: positional effects on stability of expression, 76(15) J. Virol. 7642-50 (Aug. 2002).
Willemsen and Zwart, On the stability of sequences inserted into viral genomes, 5(2) Virus Evolution vez045 (Jul. 2019).
Yang et al. Cascade regulation of vaccinia virus gene expression is modulated by multistage promoters, 447(1-2) Virology 213-220 (Dec. 2013).
Ahlers et al: "A push-pull approach to maximize vaccine efficacy: abrogating suppression with an IL-13 inhibitor while augmenting help with granulocyte/macrophage colony-stimulating factor and CD40L", Proc Natl Acad Sci USA, Oct. 1, 2002;99(20):13020-5.
Allison et al., "For Their Discovery of Cancer Therapy by Inhibition of Negative Immune in Physiology of Medicine Regulation"; The Nobel Assembly at Karolinska Institutet; 2018 Nobel Prize.
Yo, Y-T et al: "Coexpression of Flt3 ligand and GM-CSF genes modulates immune responses induced by HER2/neu DNA vaccine", Cancer Gene Ther. Nov. 2007;14(11):904-17.
Assal et al: "Emerging targets in cancer immunotherapy: beyond CTLA-4 and PD-1", Immunotherapy. 2015;7(11):1169-86.
Bauzon and Hermiston, 2014. Front. Immunol., 5(74): 1-10.
Todo, Tomoki, Armed oncolytic herpes simplex viruses for brain tumor therapy, 208-213, Cell Adhesion* Migration 2:3, Jul./Aug./Sep. 2008.
Capece et al: "Targeting costimulatory molecules to improve antitumor immunity", J Biomed Biotechnol, 2012; 2012:926321.
Cell Signaling Technology; Immune Checkpoint Signaling in the Tumor Microenvironment1; Mar. 2018.
Third Party Submission submitted in Related U.S. Appl. No. 16/068,830, dated Jul. 18, 2019.
Chen et al., "Dual silencing of Bcl-2 and Survivin by HSV-1 vector shows better antitumor efficacy in higher PKR phosphorylation tumor cells in vitro and in vivo", Cancer Gene Ther 22, 380-386; 2015.
Choi et al., "Concurrent delivery of GM-CSF and B7-1 using an oncolytic adenovirus elicits potent antitumor effect", Gene Therapy (2006) 13, 1010-1020 & 2006 Nature Publishing Group.
Choi et al., "Strengthening of antitumor immune memory and prevention of thymic atrophy mediated by adenovirus expressing IL-12 and GM-CSF", Gene Therapy (2012) 19, 711-723 & 2012 Macmillan Publishers.
Chou et al., "Mapping of Herpes Simplex Virus-1 Neurovirulence to ?134.5, a Gene Nonessential for Growth in Culture," Science, 1990, 250(4985):1262-1266.
Dias et al., 2012. Gene Ther., 19: 988-998.
Hu et al. "A simplified system for generating oncolytic adenovirus vector carrying one or two transgenes", Cancer Gene Therapy (2008) 15, 173-182 r 2008 Nature Publishing Group.
Gao et al: "Recombinant vesicularm stomatitis virus targeted to Her2/neu combined with anti-CTLA4 antibody eliminates implanted mammary tumors", Cancer Gene Ther. Jan. 2009;16(1):44-52.
Gri et al: "X40 ligand-transduced tumor cell vaccine synergizes with GM-CSF and requires CD40-Apc signaling to boost the host T cell antitumor response", J Immunol. Jan. 1, 2003;170(1):99-106.
Hoggmann et al. W.J. G 2007, Jun. 14, 13 (22), pp. 3063-30700.

(56) References Cited

OTHER PUBLICATIONS

Hurwitz et al: "CTLA-4 blockade synergizes with tumor-derived granulocyte-macrophage colony-stimulating factor for treatment of an experimental mammary carcinoma", Proc Natl Acad Sci USA, Aug. 18, 1998;95(17):10067-71.
Third Party Submission submitted in Related U.S. Appl. No. 16/068,816, dated Jul. 16, 2019.
Sumimoto et al: "GM-CSF and B7-1 (CD80) co-stimulatory signals co-operate in the induction of effective anti-tumor immunity in syngeneic mice", Int J Cancer. Nov. 14, 1997;73(4):556-61.
Statement of Grounds of Opposition from the Opponent, Margaret Dixon Limited, dated Jun. 7, 2021, EP3400293 (EP Appl. No. 17701910.6).
Kaufman et al: "Oncolytic viruses: a new class of immunotherapy drugs", Nat Rev Drug Discov, vol. 14, 642-662 (Sep. 2015).
Lee et al: "Oncolytic potential of E1B 55 kDa-deleted YKL-1 recombinant adenovirus: correlation with p53 functional status" Int J Cancer (2000) 88: 454-463.
Li, B et al: "Established B16 tumors are rejected following treatment with GM-CSF-secreting tumor cell immunotherapy in combination with anti-4-1 BB mAb", Clin Immunol. Oct. 2007;125(1):76-87.
Li, B. et al: "Anti-programmed death-1 synergizes with granulocyte macrophage colony-stimulating factor-secreting tumor cell immunotherapy providing therapeutic benefit to mice with established tumors", Clin Cancer Res. Mar. 1, 2009;15(5):1623-34.
Maclean et al., "Herpes simplex cirus type 1 deletion variants 1714 and 1716 pinpoint neurovirulence-related sequences in Glasgow strain 17 + between immediate early gene 1 and the 'a' sequence," Journal of General Virology, 1991, 72:631-639.
Murata et al: "X40 costimulation synergizes with GM-CSF whole-cell vaccination to overcome established CD8+ T cell tolerance to an endogenous tumor antigen", J Immunol. Jan. 15, 2006;176(2):974-83.
Office Action issued in European Patent Application No. 1770385, dated May 21, 2019.
Reese, "Abstract IA24: New frontiers in oncolytic virus therapy," Cancer Immunology Research, 2016, 4(11):1A24-1A24.
Robbins et al; "Viral Vectors for Gene Therapy"; Pharmacol, Ther.; vol. 80, No. 1; pp. 35-47; 1998.
Simpson et al., "Combination of a Fusogenic Glycoprotein, Prodrug activation, and Oncolytic Herpes Simplex Virus for Enhanced Local Tumor Control," Cancer Research, 2006, 66(9):4835-4842.
Excerpts from S. Baron (Ed.), Medical Microbiology, 4th. Ed. University of Texas Medical Branch at Galveston (1996).
Ahmed et al, Intratumoral expression of a fusogenic membrane glycoprotein enhances the efficacy of replicating adenovirus therapy, 10 Gene Therapy 1663-71 (2003).
Asada, Treatment of Human Cancer with Mumps Virus, 34(6) Cancer 1907-28 (Dec. 1974).
Balvay et al. Translational control of retroviruses, 5 Nature Reviews Microbiology 128-140 (Feb. 2007).
Belsham and Sonenberg, RNA-protein interactions in regulation of picornavirus RNA translation, 60(3) Microbiological Reviews 499-511 (Sep. 1996).
Bett et al. Packaging capacity and stability of human adenovirus type 5 vectors, 67(10) J. Virol. 5911-21 (Oct. 1993).
Blechacz et al. Engineered Measles Virus as a Novel Oncolytic Viral Therapy System for Hepatocellular Carcinoma, 44(6) Hepatology 1465-77 (Dec. 2006).
Brochu-Lafontaine and Lemay, Addition of exogenous polypeptides on the mammalian reovirus outer capsid using reverse genetics, 179 J. Virol. Methods 342-350 (2012).
Carter et al. Identification of an overprinting gene in Merkel cell polyomavirus provides evolutionary insight into the birth of viral genes, 110(31) Proceedings of the National Academy of Sciences 12744-49 (Jul. 2013).
Choi et al. Polymeric oncolytic adenovirus for cancer gene therapy, 219 Journal of Controlled Release 181-191 (2015).

Compilation of Virus Information from Swiss Institute of Bioinformatics retrieved on Nov. 3, 2021, available at https://viralzone.expasy.org/.
Croyle et al. PEGylation of a Vesicular Stomatitis Virus G Pseudotyped Lentivirus Vector Prevents Inactivation in Serum, 78(2) Journal of Virology 912-921 (Jan. 2004).
Danthinne and Imperiale, Production of first generation adenovirus vectors: a review, 7 Gene Therapy 1707-14 (2000).
Declaration of Dr. Sylvia D. Hall-Ellis dated Nov. 29, 2021 and Curriculum vitae.
Declaration of John C. Bell, Ph.D. dated Dec. 14, 2021 and Curriculum vitae.
Deguchi et al. Combination of the Tumor Angiogenesis Inhibitor Bevacizumab and Intratumoral Oncolytic Herpes Virus Injections as a Treatment Strategy for Human Gastric Cancers, 59(118) Hepatogastroenterology 1844-50 (Sep. 2012).
Dikstein, The unexpected traits associated with core promoter elements, 2(5) Transcription 201-206 (Sep. 2011).
Documents filed on Jul. 9, 2018 in U.S. Appl. No. 16/068,830, including original application, preliminary amendment, application data sheet, search report, and transmittal form.
Donovan-Banfield et al. Deep splicing plasticity of the human adenovirus type 5 transcriptome drives virus evolution, 3 Communications Biology (2020) 124.
Ebert et al. Syncytia Induction Enhances the Oncolytic Potential of Vesicular Stomatitis Virus in Virotherapy for Cancer, 64 CANCER Research 3265-3270 (May 2004).
Engeland et al. CTLA-4 and PD-L1 Checkpoint Blockade Enhances Oncolytic Measles Virus Therapy, 22(11) Molecular Therapy 1949-59 (Nov. 2014).
Fu et al. Expression of a Fusogenic Membrane Glycoprotein by an Oncolytic Herpes Simplex Virus Potentiates the Viral Antitumor Effect, 7(6) Molecular Therapy 748-754 (Jun. 2003).
Fukuhara et al. Triple Gene-Deleted Oncolytic Herpes Simplex Virus Vector Double-Armed with Interleukin 18 and Soluble B7-1 Constructed by Bacterial Artificial Chromosome-Mediated System, 65(23) Cancer Res. 10663-68 (Dec. 2005).
Guedan et al. GALVexpression enhances the therapeutic efficacy of an oncolytic adenovirus by inducing cell fusion and enhancing virus distribution, 19 Gene Therapy 1048-57 (2012).
Gómez-Trevino et al. Effects of adenovirus-mediated SV5 fusogenic glycoprotein expression on tumor cells, 5 J. Gene Med. (2003) 483-492.
Herpesviridae Information from Virus Pathogen Resource (ViPR) retrieved on Nov. 4, 2021, available at: https://www.viprbrc.org/brc/aboutPathogen.spg7decoratoiHierpes.
Hillier et al. Genomics in C. elegans: so many genes, such a little worm, 15 Genome Research 1651-60 (2005).
Ho et al. Unconventional viral gene expression mechanisms as therapeutic targets, 593 Nature 362-371 (May 2021).
International Search Report for International Patent Application No. PCT/EP2015/066263, mailed from European Patent Office Oct. 7, 2015.
International Search Report for International Patent Application No. PCT/FI2009/051025, mailed from European Patent Office Mar. 24, 2010.
Ishihara et al. Systemic CD8+ T Cell-Mediated Tumoricidal Effects by Intratumoral Treatment of Oncolytic Herpes Simplex Virus with the Agonistic Monoclonal Antibody for Murine Glucocorticoid-Induced Tumor Necrosis Factor Receptor, 9(8) PLOS One e104669 (Aug. 2014).
Ishikawa et al. STING regulates intracellular DNA-mediated, type I interferon-dependent innate immunity, 461 Nature 788-792 (Oct. 8, 2009).
Jacobs et al. HSV-1 based vectors for gene therapy of neurological diseases and brain tumors Part II Vector Systems and Applications, 1(5) Neoplasia 402-416 (Nov. 1999).
Jacobs et al. Vaccinia Virus Vaccines: Past, Present and Future, 84(1) Antiviral Res. 1-13 (Oct. 2009).
John et al. Oncolytic Virus and Anti-4-IBB Combination Therapy Elicits Strong Antitumor Immunity against Established Cancer, 72(7) Cancer Research 1651-60 (Apr. 2012).

(56) References Cited

OTHER PUBLICATIONS

Kaufmann et al. Chemovirotherapy of Malignant Melanoma with a Targeted and Armed Oncolytic Measles Virus, 133 Journal of Investigative Dermatology 1034-42 (2013).

Kelly and Russell, History of Oncolytic Viruses: Genesis to Genetic Engineering, 15(4) Molecular Therapy 651-659 (Apr. 2007).

Le Boeuf et al. Synergistic Interaction Between Oncolytic Viruses Augments Tumor Killing, 18(5) Molecular Therapy 888-895 (May 2010).

Lee et al. Enhanced Antitumor Effect of Oncolytic Adenovirus Expressing Interleukin-12 and B7-1in an Immunocompetent Murine Model, 12(19) Clin. Cancer Res. 5859-68 (Oct. 2006).

Lipson and Drake, Ipilimumab: An Anti-CTLA-4 Antibody for Metastatic Melanoma, 17(22) Clin. Cancer Res. 6958-62 (Nov. 2011).

List of known isolates within each virus family extracted from NCBI Taxonomy Browser Output of Ex. 1023.

Lundstrom, New frontiers in oncolytic viruses: optimizing and selecting for virus strains with improved efficacy, 12 Biologics: Targets and Therapy 43-60 (2018).

Ma et al. Oncolytic herpes simplex virus and immunotherapy, 19 BMC Immunology 40 (2018).

Majid et al. Recombinant Vesicular Stomatitis Virus (VSV) and Other Strategies in HCV Vaccine Designs and Immunotherapy. Tan SL, (Ed.) Hepatitis C Viruses: Genomes and Molecular Biology, Ch. 15. Norfolk (UK): Horizon Bioscience (2006).

Malhotra et al. Use of an Oncolytic Virus Secreting GM-CSF as Combined Oncolytic and Immunotherapy for Treatment of Colorectal and Hepatic Adenocarcinomas, 141(4) Surgery 520-529 (Apr. 2007).

McDonald et al. A measles virus vaccine strain derivative as a novel oncolytic agent against breast cancer, 99 Breast Cancer Research and Treatment 177-184 (2006).

Msaouel et al. Attenuated oncolytic Measles Virus strains as cancer therapeutics, 13(9) Curr. Pharm. Biotechnol. 1732-41 (Jul. 1, 2012).

Nakamori et al. Potent Antitumor Activity After Systemic Delivery of a Doubly Fusogenic Oncolytic Herpes Simplex Virus Against Metastatic Prostate Cancer, 60 The Prostate 53-60 (2004).

Oliveira et al. Poxvirus Host Range Genes and Virus-Host Spectrum: A Critical Review, 9(11) Viruses 2017 331 (Nov. 7, 2017).

Output from antibodies-online.com search for CTLA-4 Antibodies (performed Nov. 24, 2021), available at https://www.antibodies-online.eom/search.php#5qk9.

Liu et al., "ICP34.5 deleted herpes simplex cirus with enhanced oncolytic, immune stimulating, and anti-tumour properties," Gene Therapy, 2003, 10(4):292-303.

Kleinpeter et al. Vectorization in an oncolytic vaccinia virus of an antibody, a Fab and a scFv against programmed cell death-1 (PD-1) allows their intratumoral delivery and an improved tumor-growth inhibition, 5(10) Oncoimmunology e1220467 (2016).

Annex A—WO 2017/118864—Figures 3 and 4 published Jul. 13, 2017.

Carson et al., "Oncolytic Herpe Simplex Virus 1 (HSV-1) Vectors: Increasing Treatment Efficacy and Range Throught Strategic Virus Design", Drugs Future. 2010,35(3): 183-195.

Fransen et al., "Controlled Local Delivery of CTLA-4 Blocking Antibody Induces CD8+ T-Cell-Dependent Tumor Eradication and Decreaes Risk of Toxic Side Effects" Clin Cancer Res. 2013, 19(19):5381-9.

Hooren et al., "Abstract B103: Intralesional administration of CTLA-4 blocking monoclonal antibodies as a means to optimize bladder cancer therapy", Cancer Immunol Res. 2016,4 (11_Supplement): B103.

Hooren et al., "Local checkpoint inhibition of CTLA-4 as a monotherapy or in combination with anti-PD1 prevents the growth of murine bladder cancer" Eur J Immunol. 2017,47(2):385-393.

Marabelle et al., "Intratumoral Anti-CTLA-4 Therapy: Enhancing Efficacy While Avoiding Toxicity", Clin Cancer Res. 2013, 19(19):5261-3.

Fielding et al. "A hyperfusogenic gibbon apeleukemia envelope glycoprotein: targeting of a cytotoxic gene by ligand display", Hum Gene Ther. Apr. 10, 2000;11(6):817-26.

Alekseenko et al: "Therapeutic properties of a vector carrying the HSV thymidine kinase and GM-CSF genes and delivered as a complex with a cationic copolymer", Journal of Translational Medicine (2015) 13:78.

EPO Opposition "Opponent's Response in opposition proceedings against Replimune's European Patent EP 3400291", provided by the European Patent Office on May 4, 2023.

Fonteneau et al., "Oncolytic immunotherapy: The new clinical outbreak", OncoImmunology, 2016, 5:1,e1066961.

Japanese Notice of Rejection mailed Feb. 28, 2023 during examination of related JP Patent Appl. No. 2019-537074.

Marcos et al., "Mapping of the RNA promoter of Newcastle disease virus", Virology, vol. 331, Issue 2, 2005, pp. 396-406.

Noton and Fearns, "Initiation and regulation of paramyxovirus transcription and replication", Virology, 2015, 479-480, 545-554.

\* cited by examiner

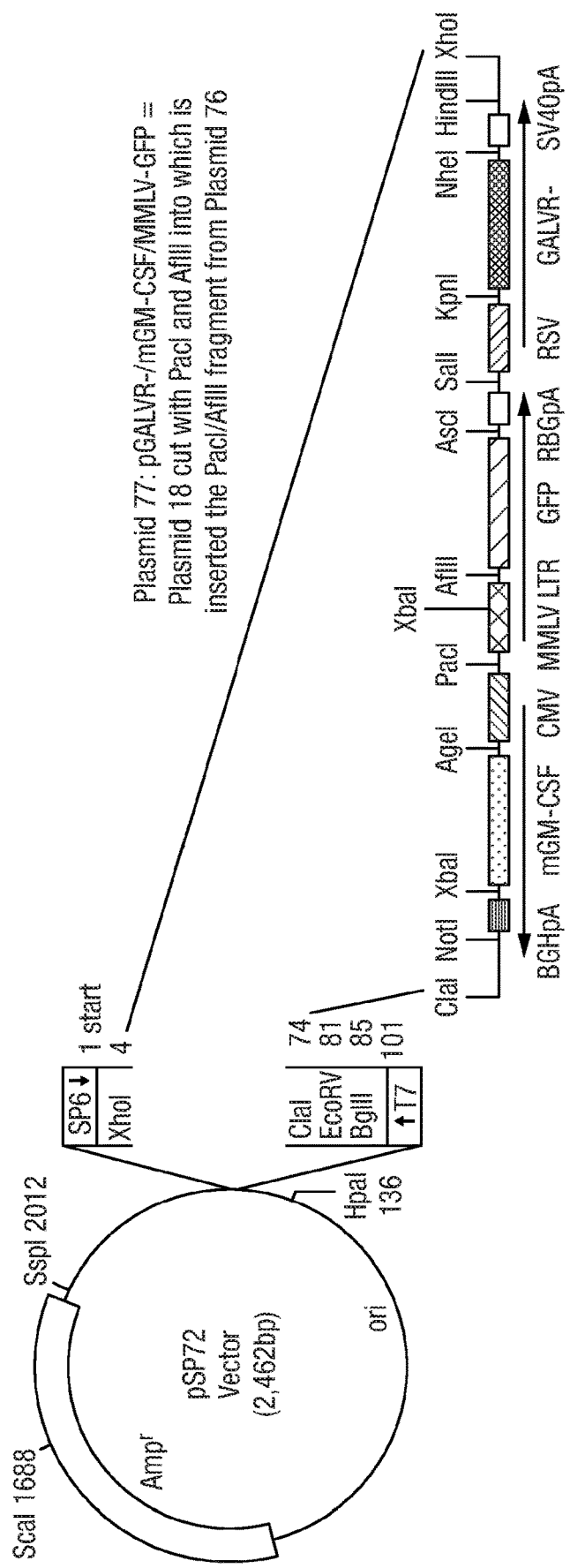

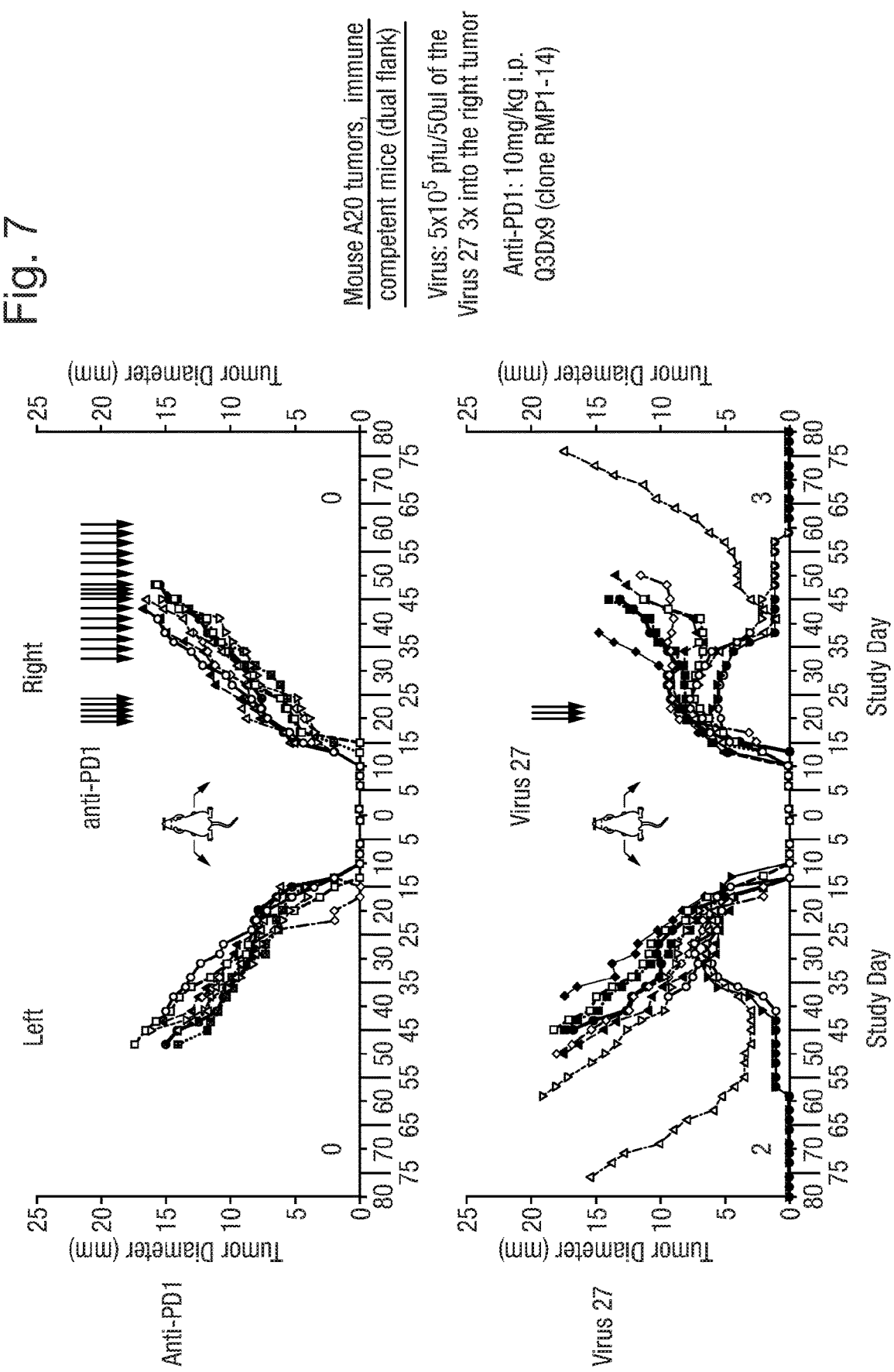

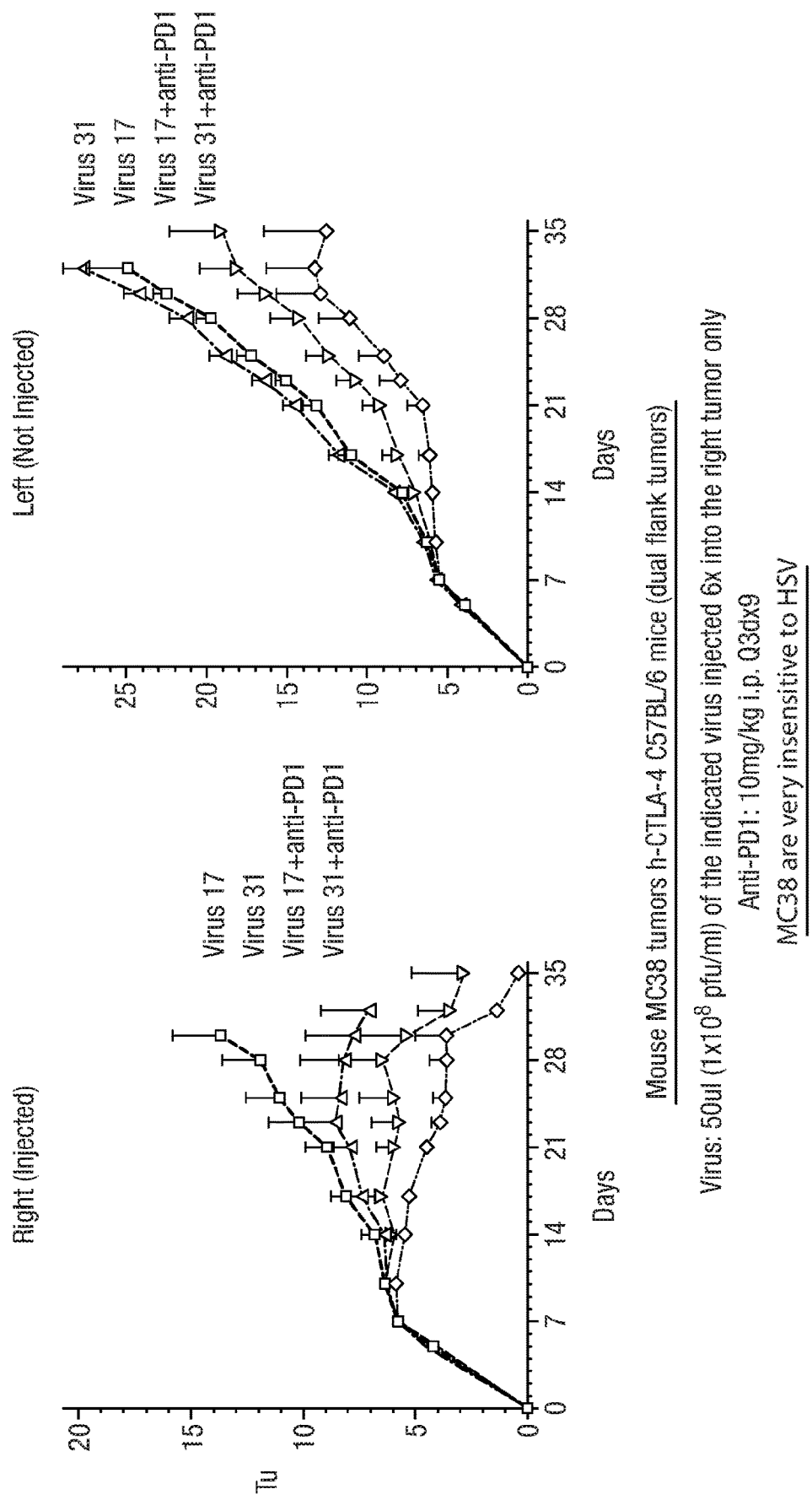

ALTERED VIRUS

CROSS-REFERENCE TO RELATED APPLICATIONS

This application is a national phase application under 35 U.S.C. § 371 that claims priority to International Application No. PCT/GB2018/050048 filed Jan. 9, 2018, which claims priority to United Kingdom Patent Application No. 1700350.0, filed Jan. 9, 2017, all of which are incorporated herein by reference in their entirety.

FIELD OF THE INVENTION

The invention relates to an oncolytic immunotherapeutic agent and to the use of the oncolytic immunotherapeutic agent in treating cancer.

BACKGROUND TO THE INVENTION

Viruses have a unique ability to enter cells at high efficiency. After entry into cells, viral genes are expressed and the virus replicates. This usually results in the death of the infected cell and the release of the antigenic components of the cell as the cell ruptures as it dies. As a result, virus mediated cell death tends to result in an immune response to these cellular components, including both those derived from the host cell and those encoded by or incorporated into the virus itself and enhanced due to the recognition by the host of so called damage associated molecular patterns (DAMPs) which aid in the activation of the immune response.

Viruses also engage with various mediators of the innate immune response as part of the host response to the recognition of a viral infection through e.g. toll-like receptors and cGAS/STING signalling and the recognition of pathogen associated molecular patterns (PAMPs) resulting in the activation of interferon responses and inflammation which are also immunogenic signals to the host. These immune responses may result in the immunogenic benefit to cancer patients such that immune responses to tumor antigens provide a systemic overall benefit resulting in the treatment of tumors which have not been infected with the virus, including micro-metastatic disease, and providing vaccination against relapse.

The combined direct ('oncolytic') effects of the virus, and immune responses against tumor antigens (including non-self 'neo-antigens', i.e. derived from the particular mutated genes in individual tumors) is termed 'oncolytic immunotherapy'.

Viruses may also be used as delivery vehicles ('vectors') to express heterologous genes inserted into the viral genome in infected cells. These properties make viruses useful for a variety of biotechnology and medical applications. For example, viruses expressing heterologous therapeutic genes may be used for gene therapy. In the context of oncolytic immunotherapy, delivered genes may include those encoding specific tumor antigens, genes intended to induce immune responses or increase the immunogenicity of antigens released following virus replication and cell death, genes intended to shape the immune response which is generated, genes to increase the general immune activation status of the tumor, or genes to increase the direct oncolytic properties (i.e. cytotoxic effects) of the virus. Importantly, viruses have the ability to deliver encoded molecules which are intended to help to initiate, enhance or shape the systemic anti-tumor immune response directly and selectively to tumors, which may have benefits of e.g. reduced toxicity or of focusing beneficial effects on tumors (including those not infected by the virus) rather than off-target effects on normal (i.e. non-cancerous) tissues as compared to the systemic administration of these same molecules or systemic administration of other molecules targeting the same pathways.

It has been demonstrated that a number of viruses including, for example, herpes simplex virus (HSV) have utility in the oncolytic treatment of cancer. HSV for use in the oncolytic treatment of cancer must be disabled such that it is no longer pathogenic, but can still enter into and kill tumor cells. A number of disabling mutations to HSV, including disruption of the genes encoding ICP34.5, ICP6, and/or thymidine kinase, have been identified which do not prevent the virus from replicating in culture or in tumor tissue in vivo, but which prevent significant replication in normal tissue. HSVs in which only the ICP34.5 genes have been disrupted replicate in many tumor cell types in vitro, and replicate selectively in tumor tissue, but not in surrounding tissue, in mouse tumor models.

Clinical trials of ICP34.5 deleted, or ICP34.5 and ICP6 deleted, HSV have also shown safety and selective replication in tumor tissue in humans.

As discussed above, an oncolytic virus, including HSV, may also be used to deliver a therapeutic gene in the treatment of cancer. An ICP34.5 deleted virus of this type additionally deleted for ICP47 and encoding a heterologous gene for GM-CSF has also been tested in clinical trials, including a phase 3 trial in melanoma in which safety and efficacy in man was shown. GM-CSF is a pro-inflammatory cytokine which has multiple functions including the stimulation of monocytes to exit the circulation and migrate into tissue where they proliferate and mature into macrophages and dendritic cells. GM-CSF is important for the proliferation and maturation of antigen presenting cells, the activity of which is needed for the activation of an anti-tumor immune response. The trial data demonstrated that tumor responses could be seen in injected tumors, and to a lesser extent in uninjected tumors. Responses tended to be highly durable (months-years), and a survival benefit appeared to be achieved in responding patients. Each of these indicated engagement of the immune system in the treatment of cancer in addition to the direct oncolytic effect. However, this and other data with oncolytic viruses generally showed that not all tumors respond to treatment and not all patients achieve a survival advantage. Thus, improvements to the art of oncolytic therapy are clearly needed.

Recently it has been shown that oncolytic immunotherapy can result in additive or synergistic therapeutic effects in conjunction with immune co-inhibitory pathway blockade (i.e. inhibition or 'antagonism' of immune checkpoint pathways, also termed immune co-inhibitory pathways). Immune co-inhibitory pathway blockade is intended to block host immune inhibitory mechanisms which usually serve to prevent the occurrence of auto-immunity. However, in cancer patients these mechanisms can also serve to inhibit the induction of or block the potentially beneficial effects of any immune responses induced to tumors.

Systemic blockade of these pathways by agents targeting cytotoxic T lymphocyte-associated molecule-4 (CTLA-4), PD-1 or PD-L1 have shown efficacy in a number of tumor types, including melanoma and lung cancer. However, unsurprisingly, based on the mechanism of action, off target toxicity can occur due to the induction of auto-immunity. Even so, these agents are sufficiently tolerable to provide considerable clinical utility. Other immune co-inhibitory pathway and related targets for which agents (mainly antibodies) are in development include LAG-3, TIM-3, VISTA, CSF1R, IDO, CEACAM1, CD47. Optimal clinical activity of these agents, for example PD1, PDL1, LAG-3, TIM-3, VISTA, CSF1R, IDO, CD47, CEACAM1 may require systemic administration or presence in all tumors due to the mechanism of action, i.e. including targeting of the interface of immune effector cells with tumors or other immune inhibitory mechanisms in/of tumors in some cases, more localised presence in e.g. just some tumors or in some lymph nodes may also be optimally effective, for example agents targeting CTLA-4.

An alternative approach to increasing the anti-tumor immune response in cancer patients is to target (activate) immune co-stimulatory pathways, i.e. in contrast to inhibiting immune co-inhibitory pathways. These pathways send activating signals into T cells and other immune cells, usually resulting from the interaction of the relevant ligands on antigen presenting cells (APCs) and the relevant receptors on the surface of T cells and other immune cells. These signals, depending on the ligand/receptor, can result in the increased activation of T cells and/or APCs and/or NK cells and/or B cells, including particular sub-types, increased differentiation and proliferation of T cells and/or APCs and/or NK cells and/or B cells, including particular sub-types, or suppression of the activity of immune inhibitory T cells such as regulatory T cells. Activation of these pathways would therefore be expected to result in enhanced anti-tumor immune responses, but it might also be expected that systemic activation of these pathways, i.e. activation of immune responses generally rather than anti-tumor immune responses specifically or selectively, would result in considerable off target toxicity in non-tumor tissue, the degree of such off target toxicity depending on the particular immune co-stimulatory pathway being targeted. Nevertheless agents (plainly agonistic antibodies, or less frequently the soluble ligand to the receptor in question) targeting immune co-stimulatory pathways, including agents targeting GITR, 4-1-BB, OX40, CD40 or ICOS, and intended for systemic use (i.e. intravenous delivery) are in or have been proposed for clinical development.

For many of these approaches targeting immune co-inhibitory or co-inhibitory pathways to be successful, pre-existing immune responses to tumors are needed, i.e. so that a pre-existing immune response can be potentiated or a block to an anti-tumor immune response can be relieved. The presence of an inflamed tumor micro-environment, which is indicative of such an ongoing response, is also needed. Pre-existing immune responses to tumor neo-antigens appear to be particularly important for the activity of immune co-inhibitory pathway blockade and related drugs. Only some patients may have an ongoing immune response to tumor antigens including neoantigens and/or an inflamed tumor microenvironment, both of which are required for the optimal activity of these drugs. Therefore, oncolytic agents which can induce immune responses to tumor antigens, including neoantigens, and/or which can induce an inflamed tumor microenvironment are attractive for use in combination with immune co-inhibitory pathway blockade and immune potentiating drugs. This likely explains the promising combined anti-tumor effects of oncolytic agents and immune co-inhibitory pathway blockade in mice and humans that have so far been observed.

The above discussion demonstrates that there is still much scope for improving oncolytic agents and cancer therapies utilising oncolytic agents, anti-tumor immune responses and drugs which target immune co-inhibitory or co-stimulatory pathways.

SUMMARY OF THE INVENTION

The present invention provides oncolytic viruses expressing an inhibitor of CTLA-4. The virus may further comprise other immunomodulatory agents. In particular the virus may comprise GM-CSF and/or at least one molecule targeting an immune co-stimulatory pathway. The CTLA-4 inhibitor acts to block a co-inhibitory pathway, i.e. interferes with the interaction between CTLA-4 and B7. GM-CSF aids in the induction of an inflammatory tumor micro-environment and stimulates the proliferation and maturation of antigen presenting cells, including dendritic cells, aiding the induction of an anti-tumor immune responses. These immune responses may be amplified through activation of an immune co-stimulatory pathway or pathways using an immune co-stimulatory pathway activating molecule or molecules also delivered by the oncolytic virus.

Oncolytic viruses replicate within tumors, causing lysis of tumor cells and release of tumor antigens, combined with local inflammation and activation of innate immune responses, all of which are beneficial for the activation of an anti-tumor immune response and for the activity of inhibitors of the CTLA-4/B7 interaction.

Delivery of molecules that inhibit the CTLA-4/B7 interaction directly into an immune response initiating-tumor, including where it would be expected to traffic to draining lymph nodes, focuses immune potentiation by the inhibitor on the tumor and therefore on tumor antigens present within it, reduces systemic toxicity and blocks regulatory T cell (Treg) activation that would otherwise inhibit T-cell activation at the site of immune response initiation. The use of an oncolytic virus to deliver molecules targeting CTLA-4, and optionally molecules targeting immune co-stimulatory pathways to tumors focuses the amplification of immune effects on anti-tumor immune responses, and reduces the amplification of immune responses to non-tumor antigens. Thus, immune cells in tumors and tumor draining lymph nodes are selectively affected by the molecules expressed by the virus rather than immune cells in general. This results in enhanced efficacy of immune cell stimulation, and can also result in reduced off target toxicity. It is also important for focusing the effects of combined systemic immune co-inhibitory pathway blockade and immune co-stimulatory pathway activation on tumors, i.e. such that the amplified immune responses from which co-inhibitory blocks are released are antitumor immune responses rather than responses to non-tumor antigens.

The invention utilizes the fact that, when delivered by an oncolytic virus, the site of action of CTLA-4 blockade and optionally co-stimulatory pathway activation and of GM-CSF expression is in the tumor and/or tumor draining lymph node, but the results of such activation (an amplified systemic anti-tumor-immune response) are systemic. This targets tumors generally, and not only tumors to which the oncolytic virus has delivered the immunomodulatory molecule or molecules. Oncolytic viruses of the invention therefore provide improved treatment of cancer through the generation of improved tumor focused immune responses. The oncolytic virus of the invention also offers improved anti-tumor immune stimulating effects such that the immune-mediated effects on tumors which are not destroyed by oncolysis, including micro-metastatic disease, are enhanced, resulting in more effective destruction of these tumors, and more effective long term anti-tumor vaccination to prevent future relapse and improve overall survival.

Anti-tumor efficacy is improved when an oncolytic virus of the invention is used as a single agent and also when the virus is used in combination with other anti-cancer modalities, including chemotherapy, treatment with targeted agents, radiation and, in preferred embodiments, immune checkpoint blockade drugs (i.e. antagonists of an immune co-inhibitory pathway, for example antibodies against PD1 or PD-L1) and/or agonists of an immune co-stimulatory pathway.

Accordingly, the present invention provides an oncolytic virus encoding a CTLA-4 inhibitor. The CTLA-4 inhibitor is preferably an anti-CTLA-4 antibody or antibody like molecule, or an antigen binding fragment thereof.

The virus may further comprise: (i) a GM-CSF-encoding gene; and/or (ii) an immune co-stimulatory pathway activating molecule or immune co-stimulatory pathway activating molecule-encoding gene. The virus may encode more than one immune co-stimulatory pathway activating molecule/gene.

The immune co-stimulatory pathway activating molecule is preferably GITRL, 4-1-BBL, OX40L, ICOSL or CD40L or a modified version of any thereof. Examples of modified versions include agonists of a co-stimulatory pathway that are secreted rather than being membrane bound, and/or agonists modified such that multimers of the protein are formed.

The virus may be a modified clinical isolate, such as a modified clinical isolate of a virus, wherein the clinical isolate kills two or more tumor cell lines more rapidly and/or at a lower dose in vitro than one or more reference clinical isolates of the same species of virus.

The virus is preferably a herpes simplex virus (HSV), such as HSV1, The HSV typically does not express functional ICP34.5 and/or functional ICP47 and/or expresses the US11 gene as an immediate early gene.

The invention also provides:
- a pharmaceutical composition comprising a virus of the invention and a pharmaceutically acceptable carrier or diluent;
- the virus of the invention for use in a method of treating the human or animal body by therapy;
- the virus of the invention for use in a method of treating cancer, wherein the method optionally comprises administering a further anti-cancer agent;
- a product of manufacture comprising a virus of the invention in a sterile vial, ampoule or syringe;
- a method of treating cancer which comprises administering a therapeutically effective amount of a virus or a pharmaceutical composition of the invention to a patient in need thereof wherein the method optionally comprises administering a further anti-cancer agent;
- use of a virus of the invention in the manufacture of a medicament for use in a method of treating cancer, wherein the method optionally comprises administering a further anti-cancer agent.

BRIEF DESCRIPTION OF THE FIGURES

FIG. 8 shows the superior tumor control and shrinkage effects of virus 31 expressing hGM-CSF, GALVR and anti-human CTLA-4 compared to virus 17 expressing only hGM-CSF and GALVR in mouse MC38 tumors in knock-in mice expressing human CTLA-4. The anti-tumor effects of virus 31 are observed when the virus is administered alone or in combination with anti-PD1. Superior tumor control and shrinkage in injected tumors is obtained with virus 31 which expresses anti-human CTLA-4 compared with an otherwise identical virus that does not express anti-human CTLA-4 (left panel). This effect is further enhanced when treatment with the virus is combined with anti-PD1 treatment. Superior tumor control and shrinkage is also observed in uninjected tumors (right panel) when treatment with either virus is combined with anti-PD1 treatment. This improvement is more marked for the virus 31 that expresses anti CTLA-4 than for virus 17 which does not. Each line represents a different mouse.

BRIEF DESCRIPTION OF THE SEQUENCE LISTING

Figure 1A:
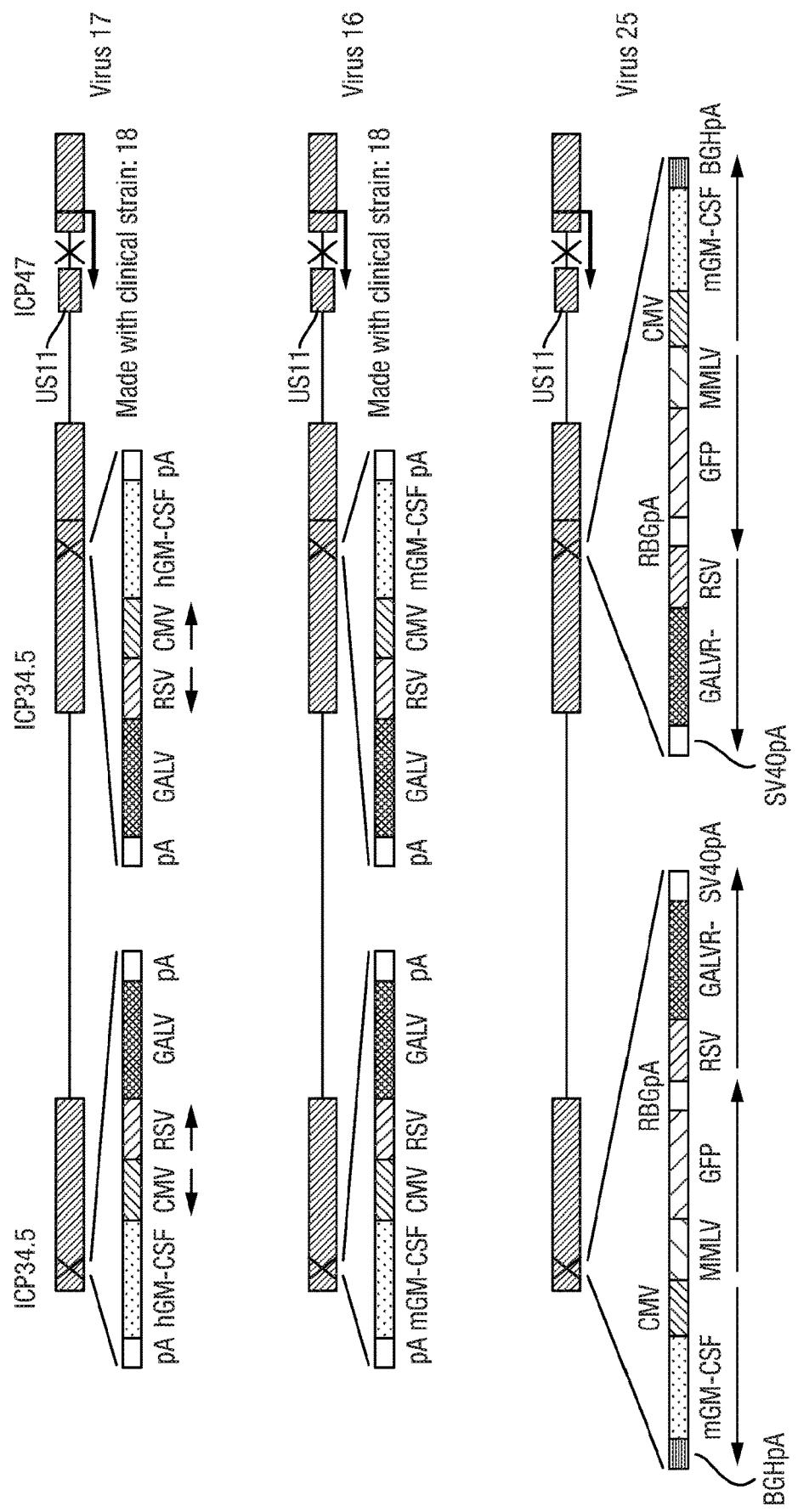
FIG. 1 depicts the structures of the viruses used to construct exemplary viruses of the invention that comprise anti-mouse or anti-human CTLA-4 constructs that are codon optimized secreted scFv molecules linked to human or mouse IgG1 Fc regions. The scFvs contain light and heavy variable chains from 9D9 (the initial mouse antibody initially used to validate CTLA-4; WO2007/123737: mouse version) or from ipilimumab. (WO2014/066532; human version) linked by the 15-mer $[G_4S]_3$ (GGGGSGGGGSGGGGS). The viruses are modified versions of strain HSV1 RH018A (clinical strain 18). The ICP34.5 and ICP47 genes are inactivated in the viruses. The US11 gene is placed under the control of the ICP47 immediate early gene promoter by deletion of the ICP47 promoter. An expression cassette is inserted into the ICP34.5 gene loci. In virus 17, the expression cassette includes the human GM-CSF gene under the control of a CMV promoter and the GALV gene under the control of a RSV promoter. Virus 16 is the same as virus 17, except that human GM-CSF is included instead of mouse GM-CSF. Viruses 25 and 29 are the same as viruses 16 and 17, respectively, except that they each additionally comprise a GFP gene under the control of a MMLV promoter in the expression cassette. Viruses 27 and 31 are the same as viruses 25 and 29, respectively, except that the GFP gene is replaced with mouse anti-CTLA4 and human anti-CTLA4, respectively.

SEQ ID NO: 1 is the light chain variable region amino acid sequence of the human CTLA-4 antibody used in the Examples.

SEQ ID NOs: 2 is the complete light chain amino acid sequence comprising the light chain variable region amino acid sequence of the human CTLA-4 antibody used in the Examples.

SEQ ID NO: 3 is the heavy chain variable region amino acid sequence of the human CTLA-4 antibody used in the Examples.

SEQ ID NO: 4 is the heavy chain CH1 amino acid sequence of the human CTLA-4 antibody used in the Examples.

SEQ ID NO: 5 is the heavy chain CH2/3 amino acid sequence of the human CTLA-4 antibody used in the Examples.

SEQ ID NO: 6 is the complete heavy chain amino acid sequence of the human CTLA-4 antibody used in the Examples.

SEQ ID NO: 7 is the amino acid sequence of the signal peptide present in the CTLA-4 antibodies of the Examples.

SEQ ID NO: 8 is the amino acid sequence of the linker present between the light chain variable region and the heavy chain variable region in the CTLA-4 antibodies of the Examples.

SEQ ID NO: 9 is the amino acid sequence of the human scFv CTLA-4 antibody of the Examples.

SEQ ID NO: 10 is the nucleotide sequence of the human scFv CTLA-4 antibody of the Examples.

SEQ ID NO: 11 is the light chain variable region amino acid sequence of the murine CTLA-4 antibody used in the Examples.

SEQ ID NO: 12 is the heavy chain variable region amino acid sequence of the murine CTLA-4 antibody used in the Examples. SEQ ID NO: 13 is the complete heavy chain amino acid sequence of the murine CTLA-4 antibody used in the Examples.

SEQ ID NO: 14 is the amino acid sequence of the murine scFv CTLA-4 antibody of the Examples.

SEQ ID NO: 15 is the nucleotide sequence of the murine scFv CTLA-4 antibody of the Examples.

SEQ ID NO: 16 is the nucleotide sequence of the murine say CTLA-4 antibody of the Examples with inserted restriction sites for cloning purposes located at the N and C terminals, that is present in the exemplary virus. The restriction sites are the first six and last eight nucleotides of the sequence.

SEQ ID NO: 17 is the nucleotide sequence of the human scFv CTLA-4 antibody of the Examples with inserted restriction sites for cloning purposes located at the N and C terminals, that is present in the exemplary virus. The restriction sites are the first six and last eight nucleotides of the sequence.

SEQ ID NO: 18 is the nucleotide sequence of mouse GM-CSF.

SEQ ID NO: 19 is the nucleotide sequence of a codon optimized version of mouse GM-CSF.

SEQ ID NO: 20 is the nucleotide sequence of human GM-CSF.

SEQ ID NO: 21 is the nucleotide sequence of a codon optimized version of human GM-CSF.

SEQ ID NO: 22 is the amino acid sequence of mouse GM-CSF.

SEQ ID NO: 23 is the amino acid sequence of human GM-CSF.

SEQ ID NO: 24 is the nucleotide sequence of GALV-R-.

SEQ ID NO: 25 is the nucleotide sequence of a codon optimized version of GALV-R-.

SEQ ID NO: 26 is the amino acid sequence of GALV-R-.

SEQ ID NO: 27 is the nucleotide sequence of a codon optimized version of a human/mouse hybrid membrane bound version of CD40L.

SEQ ID NO: 28 is the amino acid sequence of a human/mouse hybrid membrane bound version of CD40L.

SEQ ID NO: 29 is the nucleotide sequence of a codon optimized version of a multimeric secreted version of human CD40L.

SEQ ID NO: 30 is the amino acid sequence of a multimeric secreted version of human CD40L.

SEQ ID NO: 31 is the nucleotide sequence of a codon optimized version of a multimeric secreted version of mouse CD40L.

SEQ ID NO: 32 is the amino acid sequence of a multimeric secreted version of mouse CD40L.

SEQ ID NO: 33 is the nucleotide sequence of wild-type human CD40L.

SEQ ID NO: 34 is the amino acid sequence of wild-type human CD40L.

SEQ ID NO: 35 is the nucleotide sequence of wild-type mouse CD40L.

SEQ ID NO: 36 is the amino acid sequence of wild-type mouse CD40L.

SEQ ID NO: 37 is the nucleotide sequence of the CMV promoter.

SEQ ID NO: 38 is the nucleotide sequence of the RSV promoter.

SEQ ID NO: 39 is the nucleotide sequence of BGH polyA.

SEQ ID NO: 40 is the nucleotide sequence of SV40 late polyA.

SEQ ID NO: 41 is the nucleotide sequence of rabbit beta-globulin polyA.

SEQ ID NO: 42 is the nucleotide sequence of GFP.

SEQ ID NO: 43 is the nucleotide sequence of retroviral LTR from MMLV.

SEQ ID NO: 44 is the nucleotide sequence of EF1a promoter.

SEQ ID NO: 45 is the nucleotide sequence of SV40 promoter.

SEQ ID NO: 46 is the nucleotide sequence of HGH polyA.

DETAILED DESCRIPTION OF THE INVENTION

Oncolytic Virus

The virus of the invention is oncolytic. An oncolytic virus is a virus that infects and replicates in tumor cells, such that the tumor cells are killed. Therefore, the virus of the invention is replication competent. Preferably, the virus is selectively replication competent in tumors. A virus is selectively replication competent in tumor tissue if it replicates more effectively in tumor tissue than in non-tumor tissue. The ability of a virus to replicate in different tissue types can be determined using standard techniques in the art.

The virus of the invention may be any virus which has these properties, including a herpes virus, pox virus, adenovirus, retrovirus, rhabdovirus, paramyxovirus or reovirus, or any species or strain within these larger groups. Viruses of the invention may be wild type (i.e. unaltered from the parental virus species), or with gene disruptions or gene additions. Which of these is the case will depend on the virus species to be used. Preferably the virus is a species of herpes virus, more preferably a strain of HSV, including strains of HSV1 and HSV2, and is most preferably a strain of HSV1. In particularly preferred embodiments the virus of the invention is based on a clinical isolate of the virus species to be used. The clinical isolate may have been selected on the basis of it having particular advantageous properties for the treatment of cancer.

The virus may be a modified clinical isolate, wherein the clinical isolate kills two or more tumor cell lines more rapidly and/or at a lower dose in vitro than one or more reference clinical isolate of the same species of virus. Typically, the clinical isolate will kill two or more tumor cell lines within 48 hours, preferably within 24 hours, of infection at multiplicities of infection (MOI) of less than or equal to 0.1. Preferably the clinical isolate will kill a broad range of tumor cell lines, such as 2, 3, 4, 5, 6, 7, 8, 9, 10 or, for example, all of the following human tumor cell lines: U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1(pancreas), HT1080 (fibrosarcoma).

In a preferred embodiment, the virus of the invention is a strain selected from:
  strain RH018A having the accession number ECCAC 16121904;
  strain RH004A having the accession number ECCAC 16121902;
  strain RH031A having the accession number ECCAC 16121907;
  strain RH040B having the accession number ECCAC 16121908;
  strain RH015A having the accession number ECCAC 16121903;
  strain RH021A having the accession number ECCAC 16121905;
  strain RH023A having the accession number ECCAC 16121906; and
  strain RH047A having the accession number ECCAC 16121909.

More preferably, the virus of the invention is a strain selected from:
  strain RH018A having the accession number ECCAC 16121904;
  strain RH004A having the accession number ECCAC 16121902;
  strain RH031A having the accession number ECCAC 16121907;
  strain RH040B having the accession number ECCAC 16121908; and
  strain RH015A having the accession number ECCAC 16121903.

Most preferably, the virus of the invention is strain RH018A having the accession number EACC 16121904. Any one of the deposited strains may be modified as defined herein.

An HSV of the invention is capable of replicating selectively in tumors, such as human tumors. Typically, the HSV replicates efficiently in target tumors but does not replicate efficiently in non-tumor tissue. This HSV may comprise one or more mutations in one or more viral genes that inhibit replication in normal tissue but still allow replication in tumors. The mutation may, for example, be a mutation that prevents the expression of functional ICP34.5, ICP6 and/or thymidine kinase by the HSV.

In one preferred embodiment, the ICP34.5-encoding genes are mutated to confer selective oncolytic activity on the HSV. Mutations of the ICP34.5-encoding genes that prevent the expression of functional ICP34.5 are described in Chou et al. (1990) Science 250:1262-1266, Maclean et al. (1991) J. Gen. Virol. 72:631-639 and Liu et al. (2003) Gene Therapy 10:292-303, which are incorporated herein by reference. The ICP6-encoding gene and/or thymidine kinase-encoding gene may also be inactivated, as may other genes provided that such inactivation does not prevent the virus infecting or replicating in tumors.

The HSV may contain a further mutation or mutations which enhance replication of the HSV in tumors. The resulting enhancement of viral replication in tumors not only results in improved direct 'oncolytic' tumor cell killing by the virus, but also enhances the level of heterologous (i.e. a gene inserted into the virus, in the case of viruses of the invention genes encoding a CTLA-4 inhibitor, GM-CSF and/or an immune co-stimulatory pathway activating molecule(s)) gene expression and increases the amount of tumor antigen released as tumor cells die, both of which may also improve the immunogenic properties of the therapy for the treatment of cancer. For example, in a preferred embodiment of the invention, deletion of the ICP47-encoding gene in a manner that places the US11 gene under the control of the immediate early promoter that normally controls expression of the ICP47 encoding gene leads to enhanced replication in tumors (see Liu et al., 2003, which is incorporated herein by reference).

Other mutations that place the US11 coding sequence, which is an HSV late gene, under the control of a promoter that is not dependent on viral replication may also be introduced into a virus of the invention. Such mutations allow expression of US11 before HSV replication occurs and enhance viral replication in tumors. In particular, such mutations enhance replication of an HSV lacking functional ICP34.5-encoding genes.

Accordingly, in one embodiment the HSV of the invention comprises a US11 gene operably linked to a promoter, wherein the activity of the promoter is not dependent on viral replication. The promoter may be an immediate early (IE) promoter or a non-HSV promoter which is active in mammalian, preferably human, tumor cells. The promoter may, for example, be a eukaryotic promoter, such as a promoter derived from the genome of a mammal, preferably a human. The promoter may be a ubiquitous promoter (such as a promoter of (3-actin or tubulin) or a cell-specific promoter, such as tumor-specific promoter. The promoter may be a viral promoter, such as the Moloney murine leukaemia virus long terminal repeat (MMLV LTR) promoter or the human or mouse cytomegalovirus (CMV) IE promoter. HSV immediate early (IE) promoters are well known in the art. The HSV IE promoter may be the promoter driving expression of ICP0, ICP4, ICP22, ICP27 or ICP47.

The genes referred to above, the functional inactivation of which provides the property of tumor selectivity to the virus, may be rendered functionally inactive by any suitable method, for example by deletion or substitution of all or part of the gene and/or control sequence of the gene or by insertion of one or more nucleic acids into or in place of the gene and/or the control sequence of the gene. For example, homologous recombination methods, which are standard in the art, may be used to generate the virus of the invention. Alternatively bacterial artificial chromosome (BAC)-based approaches may be used.

As used herein, the term "gene" is intended to mean the nucleotide sequence encoding a protein, i.e. the coding sequence of the gene. The various genes referred to above may be rendered non-functional by mutating the gene itself or the control sequences flanking the gene, for example the promoter sequence. Deletions may remove one or more portions of the gene, the entire gene or the entire gene and all or some of the control sequences. For example, deletion of only one nucleotide within the gene may be made, resulting in a frame shift. However, a larger deletion may be made, for example at least about 25%, more preferably at least about 50% of the total coding and/or non-coding sequence. In one preferred embodiment, the gene being rendered functionally inactive is deleted. For example, the entire gene and optionally some of the flanking sequences may be removed from the virus. Where two or more copies of the gene are present in the viral genome both copies of the gene are rendered functionally inactive.

A gene may be inactivated by substituting other sequences, for example by substituting all or part of the endogenous gene with a heterologous gene and optionally a promoter sequence. Where no promoter sequence is substituted, the heterologous gene may be inserted such that it is controlled by the promoter of the gene being rendered non-functional. In an HSV of the invention it is preferred that the ICP34.5 encoding-genes are rendered non-functional by the insertion of a heterologous gene or genes and a promoter sequence or sequences operably linked thereto, and optionally other regulatory elements such as polyadenylation sequences, into each the ICP34.5-encoding gene loci.

A virus of the invention is used to express a CTLA-4 inhibitor, and optionally GM-CSF and/or an immune co-stimulatory pathway activating molecule, in tumors. This is typically achieved by inserting a heterologous gene encoding a CTLA-4 inhibitor, and optionally a heterologous gene encoding GM-CSF and/or a heterologous gene encoding the immune co-stimulatory pathway activating molecule, in the genome of a selectively replication competent virus wherein each gene is under the control of a promoter sequence. As replication of such a virus will occur selectively in tumor tissue, expression of the CTLA-4 inhibitor and, if present, expression of the GM-CSF and/or the immune co-stimulatory activating protein by the virus, is also enhanced in tumor tissue as compared to non-tumor tissue in the body. Enhanced expression occurs where expression is greater in tumors as compared to other tissues of the body. Proteins expressed by the oncolytic virus would also be expected to be present in oncolytic virus-infected tumor draining lymph nodes, including due to trafficking of expressed protein and of virus in and on antigen presenting cells from the tumor. Accordingly, the invention provides benefits of expression of the CTLA-4 inhibitor and any co-expressed GM-CSF and/or immune co-stimulatory pathway activating molecule selectively in tumors and tumor draining lymph nodes combined with the anti-tumor effect provided by oncolytic virus replication.

The virus of the invention comprises a CTLA-4 inhibitor. The CTLA-4 inhibitor is a molecule, typically a peptide or protein that binds to CTLA-4 and reduces or blocks signaling through CTLA-4. By reducing CTLA-4 signalling, the inhibitor reduces or removes the block of immune stimulatory pathways by CTLA-4.

The CTLA-4 inhibitor is preferably an antibody or an antigen binding fragment thereof.

The term "antibody" as referred to herein includes whole antibodies and any antigen binding fragment (i.e., "antigen-binding portion") or single chains thereof. An antibody refers to a glycoprotein comprising at least two heavy (H) chains and two light (kappa)(L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

The antibody is typically a monoclonal antibody. The antibody may be a chimeric antibody. The antibody is preferably a humanised antibody and is more preferably a human antibody.

The term "antigen-binding fragment" of an antibody refers to one or more fragments of an antibody that retain the ability to specifically bind to CTLA-4. The antigen-binding fragment also retains the ability to inhibit CTLA-4 and hence to reduce or remove the CTLA-4 blockade of a stimulatory immune response. Examples of suitable fragments include a Fab fragment, a F(ab')₂ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. In a preferred embodiment, the antibody is an scFv. Examples of suitable scFv molecules are disclosed in, for example, WO2007/123737 and WO2014/066532, which are incorporated herein by reference.

The antibody encoding sequences typically encode an antibody or antibody fragment having a N-terminal signal sequence. The signal sequence may have the amino acid sequence shown in SEQ ID NO: 7. For example, this signal sequence is included in a scFv having the amino acid sequence shown in SEQ ID NO: 9 and encoded by the nucleotide sequence shown in SEQ ID NO: 10, and in a scFv having the amino acid sequence shown in SEQ ID NO: 14 and encoded by the nucleotide sequence shown in SEQ ID NO: 15.

In the antibody or antibody fragment, the light chain and heavy chain sequences may be joined by an amino acid linker. The linker typically comprises from about 15 to about 25 amino acids, such as about 18 or 20 amino acids. Any suitable linker may be used, such as linkers comprising glycine and serine residues, for example the amino acid sequence shown in SEQ ID NO: 8. For example, this linker is included in a scFv having the amino acid sequence shown in SEQ ID NO: 9 and encoded by the nucleotide sequence shown in SEQ ID NO: 10, and in a scFv having the amino acid sequence shown in SEQ ID NO: 14 and encoded by the nucleotide sequence shown in SEQ ID NO: 15. Both are preferred antibody fragments for use in the invention.

Other antibody fragments having similar structures are also preferred. Accordingly the virus of the invention may encode an antibody or fragment comprising, or consisting essentially of, a light chain variable region, a linker a heavy chain variable region, a heavy chain CH1 domain, a heavy chain CH2 domain and a heavy chain CH3 domain. The virus may further encode a signal sequence at the N-terminus of the antibody.

The antibodies or antibody fragments of the invention may preferably comprise an Fc region which is an IgG1, IgG2, IgG3 or IgG4 region, more preferably an IgG1 region. Preferably, the antibody is an scFv antibody in which the scFv is linked to IgG heavy chain CH2 and CH3 domains.

A preferred CTLA-4 antibody or fragment comprises the heavy chain variable region shown in SEQ ID NO:3 and/or the light chain variable region shown in SEQ ID NO: 1 or the heavy chain variable region shown in SEQ ID NO:11 and/or the light chain variable region shown in SEQ ID NO: 12. The antibody may comprise the heavy chain CH1 domain having the amino acid sequence shown in SEQ ID NO: 4 and/or the CH2/CH3 domains shown in SEQ ID NO: 5. The antibody may comprise the light chain amino acid sequence shown in SEQ ID NO: 2. An antibody of the invention may alternatively comprise a variant of one of these heavy or light chain variable regions or CDR sequences. For example, a variant may be a substitution, deletion or addition variant of any of the above amino acid sequences.

A variant antibody may comprise 1, 2, 3, 4, 5, up to 10, up to 20, up to 30 or more amino acid substitutions and/or deletions from the specific sequences and fragments discussed above, whilst maintaining the activity of the antibodies described herein. "Deletion" variants may comprise the deletion of, for example, 1, 2, 3, 4 or 5 individual amino acids or of one or more small groups of amino acids such as 2, 3, 4 or 5 amino acids. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid.

The virus of the invention comprises one or more polynucleotide sequence encoding the CTLA-4 inhibitor. The polynucleotide sequence is under the control of a suitable promoter. The virus may comprise a first polynucleotide sequence encoding an antibody heavy chain variable region and a second polynucleotide encoding an antibody light chain variable region. The first polynucleotide may encode a full length heavy chain and/or the second polynucleotide may encode a full length light chain. The first and second polynucleotide may be under the control of a single promoter, optionally with an IRES, or may be under the control of two separate promoters. The separates promoters may be the same or different.

The first polynucleotide may comprise, consist essentially of or consist of the heavy chain variable region encoding sequence shown in SEQ ID NO: 9 and/or the second polynucleotide may comprise, consist essentially of or consist of the heavy chain variable region encoding sequence shown in SEQ ID NO: 10. The first polynucleotide may comprise, consist essentially of or consist of the heavy chain variable region encoding sequence shown in SEQ ID NO: 19 and/or the second polynucleotide may comprise, consist essentially of or consist of the heavy chain variable region encoding sequence shown in SEQ ID NO: 20.

A first and/or second polynucleotide sequences may be a variant of SEQ ID NO: 9, 10, 19 or 20. For example, a variant may be a substitution, deletion or addition variant of either of these nucleic acid sequences. A variant polynucleotide may comprise 1, 2, 3, 4, 5, up to 10, up to 20, up to 30, up to 40, up to 50, up to 75 or more nucleic acid substitutions and/or deletions from SEQ ID NO: 9, 10, 19 or 20.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids. The codons may be optimized so as to increase expression levels of the encoded proteins in target cells as compared to if the unaltered sequence is used.

The virus of the invention preferably comprises GM-CSF. The sequence of the gene encoding GM-CSF may be codon optimized so as to increase expression levels of the respective proteins in target cells as compared to if the unaltered sequence is used.

The virus of the invention preferably comprises one or more immune co-stimulatory pathway activating molecules and/or one or more genes encoding an immune co-stimulatory pathway activating molecule Immune co-stimulatory pathway activating molecules include proteins and nucleic acid molecules (e.g. aptamer sequences). Examples of immune co-stimulatory pathway activating molecules include CD40 ligand, GITR ligand, 4-1-BB ligand, OX40 ligand, ICOS ligand, flt3 ligand, TL1A, CD30 ligand, CD70 and single chain antibodies targeting the respective receptors for these molecules (CD40, GITR, 4-1-BB, OX40, ICOS, flt3, DR3, CD30, CD27).

Activators of immune co-stimulatory pathway include mutant or wild type, soluble, secreted and/or membrane bound ligands, and agonistic antibodies including single chain antibodies. Viruses of the invention preferably encode one or more of CD40L, ICOSL, 4-1-BBL, GITRL or OX40L.

Viruses of the invention may encode one or more immune co-stimulatory pathway activating molecules, preferably 1, 2, 3 or 4 immune co-stimulatory pathway activating molecules, more preferably 1 or 2 immune co-stimulatory pathway activating molecules.

The sequence of the gene encoding the immune co-stimulatory activating molecule may be codon optimized so as to increase expression levels of the respective protein(s) in target cells as compared to if the unaltered sequence is used.

The virus of the invention may comprise one or more further heterologous genes in addition to a CTLA-4 inhibitor, and GM-CSF and/or an immune co-stimulatory pathway activating molecule. In a preferred embodiment, the virus may further comprise a fusogenic protein such as GALVR-.

The fusogenic protein may be any heterologous protein capable of promoting fusion of a cell infected with the virus of the invention to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoproteins include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R-versions). In a preferred embodiment the fusogenic protein is from GALV and has the R-peptide removed (GALV-R-).

The virus of the invention may optionally comprise multiple copies of the fusogenic protein-encoding gene, preferably 1 or 2 copies. The virus may comprise two or more different fusogenic proteins, including any of the fusogenic proteins listed above.

The fusogenic protein or proteins optionally expressed by a virus of the invention may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic properties of the encoded protein, or to provide codon optimisation and therefore increase the efficiency of expression of the encoded protein.

The invention also provides a virus, such as a pox virus or a HSV, preferably HSV1, which expresses at least three heterologous genes, wherein each of the three heterologous genes is driven by a different promoter selected from the CMV promoter, the RSV promoter, the EF1a promoter, the SV40 promoter and a retroviral LTR promoter. The virus may, for example, express four heterologous genes, wherein each of the four heterologous genes is driven by a different promoter selected from the CMV promoter, the RSV promoter, the EF1a promoter, the SV40 promoter and a retroviral LTR promoter. The retroviral LTR is preferably from MMLV. The heterologous genes may be terminated by polyadenylation sequences. The polyadenylation sequences may be the same or different. Preferably each heterologous gene is terminated by a different polyadenylation sequence, which is preferably selected from the BGH, SV40, HGH and RBG polyadenylation sequences. The invention also provides a virus, such as a pox virus or a HSV, preferably HSV1, which expresses at least three heterologous genes, wherein each of the three heterologous genes is terminated by a different polyadenylation sequence selected from the BGH, SV40, HGH and RBG polyadenylation sequences. The virus may, for example, express four heterologous genes terminated by each of the BGH, SV40, HGH and RBG polyadenylation sequences, respectively.

The at least three heterologous genes may, for example, be selected from a CTLA-4 inhibitor, a gene encoding GM-CSF, a gene encoding an immune co-stimulatory pathway activating molecule and a fusogenic gene. Examples of the three heterologous genes are a CTLA-4 inhibitor, a gene encoding GM-CSF and a gene encoding an immune co-stimulatory pathway activating molecule; a CTLA-4 inhibitor, a gene encoding GM-CSF and a fusogenic gene; and a CTLA-4 inhibitor, a gene encoding an immune co-stimulatory pathway activating molecule and a fusogenic gene. The four heterologous genes may, for example, be a CTLA-4 inhibitor, a gene encoding GM-CSF, a gene encoding an immune co-stimulatory pathway activating molecule and a fusogenic gene. The three or four heterologous genes may comprise, for example, two ore more genes encoding immune co-stimulatory pathway activating molecules and/or two ore more fusogenic genes.

In one embodiment, the promoters controlling expression of the three heterologous genes are the CMV, RSV and MMLV promoters. For example, a preferred virus may comprise a GM-CSF gene under the control of a CMV promoter, a GALV gene under the control of a RSV promoter and a CTLA-4 inhibitor under the control of a MMLV promoter.

In one embodiment, the polyadenylation sequence terminating the at least three heterologous genes are SV40, BGH and RBG polyadenylation sequences. controlling expression of the three heterologous genes are the CMV, RSV and MMLV promoters. For example, a preferred virus may comprise a GM-CSF gene terminated by a BGH polyadenylation sequence, a GALV gene terminated by a SV40 polyadenylation sequence and a CTLA-4 inhibitor terminated by a RGB polyadenylation sequence.

Any combination of the various promoters and polyadenylation sequences may be used with any of the heterologous genes. For example, a preferred virus may comprise a GM-CSF gene under the control of a CMV promoter and terminated by a BGH polyadenylation sequence, a GALV gene under the control of a RSV promoter and terminated by a SV40 polyadenylation sequence, and a CTLA-4 inhibitor under the control of a MMLV promoter terminated by a RGB polyadenylation sequence.

Production of Virus

Viruses of the invention are constructed using methods well known in the art. For example plasmids (for smaller viruses and single and multiple genome component RNA viruses) or BACs (for larger DNA viruses including herpes viruses) encoding the viral genome to be packaged, including the genes encoding the fusogenic and immune stimulating molecules under appropriate regulatory control, can be constructed by standard molecular biology techniques and transfected into permissive cells from which recombinant viruses can be recovered.

Alternatively, in a preferred embodiment plasmids containing DNA regions flanking the intended site of insertion can be constructed, and then co-transfected into permissive cells with viral genomic DNA such that homologous recombination between the target insertion site flanking regions in the plasmid and the same regions in the parental virus occur. Recombinant viruses can then be selected and purified through the loss or addition of a function inserted or deleted by the plasmid used for modification, e.g. insertion or deletion of a marker gene such as GFP or lacZ from the parental virus at the intended insertion site. In a most preferred embodiment the insertion site is the ICP34.5 locus of HSV, and therefore the plasmid used for manipulation contains HSV sequences flanking this insertion site, between which are an expression cassette encoding GM-CSF and the immune co-stimulatory pathway activating molecule. In this case, the parental virus may contain a cassette encoding GFP in place of ICP34.5 and recombinant virus plaques are selected through the loss of expression of GFP. In a most preferred embodiment the US11 gene of HSV is also expressed as an IE gene. This may be accomplished through deletion of the ICP47-encoding region, or by other means.

The CTLA-4 inhibitor, and optionally the GM-CSF encoding sequences and immune co-stimulatory pathway activating molecule encoding sequences and/or additional protein encoding sequence, such as a sequence encoding a fusogenic protein such as GALVR-, are inserted into the viral genome under appropriate regulatory control. This may be under the regulatory control of natural promoters of the virus species of the invention used, depending on the species and insertion site, or preferably under the control of heterologous promoters. Suitable heterologous promoters include mammalian promoters, such as the IEF2a promoter or the actin promoter. More preferred are strong viral promoters such as the CMV IE promoter, the RSV LTR, the MMLV LTR, other retroviral LTR promoters, or promoters derived from SV40. Preferably each exogenous gene (e.g. encoding the GM-CSF and immune co-stimulatory pathway activating molecule) will be under separate promoter control, but may also be expressed from a single RNA transcript, for example through insertion of an internal ribosome entry sites (IRES) between protein coding sequences. RNA derived from each promoter is typically terminated using a polyadenylation sequence (e.g. mammalian sequences such as the bovine or human growth hormone (BGH) poly A sequence, synthetic polyadenylation sequences, the rabbit betaglobin polyadenylation sequence, or viral sequences such as the SV40 early or late polyadenylation sequence).

Each of the heterologous genes in the virus is typically under the control of a promoter. The promoters controlling expression of the heterologous genes may be the same or different. For example, the anti-CTLA-4, and one or more of the GM-CSF, fusogenic gene and immune co-stimulatory pathway activating molecule-encoding gene may each be under the control of the CMV promoter, the RSV promoter, the EF1a promoter, the SV40 promoter or a retroviral LTR promoter. Alternatively, for example, the anti-CTLA-4 may be under the control of a retroviral LTR promoter such as the MMLV promoter, the GM-CSF gene may be under the control of the CMV promoter and/or the fusogenic gene, such as GALVR- may be under the control of the RSV promoter.

Pharmaceutical Compositions

The invention provides a pharmaceutical composition comprising the virus and a pharmaceutically acceptable carrier or diluent. Suitable carriers and diluents include isotonic saline solutions, for example phosphate-buffered saline. The composition may further comprise other constituents such as sugars or proteins to improve properties such as stability of the product. Alternatively a lyophilized formulation may be used, which is reconstituted in a pharmaceutically acceptable carrier or diluent before use.

The choice of carrier, if required, is frequently a function of the route of delivery of the composition. Within this invention, compositions may be formulated for any suitable route and means of administration. Pharmaceutically acceptable carriers or diluents are those used in compositions suitable for intra-tumoral administration, intravenous/intraarterial administration, administration into the brain or administration into a body cavity (e.g. bladder, pleural cavity or by intraperitoneal administration). The composition may be administered in any suitable form, preferably as a liquid.

The present invention also provides a product of manufacture comprising a virus of the invention in a sterile vial, ampoule or syringe.

Medical Uses/Methods of Treatment

The invention provides the virus of the invention for use in the treatment of the human or animal body by therapy, particularly for use in a method of treating cancer. The cancer is typically in a mammal, preferably in a human. The virus kills infected tumour cells by lysis and by causing infected tumor cells to fuse with one another. The virus of the invention also elicits a systemic anti-tumor immune response, augmented through the expression of the CTLA-4 inhibitor, and optionally GM-CSF and the immune co-stimulatory pathway activating molecule, which also kills cancer cells.

The invention also provides a method of treating cancer, the method comprising administering a therapeutically effective amount of the virus of the invention to an individual in need thereof.

The invention additionally provides the use of the virus of the invention in the manufacture of a medicament for treating cancer.

The virus of the invention is particularly useful in treating any solid tumor including any adenocarcinoma, carcinoma, melanoma or sarcoma. For example, the virus of the invention is useful in treating head and neck, prostate, breast, ovarian, lung, liver, endometrial, bladder, gall bladder, pancreas, colon, kidney, stomach/gastric, esophageal, or cervical cancers, mesothelioma, melanoma or other skin cancer, lymphoma, glioma or other cancer of the nervous system, or sarcomas such as soft tissue sarcoma.

The virus of the invention may be used to treat malignant tumors, including tumors that have metastasised from the site of the original tumor. In this embodiment, the virus may be administered to the primary tumor or to one or more secondary tumors.

The virus of the invention may be administered in combination with other therapeutic agents, including chemotherapy, targeted therapy, immunotherapy (including immune checkpoint blockade, i.e. administration of one or more antagonist of an immune co-inhibitory pathway, and/or one or more agonist of an immune co-stimulatory pathway) and/or in combination with radiotherapy and/or in combination with any combination of these. The therapeutic agent is preferably an anti-cancer agent.

The virus of the invention may be administered in combination with a second virus, such as a second oncolytic virus.

For example, the therapeutic agent may comprise an immunogen (including a recombinant or naturally occurring antigen, including such an antigen or combination of antigens delivered as DNA or RNA in which it/they are encoded), to further stimulate an immune response, such as a cellular or humoral immune response, to tumor cells, particularly tumor neoantigens. The therapeutic agent may be an agent intended to increase or potentiate an immune response, such as a cytokine, an agent intended to inhibit an immune checkpoint pathway or stimulate an immune potentiating pathway or an agent which inhibits the activity of regulatory T cells (Tregs) or myeloid derived suppressor cells (MDSCs).

The therapeutic agent may be an agent known for use in an existing cancer therapeutic treatment. The therapeutic agent may be radiotherapy or a chemotherapeutic agent. The therapeutic agent may be selected from cyclophosmamide, alkylating-like agents such as cisplatin or melphalan, plant alkaloids and terpenoids such as vincristine or paclitaxel (Taxol), antimetabolites such as 5-fluorouracil, topoisomerase inhibitors type I or II such as camptothecin or doxorubicin, cytotoxic antibiotics such as actinomycin, anthracyclines such as epirubicin, glucocorticoids such as triamcinolone, inhibitors of protein, DNA and/or RNA synthesis such as methotrexate and dacarbaxine, histone deacetylase (HDAC) inhibitors, or any other chemotherapy agent.

The therapeutic agent may be one, or a combination of: immunotherapeutics or immunomodulators, such as TLR agonists; agents that down-regulate T-regulatory cells such as cyclophosphamide; or agents designed to block immune checkpoints or stimulate immune potentiating pathways, including but not limited to monoclonal antibodies, such as a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a GITR agonist, a 4-1-BB agonist, a KIR inhibitor, a SLAMF7 inhibitor, an OX40 agonist, a CD40 agonist, an ICOS agonist or a CD47 inhibitor. In a preferred embodiment, the therapeutic agent is a CTLA-4 inhibitor such as an anti-CTLA-4 antibody, a PD1 inhibitor, such as an anti-PD-1 antibody or a PD-L1 inhibitor such as an anti-PD-L1 antibody. Such inhibitors, agonists and antibodies can be generated and tested by standard methods known in the art.

Immunotherapeutic agents may also include bi-specific antibodies, cell based-therapies based on dendritic cells, NK cells or engineered T cells such CAR-T cells or T cells expressing engineered T cell receptors. Immunotherapeutic agents also include agents that target a specific genetic mutation which occurs in tumors, agents intended to induce immune responses to specific tumor antigens or combinations of tumor antigens, including neoantigens and/or agents intended to activate the STING/cGAS pathway, TLR or other innate immune response and/or inflammatory pathway, including intra-tumoral agents.

For example, a virus of the invention may be used: in combination with dacarbazine, a BRAF inhibitor and/or PD1 or PD-L1 blockade to treat melanoma; in combination with taxol, doxorubicin, vinorelbine, cyclophosphamide and/or gemcitabine to treat breast cancer; in combination with 5-fluorouracil and optionally leucovorin, irinoteacan and/or oxaliplatin to treat colorectal cancer; in combination with taxol, carboplatin, vinorelbine and/or gemcitabine, PD-1 or PD-L1 blockade to treat lung cancer; in combination with cisplatin and/or radiotherapy to treat head and neck cancer.

The therapeutic agent may be an inhibitor of the idoleamine 2,3-dioxygenase (IDO) pathway. Examples of IDO inhibitors include epacadostat (INCB024360), 1-methyl-tryptophan, indoximod (1-methyly-D-tryptophan), GDC-0919 or F001287.

The mechanism of action of IDO in suppressing anti-tumor immune responses may also suppress immune responses generated following oncolytic virus therapy. IDO expression is induced by toll like receptor (TLR) activation and interferon-γ both of which may result from oncolytic virus infection. One embodiment of the use of oncolytic virus therapy for cancer treatment includes combination of an oncolytic virus, including a virus expressing a CTLA-4 inhibitor, and optionally GM-CSF and/or an immune co-stimulatory pathway activating molecule or molecules and/or one or more additional protein encoding sequences, such as a sequence encoding a fusogenic protein such as GALVR-, with an inhibitor of the IDO pathway and optionally a further antagonist of an immune co-inhibitory pathway and/or one or more agonist of an immune co-stimulatory pathway, including those targeting PD-1 and/or PD-L1.

Where a therapeutic agent and/or radiotherapy is used in conjunction with a virus of the invention, administration of the virus and the therapeutic agent and/or radiotherapy may be contemporaneous or separated by time. The composition of the invention may be administered before, together with or after the therapeutic agent or radiotherapy. The method of treating cancer may comprise multiple administrations of the virus of the invention and/or of the therapeutic agent and/or radiotherapy. In preferred embodiments, in the case of combination with immune checkpoint blockade or other immune potentiating agents, the virus of the invention is administered once or multiple times prior to the concurrent administration of the immune checkpoint blockade or other immune potentiating agent or agents thereafter, or concurrent with the administration of the immune checkpoint blockade or other immune potentiating agent or agents without prior administration of the virus of the invention.

The virus of the invention may be administered to a subject by any suitable route. Typically, a virus of the invention is administered by direct intra-tumoral injection. Intra-tumoral injection includes direct injection into superficial skin, subcutaneous or nodal tumors, and imaging guided (including CT, MRI or ultrasound) injection into deeper or harder to localize deposits including in visceral organs and elsewhere. The virus may be administered into a body cavity, for example into the pleural cavity, bladder or by intra-peritoneal administration. The virus may be injected into a blood vessel, preferably a blood vessel supplying a tumor.

Therapeutic agents which may be combined with a virus of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In preferred embodiments, the compositions are administered by intravenous infusion, orally, or directly into a tumor.

The virus and/or therapeutic agent may be administered to a subject in an amount that is compatible with the dosage composition that will be therapeutically effective. The administration of the virus of the invention is for a "therapeutic" purpose. As used herein, the term "therapeutic" or "treatment" includes any one or more of the following as its objective: the prevention of any metastasis or further metastasis occurring; the reduction or elimination of symptoms; the reduction or complete elimination of a tumor or cancer, an increase in the time to progression of the patient's cancer; an increase in time to relapse following treatment; or an increase in survival time.

Therapeutic treatment may be given to Stage I, II, III, or IV cancers, preferably Stage II, III or IV, more preferably Stage III or IV, pre- or post-surgical intervention (i.e. following recurrence or incomplete removal of tumors following surgery), preferably before any surgical intervention (either for resection of primary or recurrent/metastatic disease), or following recurrence following surgery or following incomplete surgical removal of disease, i.e. while residual tumor remains.

Therapeutic treatment may be carried out following direct injection of the virus composition into target tissue which may be the tumor, into a body cavity, or a blood vessel. As a guide, the amount of virus administered is in the case of HSV in the range of from $10^4$ to $10^{10}$ pfu, preferably from $10^5$ to $10^9$ pfu. In the case of HSV, an initial lower dose (e.g. $10^4$ to $10^7$ pfu) may be given to patients to seroconvert patients who are seronegative for HSV and boost immunity in those who are seropositive, followed by a higher dose then being given thereafter (e.g. $10^6$ to $10^9$ pfu). Typically up to 20 ml of a pharmaceutical composition consisting essentially of the virus and a pharmaceutically acceptable suitable carrier or diluent may be used for direct injection into tumors, or up to 50 ml for administration into a body cavity (which may be subject to further dilution into an appropriate diluent before administration) or into the bloodstream. However for some oncolytic therapy applications larger or smaller volumes may also be used, depending on the tumor and the administration route and site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor or into a body cavity. The virus may also be administered by injection into a blood vessel. The optimum route of administration will depend on the location and size of the tumor. Multiple doses may be required to achieve an immunological or clinical effect, which, if required, will be typically administered between 2 days to 12 weeks apart, preferably 3-days to 3 weeks apart. Repeat doses up to 5 years or more may be given, preferably for up to one month to two years dependent on the speed of response of the tumor type being treated and the response of a particular patient, and any combination therapy which may also be being given.

The following Examples illustrate the invention,

Example 1. Construction of a Virus of the Invention

Figure 1B:
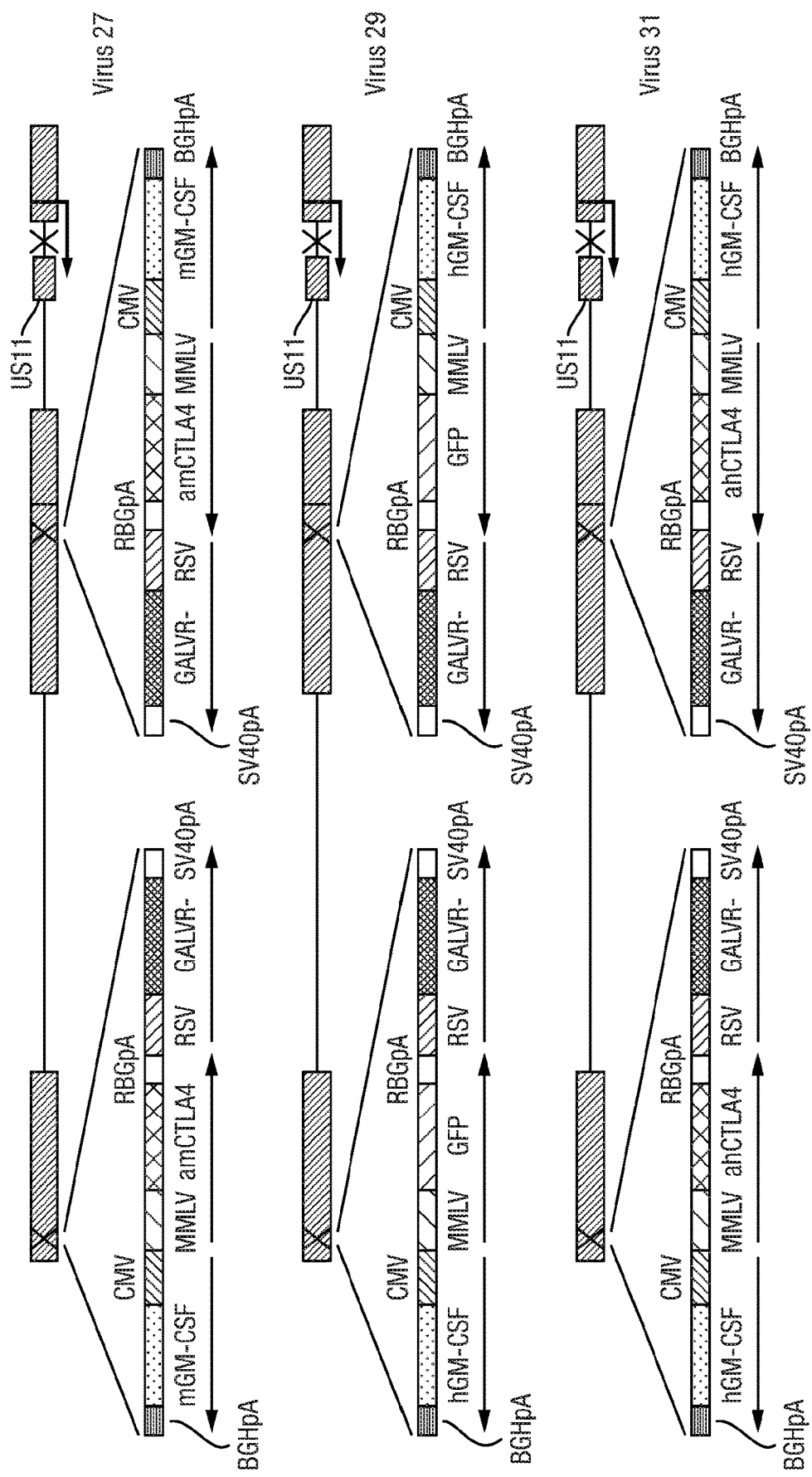
Figure 2B:
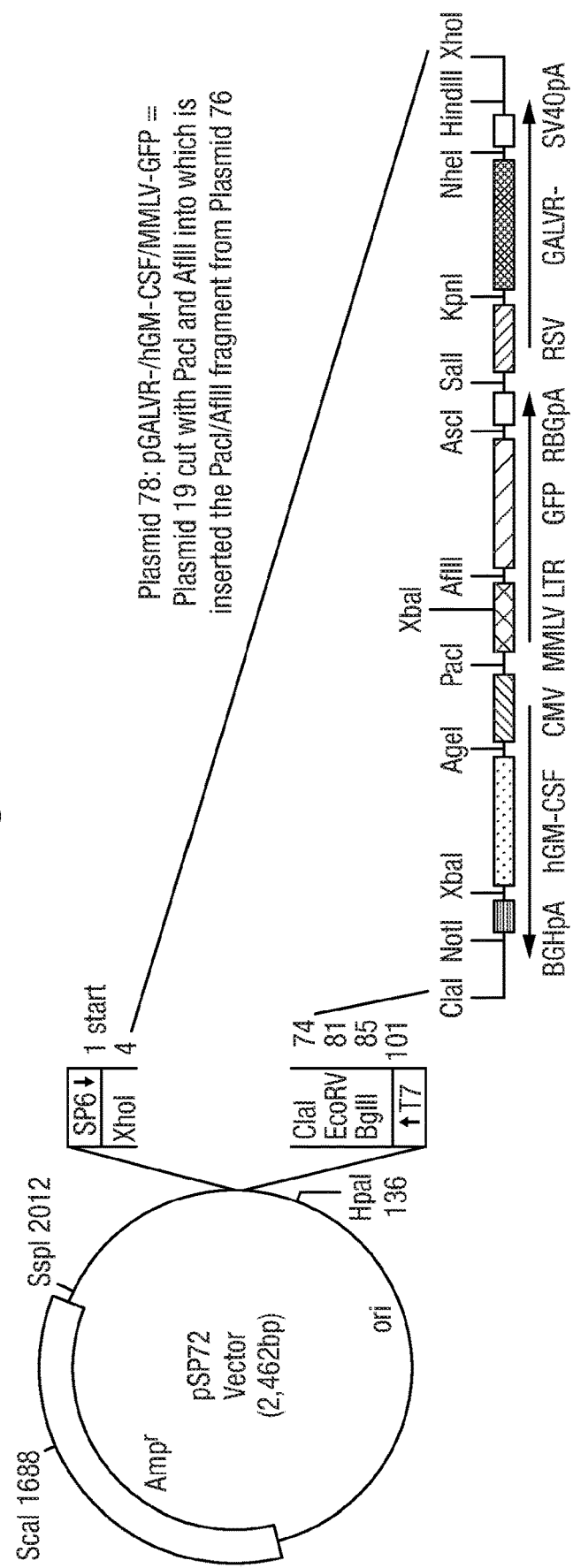
FIG. 2 depicts the structures of the plasmids used to construct the exemplary viruses of the invention.
Figure 2C:
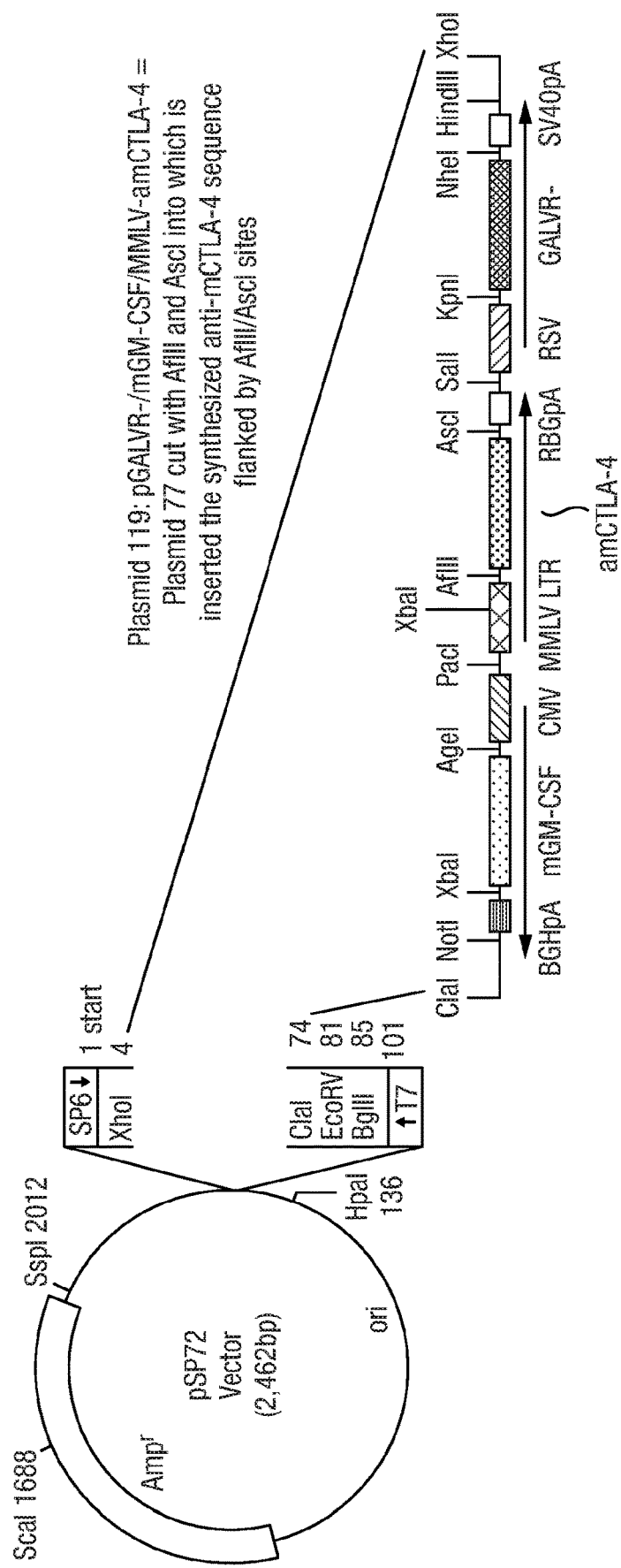
Figure 2D:
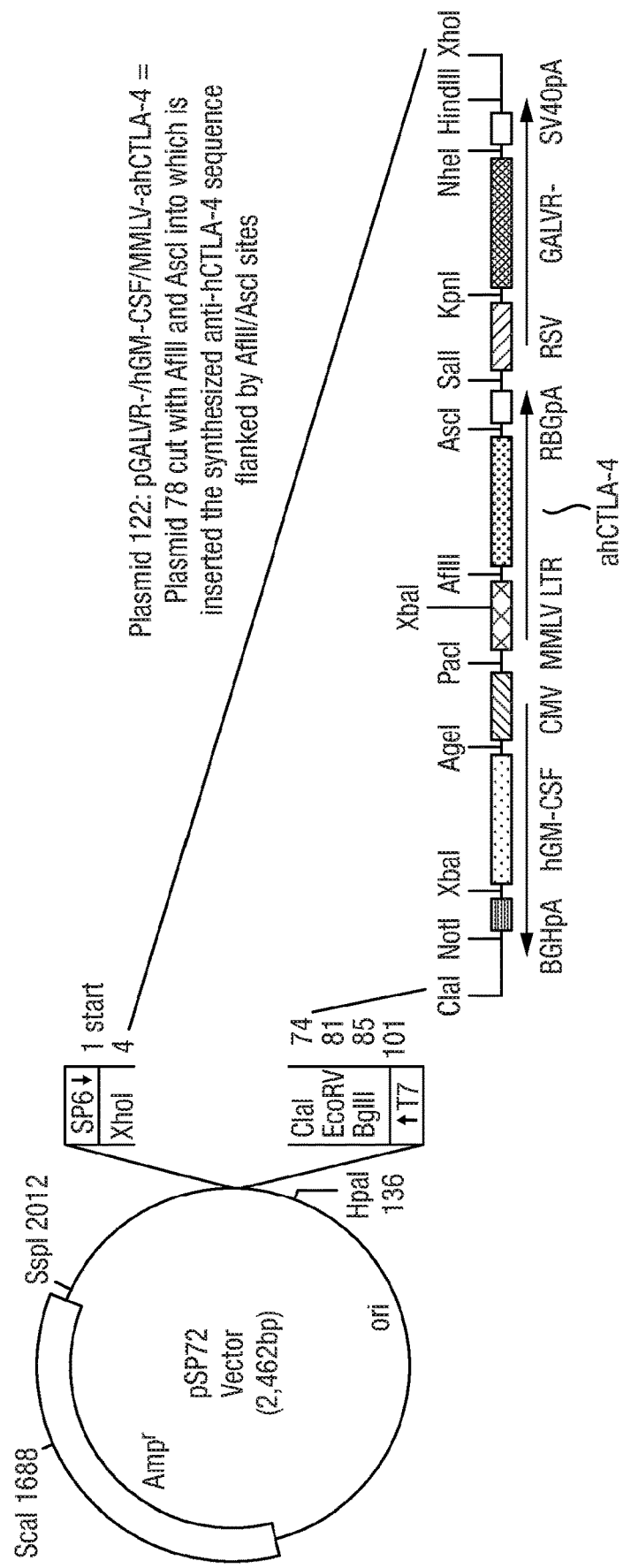
Figure 3:
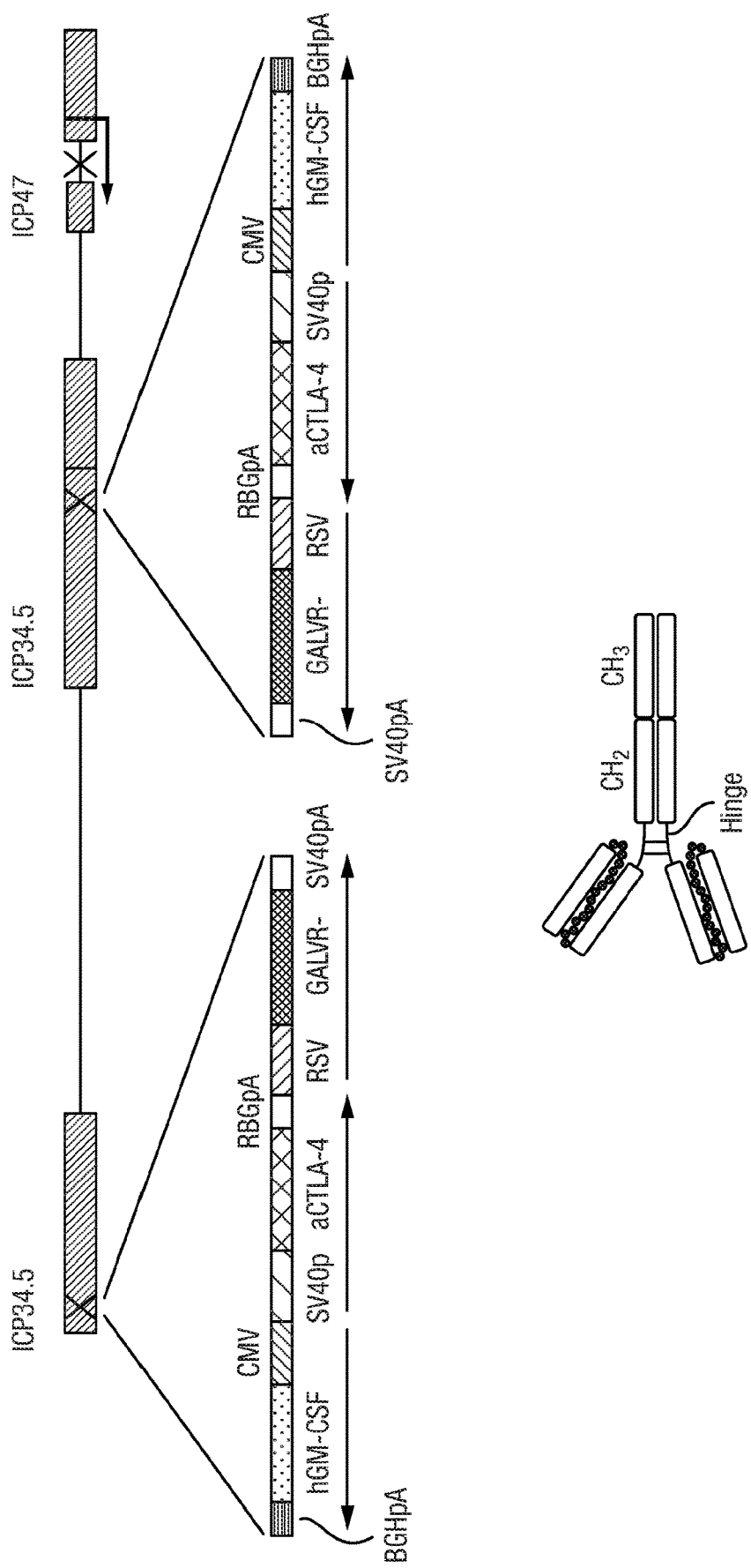
FIG. 3 shows the structure of anti-mouse or human CTLA-4 constructs that are codon optimized secreted scFv molecules linked to human or mouse IgG1 Fc regions. The scFvs contain the linked ($[G_4S]_3$) light and heavy variable chains from 9D9 (the initial mouse antibody initially used to validate CTLA-4; US2011044953: mouse version) or from ipilimumab (US20150283234; human version). The resulting structure of the CTLA-4 inhibitor is also shown.

The virus species used to exemplify the invention is HSV, specifically HSV1,

Diagrams of the plasmids used are shown in FIG. 2, Diagrams of the viruses are shown in FIG. 1. All viruses were constructed using HSV1 Strain RH018A, The plasmids used for virus construction were generated by a combination of gene synthesis and subcloning, conducted by Genscript Inc.

Viruses expressing anti-mouse CTLA4 together with mouse GM-CSF and GAIN were constructed by co-transfection of Plasmid 77 with Virus 16 DNA, so as to insert GFP into Virus 16 by selection of plaques expressing MT to give Virus 25. GFP was then knocked out of Virus 25 by co-transfection of Virus 25 DNA with Plasmid 119. This gave Virus 27.

Viruses expressing anti-human CTLA4 together with human GM-CSF and GALV were constructed by co-transfection of Plasmid 78 with Virus 17 DNA, so as to insert GFP into Virus 17 by selection of plaques expressing GFP to give Virus 29. GFP was then knocked out of Virus 29 by co-transfection of Virus 29 DNA with Plasmid 122. This gave Virus 31.

Viruses expressing anti-mouse CTLA-4 and co-stimulatory ligands together with mouse GM-CST and GAIN were constructed by co-transfection of a plasmid encoding GFP driven by an SV40 promoter between the mouse GM-CSF and anti-mouse CTLA-4 encoding sequences with Virus 27. GFP was then knocked out of the resulting virus with a plasmid enoding each of the individual mouse co-stimulatory ligands in place of CFP, Viruses expressing anti-human CTLA-4 and co-stimulatory ligands together with human GM-CSF and GAIN were constructed by co-transfection of a plasmid encoding GFP driven by an SV40 promoter between the human GM-CSF and anti-human CTLA-4 encoding sequences with Virus 31. GFP was then knocked out of the resulting virus with a plasmid encoding each of the individual human co-stimulator ligands in place of GFP.

Figure 4:
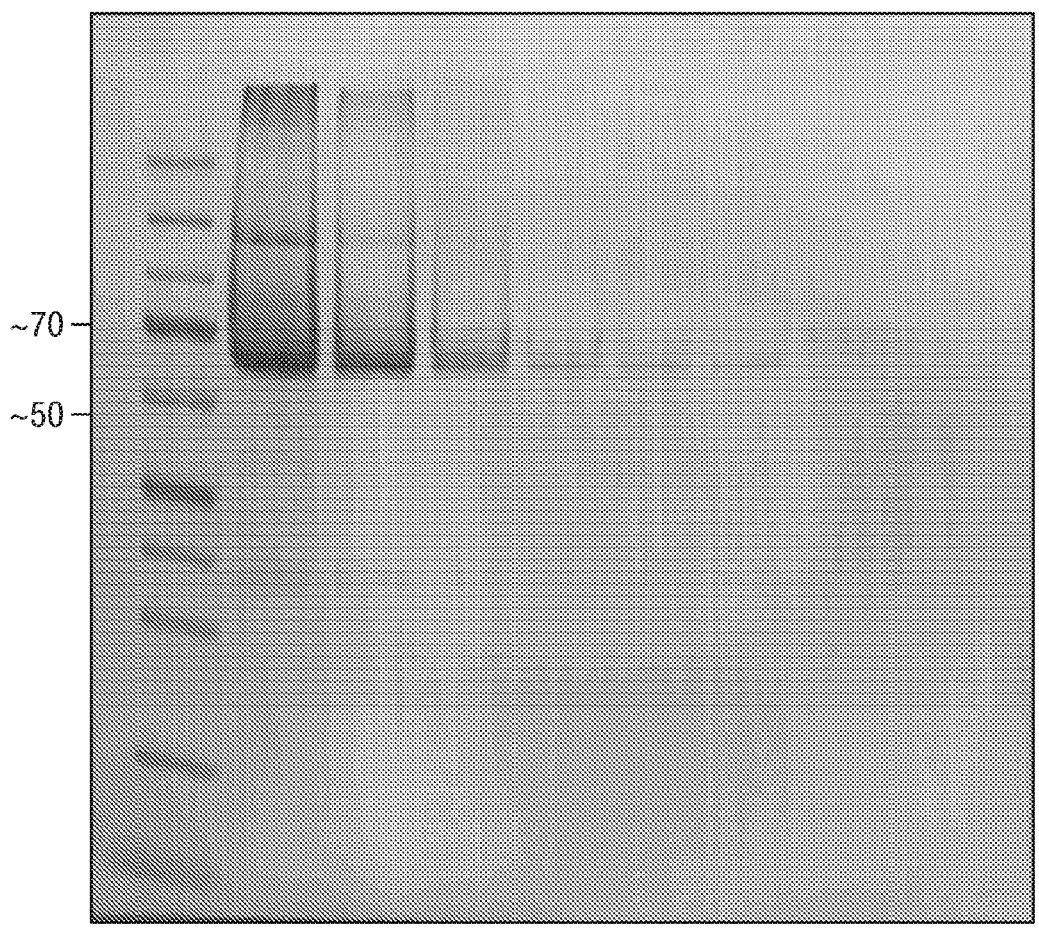
FIG. 4 is a western blot demonstrating that anti-mouse CTLA-4 is expressed from virus 27. The gel used was a reduced denatured PVDF membrane tris-glycine gel. Anti-CTLA-4 was detected using an alkaline phosphatase-tagged anti-mouse IgG1 antibody. Lane 1: spectra broad range ladder; lane 2 virus 27 neat supernatant; lane 3 virus 27 supernatant diluted 1 in 2; lane 4 virus 27 supernatant diluted 1 in 4; lane 5 virus 27 supernatant diluted 1 in 8; lane 6 virus 27 supernatant diluted 1 in 16; lane 7 virus 27 supernatant diluted 1 in 32; lane 8 negative control virus (neat supernatant). The expected size of anti-CTLA-4 (reduced) is 57 kDa.

FIG. 4 shows a western blot demonstrating expression of anti-mouse CTLA-4 from Virus 27.

Example 2. The Effect of Combined Expression of GALV, GM-CSF and Anti-CTLA4 from an Oncolytic Virus The utility of the invention is demonstrated in the following way, A20 cells are administered into both flanks of Balb/c mice and the A20 tumors are allowed to grow to approximately 0.5 cm in diameter.

Figure 5:
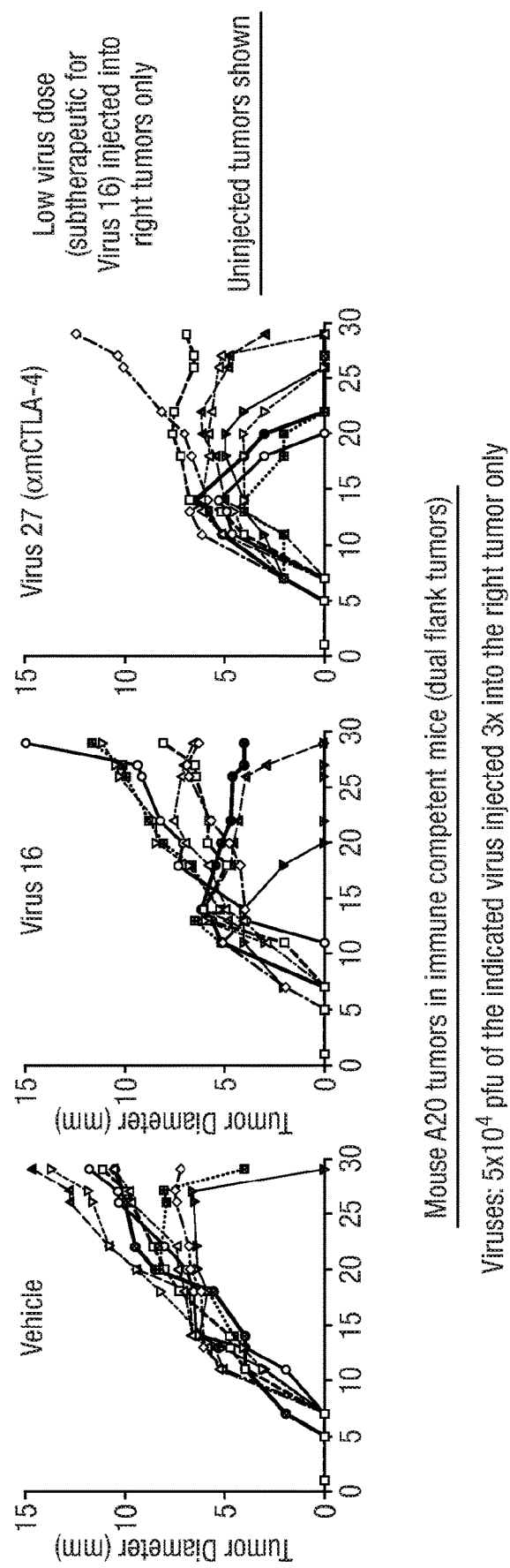
FIG. 5 shows the superior tumor control and shrinkage in uninjected tumors of a virus expressing anti-mCTLA-4 (virus 27) compared to an otherwise identical virus that does not express CTLA-4 (virus 16). The dose of virus used was $5 \times 10^4$ pfu (50 of $1 \times 10^6$ pfu/ml in each case), given three times over one week. This dose level of virus is subtherapeutic for uninjected tumors for virus 16, which allows the benefits of the delivery of the additional molecule encoded by virus 27 to clearly be seen.
Figure 6:
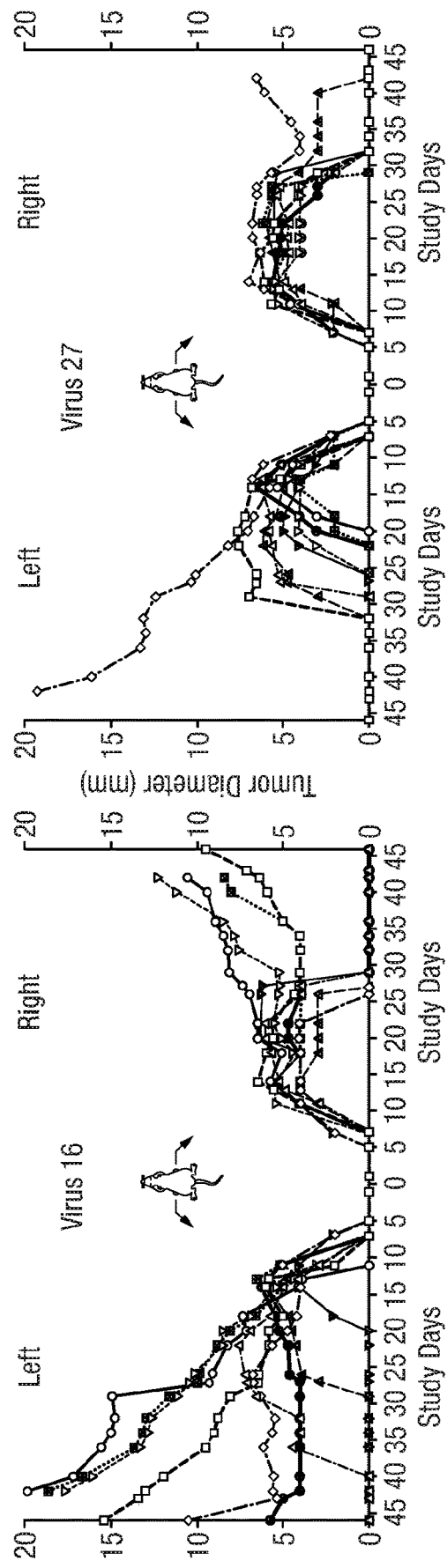
FIG. 6 shows the superior tumor control and shrinkage in both injected and uninjected tumors of a virus expressing anti-mCTLA-4 (virus 27) compared to an otherwise identical virus that does not express CTLA-4 (virus 16). The dose of the virus used was $5 \times 10^4$ pfu over one week into the right tumor of a virus expressing anti-mCTLA-4 (virus 27) compared to an otherwise identical virus that does not express CTLA-4 (virus 16). Each line represents a different mouse.

The following treatments are then administered to groups of mice, into one flank of each mouse only (right tumor) 3 times per week for one week:
  50 µl of vehicle (1 group);
  50 µl of $10^6$ pfu/ml of the HSV with only mouse GM-CSF and GALVR- inserted (Virus 16);
  50 µl of $10^6$ pfu/ml of the HSV with GALV/R-, mouse GM-CSF and the anti-mouse CTLA-4 antibody inserted (Virus 27);

Effects on tumor growth arc then observed for up to one month. The dose of virus used was $5\times10^4$pfu (50 ul of $1\times10^6$ pfu/ml in each case), given three times over one week. This dose level of virus is subtherapeutic for uninjected tumors for virus 16, which allows the benefits of the delivery of the additional molecules encoded by virus 27 to dearly be seen. FIGS. 5 and 6 show the superior tumor control and shrinkage in uninjected tumors with the virus expressing anti-CTLA-4 compared to with virus 16, which does not express CTLA-4.

Example 3. The Effect of Combined Expression of GALV, GM-CSF and Anti-CTLA4 from an Oncolytic Virus with Anti-PD-1

A20 cells are administered into both flanks of Balb/c mice and the A20 tumors are allowed to grow to approximately 0.5 cm in diameter.

Figure 7:
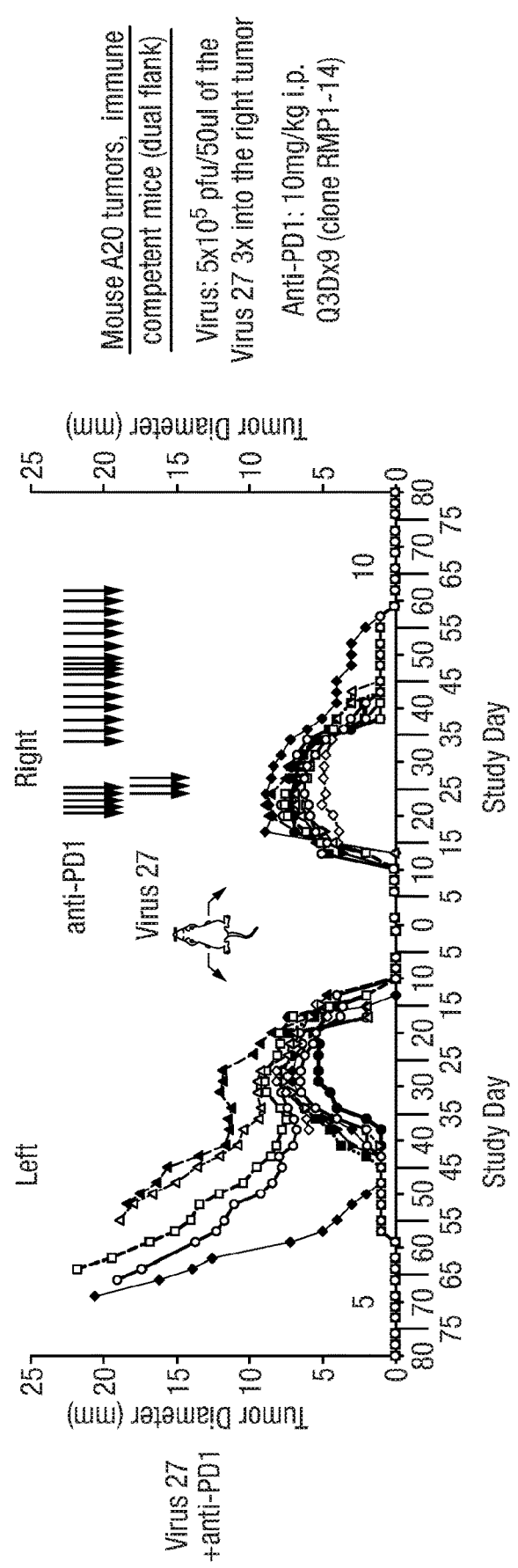
FIG. 7 shows the effect of combined treatment of bilateral mouse A20 tumors using anti-PD1 and virus 27 expressing mGM-CSF, GALVR and anti-mCTLA-4. The top panel shows the effect of anti-PD1 alone on both injected (right) and uninjected (left) tumors. The middle panel shows the effect of virus 27 alone on both injected (right) and uninjected (left) tumors. The bottom panel shows the superior tumor control and shrinkage achieved when anti-PD1 and virus 27 are both injected into the right tumor. The improved anti-tumor effect of the combined treatment is observed in both injected (right) and uninjected (left) tumors. Each line represents a different mouse.

The following treatments are then administered to groups of mice (10 per group), into one flank of each mouse only 3 times per week for one week:
  50 µl of vehicle;
  Intraperitoneal anti-mouse PD1 (Bioxcell RMP-1-14 10 mg/kg every three days);
  50 µl of $10^7$ pfu/ml of the HSV with GALVR-, mouse GM-CSF and the anti-mouse CTLA-4 antibody inserted (Virus 27)
  50 µof $10^7$ pfu/ml, of the HSV with GALVR-, mouse GM-CSF and the anti-mouse CTLA-4 antibody inserted (Virus 27) together with intraperitoneal anti-mouse PD1 (10 mg/kg every three days) (3 groups), Effects on tumor growth are then observed for up to 80 days. Superior tumor control and shrinkage in both injected and un-injected tumors when treatment with the virus is combined treatment with anti-PD1. This data is shown in FIG. 7.

Example 4. The Effect of Combined Expression of GALV, GM-CSF and Anti-HumanCTLA4 from an Oncolytic Virus Alone and in Combination with Anti-PD-1

MC38 cells are administered into both flanks of C57BL/6 mice engineered by gene editing to express human rather than mouse CTLA-4. This renders the mice susceptible to anti-human CTLA-4 antibodies such as ipilimumab. The MC38 tumors are allowed to grow to approximately 0.5 cm in diameter.

The following treatments are then administered to groups of mice (10 per group), into one flank of each mouse only 3 times per week for two weeks:
  50 µl of vehicle;
  50 µl of $10^8$ pfu/ml of Virus 17 (i.e. expressing hGM-CSF and GALV);
  50 µl of $10^8$ pfu/ml of Virus 31 (i.e. expressing hGM-CSF, GALV and anti-human CTLA-4);
  50 µl of $10^8$ pfu/ml of Virus 17 together with intraperitoneal anti-mouse PD1 (10 mg/kg every three days);
  50 µl of $10^8$ pfu/ml of Virus 31 together with intraperitoneal anti-mouse PD1 (10 mg/kg every three days).

Effects on tumor growth are then observed for up to 35 days. Superior tumor control and shrinkage in injected tumors with the virus expressing anti-human CTLA-4 is seen, which is further enhanced with combined treatment with anti-PD1. Superior tumor control and shrinkage is observed in un-injected tumors when treatment with either virus is combined with anti PD1 treatment. The improvement is more marked for the virus that expresses anti CTLA4. This data is shown in FIG. 8.

Example 5. The Effect of Combined Expression of GALV, GM-CSF and Anti-CTLA4 from an Oncolytic Virus with Anti-PD-1

A20 cells are administered into both flanks of Balb/c mice and the A20 tumors are allowed to grow to approximately 0.5 cm in diameter.

The following treatments are then administered to groups of mice (10 per group), into one flank of each mouse only 3 times per week for two weeks:
  50 µl of vehicle (1 group);
  Intraperitoneal anti-mouse PD1 (Bioxcell RMP-1-14 10 mg/kg every three days);
  50 µl of $10^5$ pfu/ml, $10^6$ pfu/ml, or $10^7$ pfu/ml of the HSV with only mouse GM-CSF and GALVR- inserted (3 groups);
  50 µl of $10^5$ pfu/ml, $10^6$ pfu/ml, or $10^7$ pfu/ml of the HSV with GALVR-, mouse GM-CSF and the anti-mouse CTLA-4 antibody inserted together with intraperitoneal anti-mouse PD1 (10 mg/kg every three days) (3 groups
  50 µl of $10^5$ pfu/ml, $10^6$ pfu/ml, or $10^7$ pfu/ml of the HSV with only mouse GM-CSF and GALVR- inserted together with intraperitoneal anti-mouse PD1 (10 mg/kg every three days) (3 groups);

50 µl of $10^5$ pfu/ml, $10^6$ pfu/ml, or $10^7$ pfu/ml of the HSV with GALVR-, mouse GM-CSF and the anti-mouse CTLA-4 antibody inserted together with intraperitoneal anti-mouse PD1 (1.0 mg/kg every three days) (3 groups).

Effects on tumor growth are then observed for up to one month. Superior tumor control and shrinkage in both injected and uninfected tumors with the virus expressing anti-CTLA-4 is seen, which is further enhanced with combined treatment with anti-PD1, as compared to the other groups is observed, including through an improved dose response curve.

Example 6. The Effect of Combined Expression of GALV, GM-CSF and Anti-Human CTLA4 from an Oncolytic Virus Alone and in Combination with Anti-PD-1

MC38 cells are administered into both flanks of C57BL/6 mice engineered by gene editing to express human rather than mouse CTLA-4. This renders the mice susceptible to anti-human CTLA-4 antibodies such as ipilimumab. The MC38 tumors are allowed to grow to approximately 0.5 cm in diameter.

The following treatments are then administered to groups of mice (10 per group), into one flank of each mouse only 3 times per week for two weeks:

50 µl of vehicle (1 group);

Intraperitoneal anti-mouse PD1 (Bioxcell RMP-1-14 10 mg/kg every three days);

50 µl of $10^5$ pfu/ml, $10^6$ pfu/ml, or $10^7$ pfu/ml of the HSV with only mouse GM-CSF and GALVR- inserted (3 groups);

50 µl of $10^5$ pfu/ml, $10^6$ pfu/ml, or $10^7$ pfu/ml of the HSV with GALVR-, mouse GM-CSF and the anti-mouse CTLA-4 antibody inserted together with intraperitoneal anti-mouse PD1 (10 mg/kg every three days) (3 groups);

50 µl of $10^5$ pfu/ml, $10^6$ pfu/ml, or $10^7$ pfu/ml of the HSV with only mouse GM-CSF and GALVR- inserted together with intraperitoneal anti-mouse PD1 (10 mg/kg every three days) (3 groups);

50 µl of $10^5$ pfu/ml, $10^6$ pfu/ml, or $10^7$ pfu/ml of the HSV with GALVR-, mouse GM-CSF and the anti-mouse CTLA-4 antibody inserted together with intraperitoneal anti-mouse PD1 (10 mg/kg every three days) (3 groups).

Effects on tumor growth are then observed for up to one month. Superior tumor control and shrinkage in both injected and uninjected tumors with the virus expressing anti-CTLA-4 is seen, which is further enhanced with combined treatment with anti-PD1, as compared to the other groups is observed, including through an improved dose response curve.

Example 7. The Effect of Combined Expression of GALV, GM-CSF, Anti-CTLA4 and an Immune Co-Stimulatory Pathway Activating Molecule from an Oncolytic Virus The experiment in Example 3 above is repeated but mice are dosed with the viruses additionally expressing the immune co-stimulatory pathway ligands as well as expressing GALV, mGM-CSF and anti-CTLA4, More specifically, groups of mice receive:
(1) Vehicle;
(2) Intraperitoneal anti mouse PD1;
(3) HSV with mGM-CSF, GALVR- and anti-CTLA4 inserted as in Example 2;
(4) HSV with mGM-CSF, GALVR-, anti-CTLA4 and mouse CD40L inserted;
(5) HSV with mGM-CSF, GALVR-, anti-CTLA4 and mouse 4-1BBL inserted;
(6) HSV with mGM-CSF, GALVR-, anti-CTLA4 and mouse GITRL inserted;
(7) HSV with mGM-CSF, GALVR-, anti-CTLA4 and mouse OX40L inserted;
(8) HSV with mGM-CSF GALVR-, anti-CTLA4 and mouse ICOSL inserted;
(9) HSV with mGM-CSF, GALVR- and anti-CTLA4 inserted as in Example 2, together with intraperitoneal anti-PD1;
(10) HSV with mGM-CSF, GALVR-, anti-CTLA4 and mouse CD40L inserted together with intraperitoneal anti-PD1;
(11) HSV with mGM-CSF, anti-CTLA4 and mouse 4-1BBL inserted together with intraperitoneal anti-PD1;
(12) HSV with mGM-CSF, GALVR-, anti-CTLA4 and mouse GITRL inserted together with intraperitoneal anti-PD1;
(13) HSV with mGM-CSF, GALVR-, anti-CTL A4 and mouse OX40L inserted together with intraperitoneal anti-PD1; or
(14) HSV with mGM-CSF, GALVR-, anti-CTLA4 and mouse ICOSL inserted together with intraperitoneal anti-PD1.

Superior tumor control is seen with the viruses expressing the immune co-stimulatory ligands.

Deposit Information

The following HSV1 strains were deposited at the ECACC, Culture Collections, Public Health England, Porton Down, Salisbury, SP4 0JG, United Kingdom on 19 Dec. 2016 by Rep Limited and were allocated the indicated accession numbers:

RH004A—Accession Number 16121902
RH015A—Accession Number 16121903
RH018A—Accession Number 16121904
RH021A—Accession Number 16121905
RH023A—Accession Number 16121906
RH031A—Accession Number 16121907
RH040B—Accession Number 16121908
RH047A—Accession Number 16121909.

The invention claimed is:

1. An oncolytic herpes simplex virus 1 (HSV1) which is strain RH018A having the accession number ECACC 16121904 modified to encode a CTLA-4 inhibitor.

2. The virus of claim 1, wherein the CTLA-4 inhibitor is an anti-CTLA-4 antibody, or an antigen binding fragment thereof.

3. The virus of claim 2, wherein the fragment comprises a scFv molecule.

4. The virus of claim 2, wherein the fragment is a scFv molecule linked to one or more IgG1 constant regions.

5. The virus of claim 2, wherein the antibody or fragment comprises a light chain variable region sequence linked to an IgG heavy chain.

6. The virus of claim 2, wherein the antibody or fragment comprises (a) the light chain variable region sequence shown in SEQ ID NO: 1 and the heavy chain variable region sequence shown in SEQ ID NOs: 3; or (b) the light chain variable region sequence shown in SEQ ID NO: 11 and the heavy chain variable region sequence shown in SEQ ID NO: 12.

7. The virus of claim 6, wherein the antibody or fragment comprises (a) the amino acid sequence of SEQ ID NO: 9; or (b) the amino acid sequence of SEQ ID NO: 14.

8. The virus of claim 7, wherein the antibody or fragment is encoded by (a) the nucleotide sequence of SEQ ID NO: 10; or (b) the nucleotide sequence of SEQ ID NO: 15.

9. The virus of claim 1, wherein the virus further comprises a GM-CSF-encoding gene.

10. The virus of claim 1, wherein the virus further comprises an immune co-stimulatory pathway activating molecule or an immune co-stimulatory pathway activating molecule-encoding gene.

11. The virus of claim 10, wherein the immune co-stimulatory pathway activating molecule-encoding gene encodes CD40 ligand (CD40L), ICOS ligand, GITR ligand, 4-1-BB ligand, OX40 ligand, TLIA, CD30 ligand, CD27 or flt3 ligand or a modified version of any of these.

12. The virus of claim 10, wherein the immune co-stimulatory pathway activating molecule-encoding gene encodes CD40 ligand, GITR ligand, 4-1-BB ligand, OX40 ligand, ICOS ligand or a modified version of any of these.

13. The virus of claim 1, further comprising a fusogenic protein-encoding gene.

14. The virus of claim 13 where the fusogenic protein is selected from the group consisting of vesicular stomatitis virus (VSV) G-protein, syncitin-1, syncitin-2, simian virus 5 (SV5) F-protein, measles virus (MV) H-protein, MV F-protein, respiratory syncytial virus (RSV) F-protein and a glycoprotein from gibbon ape leukemia virus (GALV), murine leukemia virus (MLV), Mason-Pfizer monkey virus (MPMV) or equine infectious anaemia virus (EIAV) from which the R peptide has been deleted.

15. The virus of claim 13, wherein the fusogenic protein is the glycoprotein from gibbon ape leukemia virus (GALV) and has the R transmembrane peptide mutated or removed (GALV-R-).

16. The virus of claim 1, which encodes more than one immune co-stimulatory pathway activating molecule.

17. The virus of claim 1, wherein the HSV:
(a) does not express functional ICP34.5;
(b) does not express functional ICP47; and/or
(c) expresses the US11 gene as an immediate early gene.

18. The virus of claim 1, wherein an anti-CTLA-4 inhibiting protein encoding gene has been inserted into the ICP34.5 encoding locus by insertion, partial deletion or complete deletion.

19. The virus of claim 18, wherein the anti-CTLA-4 inhibiting protein encoding gene is included in a cassette also including one or more immune stimulating gene(s) and/or an immune co-stimulatory pathway activating molecule encoding gene and/or a fusogenic protein encoding gene.

20. The virus of claim 1, wherein the sequence encoding the CTLA-4 inhibitor is codon optimized so as to increase expression levels in target cells.

21. A virus according to claim 1, which expresses three heterologous genes, wherein each of the three heterologous genes is driven by a different promoter selected from the CMV promoter, the RSV promoter, the SV40 promoter and a retroviral LTR promoter.

22. The virus of claim 21, which expresses four heterologous genes driven by each of the CMV promoter, the RSV promoter, the SV40 promoter and a retroviral LTR promoter, respectively.

23. The virus of claim 21, where the retroviral LTR is from MMLV.

24. A virus according to claim 1, which expresses three heterologous genes, wherein each of the three heterologous genes is terminated by a different poly adenylation sequence selected from the BGH, SV40, HGH and RBG poly adenylation sequences.

25. The virus of claim 24, which expresses four heterologous genes terminated by each of the BGH, SV40, HGH and RBG poly adenylation sequences, respectively.

26. A pharmaceutical composition comprising a virus according to claim 1 and a pharmaceutically acceptable carrier or diluent.

27. A product of manufacture comprising a virus according to claim 1 in a sterile vial, ampoule or syringe.

28. A method of treating cancer, which comprises administering a therapeutically effective amount of the virus of claim 1 to a patient in need thereof.

29. The method according to of claim 28, which further comprises administering a therapeutically effective amount of a further anti-cancer agent to a patient in need thereof.

30. The method of claim 29, wherein the further anti-cancer agent is selected from the group consisting of an agent targeting an immune co-inhibitory or immune co-stimulatory pathway, radiation and/or chemotherapy, an agent that targets a specific genetic mutation which occurs in tumors, an agent intended to induce an immune response to one or more tumor antigen(s) or neoantigen(s), a cellular product derived from T cells or NK cells, an agent intended to stimulate the STING, cGAS, TLR or other innate immune response and/or inflammatory pathway, a second virus optionally an oncolytic virus, and combinations thereof.

31. The method of claim 30, wherein the agent targeting an immune co-inhibitory pathway is a PD-1 inhibitor, a PD-L1 inhibitor, a LAG-3 inhibitor, a TIM-3 inhibitor, a VISTA inhibitor, aCSFIR inhibitor, an IDO inhibitor, a KIR inhibitor, a SLAMF7 inhibitor, a CEACAM1 inhibitor or a CD47 inhibitor, and/or the agent targeting an immune co-stimulatory pathway is a GITR agonist, a 4-1-BB agonist, an OX40 agonist, a CD40 agonist or an ICOS agonist.

32. The method of claim 29, wherein the further anti-cancer agent comprises an antibody.

33. The method of claim 29, wherein the virus and the further anti-cancer agent(s) are administered separately.

34. The method of claim 29, wherein the virus and the further anti-cancer agent(s) are administered concurrently.

35. The method of claim 28, wherein the cancer is a solid tumor.

36. The virus of claim 18, wherein the anti-CTLA-4 inhibiting protein encoding gene is included in a cassette also including GM-CSF and/or an immune co-stimulatory pathway activating molecule encoding gene and/or a fusogenic protein encoding gene.

37. The virus of claim 21, where the retroviral LTR is SEQ ID NO: 43.

* * * * *

SEQUENCE LISTING

<160> NUMBER OF SEQ ID NOS: 46

<210> SEQ ID NO 1
<211> LENGTH: 108
<212> TYPE: PRT
<213> ORGANISM: Homo sapiens -continued

<400> SEQUENCE: 1

Ile Val Leu Thr Gln Ser Pro Gly Thr Leu Ser Leu Ser Pro Gly Glu
1               5                   10                  15

Arg Ala Thr Leu Ser Cys Arg Ala Ser Gln Ser Val Gly Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Phe Ser Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg
            100                 105

<210> SEQ ID NO 2
<211> LENGTH: 215
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 3
<211> LENGTH: 118
<212> TYPE: PRT
<213> ORGANISM: Homo sapiens

```
<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 4
<211> LENGTH: 103
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 5
<211> LENGTH: 227
<212> TYPE: PRT
<213> ORGANISM: Homo sapiens

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

```
                85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
210                 215                 220

Pro Gly Lys
225

<210> SEQ ID NO 6
<211> LENGTH: 448
<212> TYPE: PRT
<213> ORGANISM: Homo sapiens

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220
```

His Thr Cys Pro Pro Cys Pro Ala Pro Glu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 7
<211> LENGTH: 21
<212> TYPE: PRT
<213> ORGANISM: Mus musculus

<400> SEQUENCE: 7

Met Glu Thr Asp Thr Leu Leu Leu Trp Val Leu Leu Trp Val Pro
1               5                   10                  15

Gly Ser Thr Gly Asp
            20

<210> SEQ ID NO 8
<211> LENGTH: 15
<212> TYPE: PRT
<213> ORGANISM: Artificial Sequence
<220> FEATURE:
<223> OTHER INFORMATION: (Gly4Ser)3 linker

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 489
<212> TYPE: PRT
<213> ORGANISM: Homo sapiens

<400> SEQUENCE: 9

Met Glu Thr Asp Thr Leu Leu Leu Trp Val Leu Leu Trp Val Pro
1               5                   10                  15

-continued

```
Gly Ser Thr Gly Asp Ile Val Leu Thr Gln Ser Pro Gly Thr Leu Ser
         20                  25                  30

Leu Ser Pro Gly Glu Arg Ala Thr Leu Ser Cys Arg Ala Ser Gln Ser
         35                  40                  45

Val Gly Ser Ser Tyr Leu Ala Trp Tyr Gln Gln Lys Pro Gly Gln Ala
 50                  55                  60

Pro Arg Leu Leu Ile Tyr Gly Ala Phe Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Lys Val Glu Ile Lys
            115                 120                 125

Arg Gly Gly Gly Ser Gly Gly Gly Ser Gly Gly Gly Ser
130                 135                 140

Gln Val Gln Leu Val Glu Ser Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Thr Met His Trp Val Arg Gln Ala Pro Gly Lys Gly Leu Glu Trp Val
            180                 185                 190

Thr Phe Ile Ser Tyr Asp Gly Asn Asn Lys Tyr Tyr Ala Asp Ser Val
            195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Ile Tyr Tyr Cys
225                 230                 235                 240

Ala Arg Thr Gly Trp Leu Gly Pro Phe Asp Tyr Trp Gly Gln Gly Thr
                245                 250                 255

Leu Val Thr Val Ser Ser Asp Lys Thr His Thr Cys Pro Pro Cys Pro
            260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
            370                 375                 380

Pro Arg Glu Pro Gln Val Tyr Thr Leu Pro Pro Ser Arg Glu Glu Met
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430
```

Tyr Lys Thr Thr Pro Pro Val Leu Asp Ser Asp Gly Ser Phe Phe Leu
            435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 10
<211> LENGTH: 1470
<212> TYPE: DNA
<213> ORGANISM: Homo sapiens

<400> SEQUENCE: 10

```
atggaaactg acaccctgct gctgtgggtc ctgctgctgt gggtgcctgg atccaccggc        60
gatatcgtgc tgacccagtc tcctggcaca ctgagtctgt caccagggga gcgagcaaca       120
ctgtcttgta gagccagcca gtctgtggga agctcctacc tggcttggta tcagcagaag       180
ccaggccagg cacccaggct gctgatctac ggagccttca gccgggccac tggcattcca       240
gacaggttct ctggaagtgg ctcagggacc gacttcaccc tgaccatcag ccgactggag       300
cccgaagact cgccgtgta ctattgccag cagtacggct ctagtccttg acttttgga         360
cagggcacca aagtggagat caagcgcggc ggggaggc ctgggggagg cgggagtgga         420
ggcgggggat cacaggtcca gctggtggaa agcggcgggg agtggtcca gccaggccgg        480
agcctgcggc tgagctgcgc cgcttcagga ttcacatttt caagctatac catgcactgg       540
gtccggcagg caccagggaa gggactggag tgggtgacct catcagcta tgacggcaac        600
aacaagtatt acgctgattc cgtgaaaggg aggtttacca ttagccgcga caactccaaa       660
aatacactgt acctgcagat gaacagcctg cgggccgagg atactgctat ctactattgc       720
gcaagaaccg gtggctggg acccttcgac tattggggcc aggggactct ggtcaccgtg        780
tcctctgata agacacacac atgccctccc tgtcctgcac cagagctgct gggcgggcca       840
tccgtgttcc tgtttccacc caagcctaaa gacaccctga tgatcagccg gacacctgaa       900
gtcacttgcg tggtcgtgga cgtgagtcac gaggatccag aagtcaagtt taactggtac       960
gtggatggcg tcgaggtgca taatgccaag accaaacctc gcgaggaaca gtacaatagc      1020
acatatcgag tcgtgtccgt cctgactgtg ctgcatcagg attggctgaa cggcaaagag      1080
tataagtgca agtgagcaa taaggcactg cctgccccaa tcgagaaaac aatttccaag      1140
gctaaaggcc agcccaggga acctcaggtg tacactctgc ctccaagtcg cgaggaaatg      1200
accaagaacc aggtgagcct gacctgtctg gtgaaagggt tctatccatc agacattgca      1260
gtggagtggg aaagcaatgg acagcccgaa aacaattaca gaccacacc ccctgtgctg       1320
gacagcgatg gctccttctt tctgtattct aagctgactg tggataaaag tcgctggcag      1380
caggggaacg tctttagctg ttccgtgatg catgaggctc tgcacaatca ttacacacag      1440
aagtctctga gtctgtcacc cggcaaatga                                       1470
```

<210> SEQ ID NO 11
<211> LENGTH: 127
<212> TYPE: PRT
<213> ORGANISM: Mus musculus

<400> SEQUENCE: 11

Ile Arg Arg Ala Asp Ile Val Met Thr Gln Thr Thr Leu Ser Leu Pro

```
                1               5                  10                  15
            Val Ser Leu Gly Asp Gln Ala Ser Ile Ser Cys Arg Ser Ser Gln Ser
                            20                  25                  30

Ile Val His Ser Asn Gly Asn Thr Tyr Leu Glu Trp Tyr Leu Gln Lys
                            35                  40                  45

Pro Gly Gln Ser Pro Lys Leu Leu Ile Tyr Lys Val Ser Asn Arg Phe
                            50                  55                  60

Ser Gly Val Pro Asp Arg Phe Ser Gly Ser Gly Ser Gly Thr Asp Phe
             65                 70                  75                  80

Thr Leu Lys Ile Ser Arg Val Glu Ala Glu Asp Leu Gly Val Tyr Tyr
                            85                  90                  95

Cys Phe Gln Gly Ser His Val Pro Tyr Thr Phe Gly Gly Gly Thr Lys
                            100                 105                 110

Leu Glu Ile Lys Arg Ala Asp Ala Ala Pro Thr Val Ser Gly Ser
                            115                 120                 125

<210> SEQ ID NO 12
<211> LENGTH: 134
<212> TYPE: PRT
<213> ORGANISM: Mus musculus

<400> SEQUENCE: 12

Glu Ala Lys Leu Gln Glu Ser Gly Pro Val Leu Val Lys Pro Gly Ala
            1               5                   10                  15

Ser Val Lys Met Ser Cys Lys Ala Ser Gly Tyr Thr Phe Thr Asp Tyr
                            20                  25                  30

Tyr Met Asn Trp Val Lys Gln Ser His Gly Lys Ser Leu Glu Trp Ile
                            35                  40                  45

Gly Val Ile Asn Pro Tyr Asn Gly Asp Thr Ser Tyr Asn Gln Lys Phe
                            50                  55                  60

Lys Gly Lys Ala Thr Leu Thr Val Asp Lys Ser Ser Ser Thr Ala Tyr
             65                 70                  75                  80

Met Glu Leu Asn Ser Leu Thr Ser Glu Asp Ser Ala Val Tyr Tyr Cys
                            85                  90                  95

Ala Arg Tyr Tyr Gly Ser Trp Phe Ala Tyr Trp Gly Gln Gly Thr Leu
                            100                 105                 110

Ile Thr Val Ser Thr Ala Lys Thr Thr Pro Pro Ser Val Tyr Pro Leu
                            115                 120                 125

Ala Pro Arg Ser Ser Arg
                            130

<210> SEQ ID NO 13
<211> LENGTH: 356
<212> TYPE: PRT
<213> ORGANISM: Mus musculus

<400> SEQUENCE: 13

Glu Ala Lys Leu Gln Glu Ser Gly Pro Val Leu Val Lys Pro Gly Ala
            1               5                   10                  15

Ser Val Lys Met Ser Cys Lys Ala Ser Gly Tyr Thr Phe Thr Asp Tyr
                            20                  25                  30

Tyr Met Asn Trp Val Lys Gln Ser His Gly Lys Ser Leu Glu Trp Ile
                            35                  40                  45

Gly Val Ile Asn Pro Tyr Asn Gly Asp Thr Ser Tyr Asn Gln Lys Phe
                            50                  55                  60

Lys Gly Lys Ala Thr Leu Thr Val Asp Lys Ser Ser Ser Thr Ala Tyr
```

65                  70                  75                  80
Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Pro Pro Ser Val Tyr Pro Leu
            115                 120                 125

Ala Pro Arg Ser Arg Gly Cys Lys Pro Cys Ile Cys Thr Val Pro
130             135                 140

Glu Val Ser Ser Val Phe Ile Phe Pro Pro Lys Pro Lys Asp Val Leu
145             150                 155                 160

Thr Ile Thr Leu Thr Pro Lys Val Thr Cys Val Val Asp Ile Ser
                165                 170                 175

Lys Asp Asp Pro Glu Val Gln Phe Ser Trp Phe Val Asp Val Glu
                180                 185                 190

Val His Thr Ala Gln Thr Gln Pro Arg Glu Glu Gln Phe Asn Ser Thr
            195                 200                 205

Phe Arg Ser Val Ser Glu Leu Pro Ile Met His Gln Asp Trp Leu Asn
210             215                 220

Gly Lys Glu Phe Lys Cys Arg Val Asn Ser Ala Ala Phe Pro Ala Pro
225             230                 235                 240

Ile Glu Lys Thr Ile Ser Lys Thr Lys Gly Arg Pro Lys Ala Pro Gln
                245                 250                 255

Val Tyr Thr Ile Pro Pro Lys Glu Gln Met Ala Lys Asp Lys Val
                260                 265                 270

Ser Leu Thr Cys Met Ile Thr Asp Phe Phe Pro Glu Asp Ile Thr Val
            275                 280                 285

Glu Trp Gln Trp Asn Gly Gln Pro Ala Glu Asn Tyr Lys Asn Thr Gln
290             295                 300

Pro Ile Met Asp Thr Asp Gly Ser Tyr Phe Val Tyr Ser Lys Leu Asn
305             310                 315                 320

Val Gln Lys Ser Asn Trp Glu Ala Gly Asn Thr Phe Thr Cys Ser Val
                325                 330                 335

Leu His Glu Gly Leu His Asn His Thr Glu Lys Ser Leu Ser His
            340                 345                 350

Ser Pro Gly Lys
            355

<210> SEQ ID NO 14
<211> LENGTH: 519
<212> TYPE: PRT
<213> ORGANISM: Mus musculus

<400> SEQUENCE: 14

Met Glu Thr Asp Thr Leu Leu Leu Trp Val Leu Leu Leu Trp Val Pro
1               5                   10                  15

Gly Ser Thr Gly Asp Ile Arg Arg Ala Asp Ile Val Met Thr Gln Thr
            20                  25                  30

Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
    50                  55                  60

Trp Tyr Leu Gln Lys Pro Gly Gln Ser Pro Lys Leu Leu Ile Tyr Lys
65                  70                  75                  80

-continued

Val Ser Asn Arg Phe Ser Gly Val Pro Asp Arg Phe Ser Gly Ser Gly
              85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
            115                 120                 125

Gly Gly Gly Thr Lys Leu Glu Ile Lys Arg Ala Asp Ala Ala Pro Thr
        130                 135                 140

Val Ser Gly Ser Gly Gly Gly Ser Gly Gly Gly Ser Gly
145                 150                 155                 160

Gly Gly Ser Glu Ala Lys Leu Gln Glu Ser Gly Pro Val Leu Val Lys
            165                 170                 175

Pro Gly Ala Ser Val Lys Met Ser Cys Lys Ala Ser Gly Tyr Thr Phe
            180                 185                 190

Thr Asp Tyr Tyr Met Asn Trp Val Lys Gln Ser His Gly Lys Ser Leu
            195                 200                 205

Glu Trp Ile Gly Val Ile Asn Pro Tyr Asn Gly Asp Thr Ser Tyr Asn
    210                 215                 220

Gln Lys Phe Lys Gly Lys Ala Thr Leu Thr Val Asp Lys Ser Ser Ser
225                 230                 235                 240

Thr Ala Tyr Met Glu Leu Asn Ser Leu Thr Ser Glu Asp Ser Ala Val
            245                 250                 255

Tyr Tyr Cys Ala Arg Tyr Tyr Gly Ser Trp Phe Ala Tyr Trp Gly Gln
            260                 265                 270

Gly Thr Leu Ile Thr Val Ser Thr Ala Lys Thr Thr Pro Pro Ser Val
        275                 280                 285

Tyr Pro Leu Ala Pro Arg Ser Ser Arg Gly Cys Lys Pro Cys Ile Cys
    290                 295                 300

Thr Val Pro Glu Val Ser Ser Val Phe Ile Phe Pro Pro Lys Pro Lys
305                 310                 315                 320

Asp Val Leu Thr Ile Thr Leu Thr Pro Lys Val Thr Cys Val Val Val
            325                 330                 335

Asp Ile Ser Lys Asp Asp Pro Glu Val Gln Phe Ser Trp Phe Val Asp
            340                 345                 350

Asp Val Glu Val His Thr Ala Gln Thr Gln Pro Arg Glu Glu Gln Phe
        355                 360                 365

Asn Ser Thr Phe Arg Ser Val Ser Glu Leu Pro Ile Met His Gln Asp
    370                 375                 380

Trp Leu Asn Gly Lys Glu Phe Lys Cys Arg Val Asn Ser Ala Ala Phe
385                 390                 395                 400

Pro Ala Pro Ile Glu Lys Thr Ile Ser Lys Thr Lys Gly Arg Pro Lys
            405                 410                 415

Ala Pro Gln Val Tyr Thr Ile Pro Pro Pro Lys Glu Gln Met Ala Lys
            420                 425                 430

Asp Lys Val Ser Leu Thr Cys Met Ile Thr Asp Phe Phe Pro Glu Asp
        435                 440                 445

Ile Thr Val Glu Trp Gln Trp Asn Gly Gln Pro Ala Glu Asn Tyr Lys
    450                 455                 460

Asn Thr Gln Pro Ile Met Asp Thr Asp Gly Ser Tyr Phe Val Tyr Ser
465                 470                 475                 480

Lys Leu Asn Val Gln Lys Ser Asn Trp Glu Ala Gly Asn Thr Phe Thr
            485                 490                 495

Cys Ser Val Leu His Glu Gly Leu His Asn His His Thr Glu Lys Ser

```
                500             505             510
Leu Ser His Ser Pro Gly Lys
        515

<210> SEQ ID NO 15
<211> LENGTH: 1560
<212> TYPE: DNA
<213> ORGANISM: Mus musculus

<400> SEQUENCE: 15
atggaaactg atactctgct gctctgggtg ctgctcctct gggtgcctgg ttcaactggg     60
gacattcgac gggctgacat tgtgatgacc cagaccacac tgagcctgcc cgtgtccctg    120
ggcgaccagg ccagcatctc ctgccggagc tcccagtcta tcgtgcacag caacggaaac    180
acatacctgg agtggtatct gcagaagcct ggccagtccc caaagctgct gatctacaag    240
gtgtccaaca ggttcagcgg cgtgcctgac cgcttttctg aagcggctc cggaacagat     300 ttcaccctga gatcagcag gtggaggct gaggacctgg cgtgtacta ctgcttccag        360 ggatcccacg tgccttacac ctttggcgga ggcacaaagc tggagatcaa gagagccgat    420
gctgctccaa ccgtgtctgg aagcggaggc ggggttctg aggcggtgg agcggtggc       480 ggagggtctg aggctaagct gcaggagagc ggccccgtgc tggtgaagcc tggagccagc    540
gtgaagatgt cctgtaaggc ttctggatac accttcacag actactacat gaactgggtg    600
aagcagagcc acggcaagtc cctggagtgg atcggagtga tcaacccctta caacggcgac    660 acctcttaca accagaagtt taagggcaag gccaccctga cagtggataa gtctagctcc    720
accgcttaca tggagctgaa cagcctgaca tccgaggatt ctgccgtgta ctactgtgct    780
aggtactacg gaagctggtt cgcctactgg ggccagggaa cactgatcac cgtgtccaca    840
gccaagacca caccccctag cgtgtacccc ctggctccta gtctagcag aggctgcaag    900 ccatgcatct gtaccgtgcc cgaggtgagc agcgtgttca tctttccacc caagcccaag    960
gacgtgctga ccatcacact gacccctaag gtgacatgcg tggtggtgga tatcagcaag   1020
gacgatccag aggtgcagtt ctcctggttt gtggacgatg tggaggtgca caccgcccag   1080
acacagccaa gggaggagca gttcaactcc acctttagat ccgtgtctga gctgcccatc   1140
atgcaccagg actggctgaa cggaaaggag ttcaagtgcc gggtgaactc cgccgctttt   1200
cctgctccaa tcgagaagac catctctaag acaaagggcc gcccaaaggc tccacaggtg   1260
tacaccatcc ctccacccaa ggagcagatg gctaaggata aggtgagcct gacctgtatg   1320
atcacagact ctttcccga ggatatcaca gtggagtgg agtggaacgg acagcctgcc    1380
gagaactaca agaacacccca gccaatcatg gacacagatg gctcttactt cgtgtacagc   1440
aagctgaacg tgcagaagtc taactgggag gctggcaaca ccttcacctg cagcgtgctg   1500
cacgaaggtc tccataatca ccacaccgaa aagagcctca gtcacagccc tgggaaatga   1560

<210> SEQ ID NO 16
<211> LENGTH: 1574
<212> TYPE: DNA
<213> ORGANISM: Mus musculus

<400> SEQUENCE: 16
cttaagatgg aaactgatac tctgctgctc tgggtgctgc tcctctgggt gcctggttca     60
actggggaca ttcgacgggc tgacattgtg atgacccaga ccacactgag cctgcccgtg   120
tccctgggcg accaggccag catctcctgc cggagctccc agtctatcgt gcacagcaac   180
```

```
ggaaacacat acctggagtg gtatctgcag aagcctggcc agtccccaaa gctgctgatc      240
tacaaggtgt ccaacaggtt cagcggcgtg cctgaccgct tttctggaag cggctccgga      300
acagatttca ccctgaagat cagcagggtg gaggctgagg acctgggcgt gtactactgc      360
ttccagggat cccacgtgcc ttacaccttt ggcggaggca caaagctgga gatcaagaga      420
gccgatgctg ctccaaccgt gtctggaagc ggaggcgggg gttctggagg cggtgggagc      480
ggtggcggag ggtctgaggc taagctgcag gagagcggcc ccgtgctggt gaagcctgga      540
gccagcgtga agatgtcctg taaggcttct ggatacacct tcacagacta ctacatgaac      600
tgggtgaagc agagccacgg caagtccctg gagtggatcg gagtgatcaa cccttacaac      660
ggcgacacct cttacaacca gaagtttaag ggcaaggcca ccctgacagt ggataagtct      720
agctccaccg cttacatgga gctgaacagc ctgacatccg aggattctgc cgtgtactac      780
tgtgctaggt actacggaag ctggttcgcc tactggggcc agggaacact gatcaccgtg      840
tccacagcca agaccacacc ccctagcgtg taccccctgg ctcctaggtc tagcagaggc      900
tgcaagccat gcatctgtac cgtgcccgag gtgagcagcg tgttcatctt ccacccaag       960 cccaaggacg tgctgaccat cacactgacc cctaaggtga catgcgtggt ggtggatatc     1020
agcaaggacg atccagaggt gcagttctcc tggtttgtgg acgatgtgga ggtgcacacc     1080
gcccagacac agccaaggga ggagcagttc aactccacct ttagatccgt gtctgagctg     1140
cccatcatgc accaggactg gctgaacgga aggagttca gtgccgggt gaactccgcc       1200 gcttttcctg ctccaatcga gaagaccatc tctaagacaa agggccgccc aaaggctcca     1260
caggtgtaca ccatccctcc acccaaggag cagatggcta aggataaggt gagcctgacc     1320
tgtatgatca cagacttctt tcccgaggat atcacagtgg agtggcagtg aacggacag      1380 cctgccgaga actacaagaa cacccagcca atcatggaca cagatggctc ttacttcgtg     1440
tacagcaagc tgaacgtgca gaagtctaac tgggaggctg caacaccttt cacctgcagc     1500
gtgctgcacg aaggtctcca taatcaccac accgaaaaga gcctcagtca cagccctggg     1560
aaatgaggcg cgcc                                                        1574
```

<210> SEQ ID NO 17
<211> LENGTH: 1484
<212> TYPE: DNA
<213> ORGANISM: Homo sapiens

<400> SEQUENCE: 17

```
cttaagatgg aaactgacac cctgctgctg tgggtcctgc tgctgtgggt gcctggatcc       60
accggcgata tcgtgctgac ccagtctcct ggcacactga gtctgtcacc aggggagcga      120
gcaacactgt cttgtagagc cagccagtct gtgggaagct cctacctggc ttggtatcag      180
cagaagccag gccaggcacc caggctgctg atctacggag ccttcagccg ggccactggc      240
attccagaca ggttctctgg aagtggctca gggaccgact tcaccctgac catcagccga      300
ctggagcccg aagacttcgc cgtgtactat tgccagcagt acggctctag tccttggact      360
tttggacagg gcaccaaagt ggagatcaag cgcggcgggg gaggctctgg gggaggcggg      420
agtggaggcg ggggatcaca ggtccagctg gtggaaagcg gcggggagt ggtccagcca      480 ggccggagcc tgcggctgag ctgcgccgct tcaggattca catttttcaag ctataccatg      540 cactgggtcc ggcaggcacc agggaaggga ctggagtggg tgaccttcat cagctatgac      600
ggcaacaaca gtattacgc tgattccgtg aagggaggt ttaccattag ccgcgacaac       660
tccaaaaata cactgtacct gcagatgaac agcctgcggg ccgaggatac tgctatctac      720
```

```
tattgcgcaa gaaccgggtg gctgggaccc ttcgactatt ggggccaggg gactctggtc    780
accgtgtcct ctgataagac acacacatgc cctccctgtc ctgcaccaga gctgctgggc    840
gggccatccg tgttcctgtt tccacccaag cctaaagaca ccctgatgat cagccggaca    900
cctgaagtca cttgcgtggt cgtggacgtg agtcacgagg atccagaagt caagtttaac    960
tggtacgtgg atggcgtcga ggtgcataat gccaagacca aacctcgcga ggaacagtac   1020
aatagcacat atcgagtcgt gtccgtcctg actgtgctgc atcaggattg gctgaacggc   1080
aaagagtata agtgcaaagt gagcaataag gcactgcctg ccccaatcga gaaacaatt   1140 tccaaggcta aaggccagcc cagggaacct caggtgtaca ctctgcctcc aagtcgcgag   1200
gaaatgacca gaaccaggt gagcctgacc tgtctggtga aagggttcta tccatcagac   1260
attgcagtgg agtgggaaag caatggacag cccgaaaaca attacaagac cacccccct   1320 gtgctggaca gcgatggctc cttctttctg tattctaagc tgactgtgga taaaagtcgc   1380
tggcagcagg ggaacgtctt tagctgttcc gtgatgcatg aggctctgca caatcattac   1440
acacagaagt ctctgagtct gtcacccggc aaatgaggcg cgcc                   1484

<210> SEQ ID NO 18
<211> LENGTH: 426
<212> TYPE: DNA
<213> ORGANISM: Mus musculus

<400> SEQUENCE: 18
atgtggctgc agaatttact tttcctgggc attgtggtct acagcctctc agcacccacc     60
cgctcaccca tcactgtcac ccggccttgg aagcatgtag aggccatcaa agaagccctg    120
aacctcctgg atgacatgcc tgtcacattg aatgaagagg tagaagtcgt ctctaacgag    180
ttctccttca agaagctaac atgtgtgcag acccgcctga gatattcga gcagggtcta    240 cggggcaatt tcaccaaaac tcaagggcgc cttgaacatga cagccagcta ctaccagaca    300
tactgccccc caactccgga aacggactgt gaaacacaag ttaccaccta tgcggatttc    360
atagacagcc ttaaaacctt tctgactgat atcccctttg aatgcaaaaa accagtccaa    420
aaatga                                                              426

<210> SEQ ID NO 19
<211> LENGTH: 426
<212> TYPE: DNA
<213> ORGANISM: Mus musculus

<400> SEQUENCE: 19
atgtggctcc agaacctcct cttcctcggt atcgtcgtgt attcactctc cgcacctact     60
cgctcaccta tcactgtcac cagacccgg aagcacgtgg aggccatcaa ggaggctctg    120
aacctgctgg acgatatgcc agtgaccctg aacgaggagg tggaggtggt gagcaacgag    180 ttctcctttta agaagctgac ctgcgtgcag acaaggctga gatcttcga gcagggcctg    240 agaggaaact ttaccaagct gaagggcgcc ctgaacatga ccgcttctta ctaccagaca    300
tactgccccc ctaccccga cagactgt gagacacagg tgaccacata cgccgacttc    360
attgatagcc tgaaaacatt cctgaccgac attccatttg agtgtaagaa gcccgtccag    420
aagtaa                                                              426

<210> SEQ ID NO 20
<211> LENGTH: 435
<212> TYPE: DNA
```

<213> ORGANISM: Homo sapiens

<400> SEQUENCE: 20

```
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga atgaaacagt agaagtcatc     180
tcagaaatgt ttgacctcca ggagccgacc tgcctacaga cccgcctgga gctgtacaag     240
cagggcctgc ggggcagcct caccaagctc aagggcccct tgaccatgat ggccagccac     300
tacaagcagc actgccctcc aaccccggaa acttcctgtg caacccagat tatcaccttt     360
gaaagtttca agagaaacct gaaggacttt ctgcttgtca tcccctttga ctgctgggag     420
ccagtccagg agtga                                                      435
```

<210> SEQ ID NO 21
<211> LENGTH: 435
<212> TYPE: DNA
<213> ORGANISM: Homo sapiens

<400> SEQUENCE: 21

```
atgtggctgc agtccctgct gctgctgggc accgtcgcct gttctatttc cgcacccgca      60
aggtcaccaa gtccatctac tcagccttgg gagcacgtga acgcaatcca ggaggcacgg     120
cggctgctga acctgagccg ggacaccgcc gccgagatga cgagacagt ggaagtgatc      180
agcgagatgt tcgatctgca ggagcccacc tgcctgcaga caaggctgga gctgtacaag     240
cagggcctgc gcggctctct gaccaagctg aagggcccac tgacaatgat ggccagccac     300
tataagcagc actgccccc taccccgag acaagctgtg ccacccagat catcacattc       360
gagtccttta aggagaacct gaaggatttt ctgctggtca ttccatttga ttgttgggag     420
cccgtccagg agtaa                                                      435
```

<210> SEQ ID NO 22
<211> LENGTH: 141
<212> TYPE: PRT
<213> ORGANISM: Mus musculus

<400> SEQUENCE: 22

```
Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys
    130                 135                 140
```

<210> SEQ ID NO 23
<211> LENGTH: 144
<212> TYPE: PRT
<213> ORGANISM: Homo sapiens

<400> SEQUENCE: 23

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 24
<211> LENGTH: 2010
<212> TYPE: DNA
<213> ORGANISM: Gibbon leukemia virus

<400> SEQUENCE: 24
atggtattgc tgcctgggtc catgcttctc acctcaaacc tgcaccacct tcggcaccag      60
atgagtcctg ggagctggaa aagactgatc atcctcttaa gctgcgtatt cggcggcggc     120
gggacgagtc tgcaaaataa gaaccccac cagcccatga ccctcacttg gcaggtactg     180
tcccaaactg gagacgttgt ctgggataca aaggcagtcc agccccttg gacttggtgg     240 cccacactta acctgatgt atgtgccttg gcggctagtc ttgagtcctg ggatatcccg     300
ggaaccgatg tctcgtcctc taaacgagtc agacctccgg actcagacta tactgccgct     360
tataagcaaa tcacctgggg agccataggg tgcagctacc ctcgggctag gactagaatg     420
gcaagctcta ccttctacgt atgtccccgg gatggccgga ccctttcaga gctagaaggg     480 tgcgggggc tagaatccct atactgtaaa gaatgggatt gtgagaccac ggggaccggt     540
tattggctat ctaatcctc aaaagacctc ataactgtaa atgggaccaa aatagcgaa     600 tggactcaaa aatttcaaca gtgtcaccag accggctggt gtaacccct taaatagat     660 ttcacagaca aaggaaaatt atccaaggac tggataacgg gaaaaacctg gggattaaga     720
ttctatgtgt ctggacatcc aggcgtacag ttcaccattc gcttaaaaat caccaacatg     780
ccagctgtgg cagtaggtcc tgacctcgtc cttgtggaac aaggacctcc tagaacgtcc     840
ctcgctctcc cacctcctct tcccccaagg gaagcgccac cgccatctct ccccgactct     900
aactccacag ccctggcgac tagtgcacaa actcccacgg tgagaaaaac aattgttacc     960
ctaaacactc cgcctccac cacaggcgac agacttttg atcttgtgca ggggccttc    1020 ctaaccttaa atgctaccaa cccagggggcc actgagtctt gctggcttg tttggccatg    1080

```
ggcccccctt attatgaagc aatagcctca tcaggagagg tcgcctactc caccgacctt    1140
gaccggtgcc gctggggac ccaaggaaag ctcaccctca ctgaggtctc aggacacggg    1200
ttgtgcatag gaaaggtgcc ctttacccat cagcatctct gcaatcagac cctatccatc    1260
aattcctccg gagaccatca gtatctgctc ccctccaacc atagctggtg ggcttgcagc    1320
actggcctca ccccttgcct ctccacctca gtttttaatc agactagaga tttctgtatc    1380
caggtccagc tgattcctcg catctattac tatcctgaag aagttttgtt acaggcctat    1440
gacaattctc accccaggac taaaagagag gctgtctcac ttaccctagc tgttttactg    1500
gggttgggaa tcacggcggg aataggtact ggttcaactg ccttaattaa aggacctata    1560
gacctccagc aaggcctgac aagcctccag atcgccatag atgctgacct ccgggccctc    1620
caagactcag tcagcaagtt agaggactca ctgacttccc tgtccgaggt agtgctccaa    1680
aataggagag gccttgactt gctgtttcta aaagaaggtg gcctctgtgc ggccctaaag    1740
gaagagtgct gttttttacat agaccactca ggtgcagtac gggactccat gaaaaaactc    1800
aaagaaaaac tggataaaag acagttagag cgccagaaaa gccaaaactg gtatgaagga    1860
tggttcaata actccccttg gttcactacc ctgctatcaa ccatcgctgg gccctatta    1920 ctcctccttc tgttgctcat cctcgggcca tgcatcatca taagttagt tcaattcatc    1980 aatgatagga taagtgcagt taaaatttaa                                     2010

<210> SEQ ID NO 25
<211> LENGTH: 2013
<212> TYPE: DNA
<213> ORGANISM: Gibbon leukemia virus

<400> SEQUENCE: 25
accatggtcc tgctgcctgg gtctatgctg ctgacttcta acctgcacca cctgcgacac     60
cagatgtctc ccggctcatg gaaacggctg atcatcctgc tgagctgcgt gttcggagga    120
ggaggcacct ccctgcagaa caagaatcct caccagccaa tgaccctgac atggcaggtg    180 ctgtccccaga caggcgacgt ggtgtgggat accaaggcag tgcagccacc ttggacatgg    240
tggcccaccc tgaagcctga cgtgtgcgcc ctggccgcct ccctggagtc ttgggacatc    300
cccggcacag acgtgagcag cagcaagagg gtgagaccac ccgactctga ttatacagcc    360
gcctacaagc agatcacctg gggcgccatc ggctgtagct atcctcgggc cgcacaagg    420 atggccagct ccacctttta cgtgtgccca cgcgacggaa ggaccctgtc tgaggcaagg    480
agatgtggcg gcctggagag cctgtattgc aaggagtggg attgtgagac cacaggcaca    540
ggctactggc tgtctaagtc tagcaaggac ctgatcaccg tgaagtggga tcagaacagc    600
gagtggacac agaagttcca gcagtgccac cagaccggct ggtgtaatcc cctgaagatc    660
gactttacag ataagggcaa gctgtccaag gactggatca ccggcaagac atggggcctg    720
agattctacg tgtctggcca ccctggcgtg cagtttacaa tccggctgaa gatcaccaac    780
atgccagcag tggcagtggg accagacctg gtgctggtgg agcagggacc tccacgcacc    840
tccctggccc tgccccctcc actgcccct agggaggccc cacccctag cctgcccgat    900 tctaacagca cagccctggc cacctccgcc cagaccccta cagtgcgcaa gaccatcgtg    960
acactgaata ccccaccccc taccacaggc acaggctgt tcgatctggt gcagggcgcc    1020
tttctgacac tgaacgccac caatcctggc gcaaccgaga ctgctggct gtgcctggct    1080 atgggcccac cctactatga ggcaatcgcc tcctctggag aggtggcata ttccacagac    1140
ctggatagat gcagatgggg caccagggc aagctgaccc tgacagaggt gtctggccac    1200
```

-continued

```
ggcctgtgca tcggcaaggt gccattcaca caccagcacc tgtgcaacca gaccctgagc    1260
atcaatagct ccggcgacca ccagtacctg ctgccaagca accactcctg gtgggcatgc    1320
tccacaggac tgaccccatg tctgagcacc agcgtgttca accagaccag agacttttgt    1380
atccaggtgc agctgatccc tcggatctac tattacccag aggaggtgct gctgcaggcc    1440
tatgataatt cccacccaag aacaaagagg gaggccgtgt ctctgaccct ggccgtgctg    1500
ctgggactgg gaatcacagc aggaatcggc acaggcagca ccgccctgat caagggacca    1560
atcgacctgc agcagggact gacctccctg cagatcgcca tcgacgccga tctgagagcc    1620
ctgcaggaca gcgtgtccaa gctggaggat tctctgacct ctctgagcga ggtggtgctg    1680
cagaacagga ggggcctgga cctgctgttc ctgaaggagg aggactgtgc gccgccctg     1740 aaggaggagt gctgttttta tatcgaccac tctggcgccg tgcgggatag catgaagaag    1800
ctgaaggaga agctggataa cgccagctg gagaggcaga agagccagaa ttggtacgag     1860
ggctggttca acaattcccc ctggtttacc acactgctgt ctaccatcgc aggacctctg    1920
ttattactgc tgctgctgct gatcctgggc ccatgtatca tcaacaagct ggtgcagttt    1980
atcaacgacc gaatctccgc agtgaaaatc taa                                 2013
```

<210> SEQ ID NO 26
<211> LENGTH: 669
<212> TYPE: PRT
<213> ORGANISM: Gibbon leukemia virus

<400> SEQUENCE: 26

```
Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
        115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220
```

```
Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
            245                 250                 255

Ile Thr Asn Met Pro Ala Val Ala Val Gly Pro Asp Leu Val Leu Val
                260                 265                 270

Glu Gln Gly Pro Pro Arg Thr Ser Leu Ala Leu Pro Pro Pro Leu Pro
            275                 280                 285

Pro Arg Glu Ala Pro Pro Ser Leu Pro Asp Ser Asn Ser Thr Ala
290                 295                 300

Leu Ala Thr Ser Ala Gln Thr Pro Thr Val Arg Lys Thr Ile Val Thr
305                 310                 315                 320

Leu Asn Thr Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
                340                 345                 350

Ser Cys Trp Leu Cys Leu Ala Met Gly Pro Pro Tyr Tyr Glu Ala Ile
            355                 360                 365

Ala Ser Ser Gly Glu Val Ala Tyr Ser Thr Asp Leu Asp Arg Cys Arg
370                 375                 380

Trp Gly Thr Gln Gly Lys Leu Thr Leu Thr Glu Val Ser Gly His Gly
385                 390                 395                 400

Leu Cys Ile Gly Lys Val Pro Phe Thr His Gln His Leu Cys Asn Gln
                405                 410                 415

Thr Leu Ser Ile Asn Ser Ser Gly Asp His Gln Tyr Leu Leu Pro Ser
            420                 425                 430

Asn His Ser Trp Trp Ala Cys Ser Thr Gly Leu Thr Pro Cys Leu Ser
        435                 440                 445

Thr Ser Val Phe Asn Gln Thr Arg Asp Phe Cys Ile Gln Val Gln Leu
    450                 455                 460

Ile Pro Arg Ile Tyr Tyr Tyr Pro Glu Glu Val Leu Leu Gln Ala Tyr
465                 470                 475                 480

Asp Asn Ser His Pro Arg Thr Lys Arg Glu Ala Val Ser Leu Thr Leu
                485                 490                 495

Ala Val Leu Leu Gly Leu Gly Ile Thr Ala Gly Ile Gly Thr Gly Ser
            500                 505                 510

Thr Ala Leu Ile Lys Gly Pro Ile Asp Leu Gln Gln Gly Leu Thr Ser
        515                 520                 525

Leu Gln Ile Ala Ile Asp Ala Asp Leu Arg Ala Leu Gln Asp Ser Val
530                 535                 540

Ser Lys Leu Glu Asp Ser Leu Thr Ser Leu Ser Glu Val Val Leu Gln
545                 550                 555                 560

Asn Arg Arg Gly Leu Asp Leu Leu Phe Leu Lys Glu Gly Gly Leu Cys
                565                 570                 575

Ala Ala Leu Lys Glu Glu Cys Cys Phe Tyr Ile Asp His Ser Gly Ala
            580                 585                 590

Val Arg Asp Ser Met Lys Lys Leu Lys Glu Lys Leu Asp Lys Arg Gln
        595                 600                 605

Leu Glu Arg Gln Lys Ser Gln Asn Trp Tyr Glu Gly Trp Phe Asn Asn
    610                 615                 620

Ser Pro Trp Phe Thr Thr Leu Leu Ser Thr Ile Ala Gly Pro Leu Leu
625                 630                 635                 640

Leu Leu Leu Leu Leu Leu Ile Leu Gly Pro Cys Ile Ile Asn Lys Leu
```

Val Gln Phe Ile Asn Asp Arg Ile Ser Ala Val Lys Ile
         645                 650                 655
                    660                 665

<210> SEQ ID NO 27
<211> LENGTH: 759
<212> TYPE: DNA
<213> ORGANISM: Artificial Sequence
<220> FEATURE:
<223> OTHER INFORMATION: Human-Mouse hybrid

<400> SEQUENCE: 27

```
atgatcgaga cctacaatca gacaagccca cggtccgccg caaccggact gcctatcagc      60
atgaagatct tcatgtacct gctgaccgtg tttctgatca cacagatgat cggctccgcc     120
ctgttcgccg tgtatctgca caggagactg gacaagatcg aggatgagcg caatctgcac     180
gaggacttcg tgtttatgaa gaccatccag cggtgcaaca caggcgagag gagcctgtct     240
ctgctgaatt gtgaggagat caagtcccag ttcgagggct tgtgaaggga tatcatgctg     300
aacaaggagg agacaaagaa ggacgaggat ccacagatcg cagcacacgt ggtgtccgag     360
gcaaactcta atgccgccag cgtgctgcag tgggccaaga agggctacta taccatgaag     420
tctaacctgg tgacactgga gaatggcaag cagctgaccg tgaagaggca gggcctgtac     480
tatatctatg cccaggtgac attctgctct aacagagagg caagtcccca ggcacccttc     540
atcgtgggac tgtggctgaa gcctctagc ggcagcgaga ggatcctgct gaaggccgcc     600
aatacccact cctctagcca gctgtgcgag cagcagtcca tccacctggg aggcgtgttc     660
gagctgcagc ctggagccag cgtgttcgtg aacgtgacag acccatctca ggtgagccac     720
ggcaccggct tcacaagctt tggcctgctg aagctgtga                           759
```

<210> SEQ ID NO 28
<211> LENGTH: 252
<212> TYPE: PRT
<213> ORGANISM: Artificial Sequence
<220> FEATURE:
<223> OTHER INFORMATION: Human-Mouse hybrid

<400> SEQUENCE: 28

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr

| | 145 | | | 150 | | | | 155 | | | | 160 | |

Tyr Ile Tyr Ala Gln Val Thr Phe Cys Ser Asn Arg Glu Ala Ser Ser
                    165                  170                  175

Gln Ala Pro Phe Ile Val Gly Leu Trp Leu Lys Pro Ser Ser Gly Ser
             180                  185                  190

Glu Arg Ile Leu Leu Lys Ala Ala Asn Thr His Ser Ser Ser Gln Leu
        195                  200                  205

Cys Glu Gln Gln Ser Ile His Leu Gly Gly Val Phe Glu Leu Gln Pro
210                  215                  220

Gly Ala Ser Val Phe Val Asn Val Thr Asp Pro Ser Gln Val Ser His
225                  230                  235                  240

Gly Thr Gly Phe Thr Ser Phe Gly Leu Leu Lys Leu
             245                  250

<210> SEQ ID NO 29
<211> LENGTH: 1416
<212> TYPE: DNA
<213> ORGANISM: Homo sapiens

<400> SEQUENCE: 29

```
atgctgccct ttctgagcat gctggtgctg ctggtgcagc tctgggaaa cctgggagcc      60
gagatgaaga gcctgtccca gagatctgtg cctaacacct gcacactggt catgtgcagc     120
cccaccgaga atggactgcc tggaaggac ggaagggatg aaggagggg ccctcggggc      180
gagaagggcg acccaggact gcctggacca atgggactga gcggactgca gggaccaaca     240
ggacctgtgg gaccaaaggg agagaacgga tccgccggag agccaggccc taagggcgag     300
aggggcctgt ctggcccccc tggcctgcca ggcatcccag ccccgccgg caaggagggc      360
ccatccggca gcagggcaa tatcggcccc cagggcaagc tggcccaaa gggcgaggca      420
ggaccaaagg agaagtgggg agcacctggc atgcagggat ccaccggagc aaaggatct     480
acaggaccaa aggcgagcg cggcgcccca ggcgtgcagg gcgcccccgg caatgcagga     540
gcagcaggac cagcaggacc tgcaggccca cagggcgccc tggctctag ggcccaccc      600
ggcctgaagg gcgacagggg agtgcctggc gatagggca tcaagggaga gagcggactg     660
ccagattccg ccgccctgag gcagcagatg gaggccctga gggcaagct gcagaggctg     720
gaggtggcct ctccccacta ccagaaggcc gccctgtttc agacggcca aggagactg      780
gacaagatcg aggatgagcg caacctgcac gaggatttcg tgtttatgaa gaccatccag     840
agatgcaaca caggcgagcg gtctctgagc ctgctgaatt gtgaggagat caagtctcag     900
ttcgagggct tgtgaagga catcatgctg aacaaggagg agaccaagaa ggagaatagc     960
ttcgagatgc agaagggcga tcagaatccc cagatcgcag cacacgtgat cagcgaggca    1020
agctccaaga ccacatccgt gctgcagtgg gccgagaagg gctactatac catgtccaac    1080
aatctggtga cactggagaa cggcaagcag ctgaccgtga agagacaggg cctgtactat    1140
atctatgccc aggtgacatt ctgctctaat cggaggcct ctagccaggc ccctttttatc   1200
gcctctctgt gcctgaagag cccaggcaga ttcgagcgga tcctgctgag ggccgccaac    1260
acccactcct ctgccaagcc atgcggacag cagagcatcc acctgggagg cgtgttcgag    1320
ctgcagccag agcctccgt gttttgtaat gtgacagacc catcccaggt gtctcacgga     1380
accggcttca catccttttgg cctgctgaag ctgtga                             1416
```

<210> SEQ ID NO 30
<211> LENGTH: 471

<212> TYPE: PRT
<213> ORGANISM: Homo sapiens

<400> SEQUENCE: 30

```
Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Pro Gly Leu Pro Gly Ile
            100                 105                 110

Pro Gly Pro Ala Gly Lys Glu Gly Pro Ser Gly Lys Gln Gly Asn Ile
        115                 120                 125

Gly Pro Gln Gly Lys Pro Gly Pro Lys Gly Glu Ala Gly Pro Lys Gly
    130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
        195                 200                 205

Pro Gly Asp Arg Gly Ile Lys Gly Glu Ser Gly Leu Pro Asp Ser Ala
    210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Ile Glu Asp Glu Arg Asn Leu His Glu Asp
            260                 265                 270

Phe Val Phe Met Lys Thr Ile Gln Arg Cys Asn Thr Gly Glu Arg Ser
        275                 280                 285

Leu Ser Leu Leu Asn Cys Glu Glu Ile Lys Ser Gln Phe Glu Gly Phe
    290                 295                 300

Val Lys Asp Ile Met Leu Asn Lys Glu Glu Thr Lys Lys Glu Asn Ser
305                 310                 315                 320

Phe Glu Met Gln Lys Gly Asp Gln Asn Pro Gln Ile Ala Ala His Val
                325                 330                 335

Ile Ser Glu Ala Ser Ser Lys Thr Thr Ser Val Leu Gln Trp Ala Glu
            340                 345                 350

Lys Gly Tyr Tyr Thr Met Ser Asn Asn Leu Val Thr Leu Glu Asn Gly
        355                 360                 365

Lys Gln Leu Thr Val Lys Arg Gln Gly Leu Tyr Tyr Ile Tyr Ala Gln
    370                 375                 380

Val Thr Phe Cys Ser Asn Arg Glu Ala Ser Ser Gln Ala Pro Phe Ile
385                 390                 395                 400
```

```
Ala Ser Leu Cys Leu Lys Ser Pro Gly Arg Phe Glu Arg Ile Leu Leu
            405                 410                 415

Arg Ala Ala Asn Thr His Ser Ser Ala Lys Pro Cys Gly Gln Gln Ser
        420                 425                 430

Ile His Leu Gly Gly Val Phe Glu Leu Gln Pro Gly Ala Ser Val Phe
            435                 440                 445

Val Asn Val Thr Asp Pro Ser Gln Val Ser His Gly Thr Gly Phe Thr
    450                 455                 460

Ser Phe Gly Leu Leu Lys Leu
465                 470

<210> SEQ ID NO 31
<211> LENGTH: 1412
<212> TYPE: DNA
<213> ORGANISM: Mus musculus

<400> SEQUENCE: 31
```

| | | | | | |
|---|---|---|---|---|---|
| atgctgccct | tcctgagcat | gctggtgctg | ctggtgcagc | tctgggcaa | tctgggcgcc | 60 |
| gagatgaagt | ccctgtctca | gaggagcgtg | ccaaacacct | gcacactggt | catgtgctct | 120 |
| ccaaccgaga | atggactgcc | aggaagggac | ggaagagatg | gaaggagggg | accaagggga | 180 |
| gagaagggcg | accctggact | gcctggacca | atgggactgt | ccggactgca | gggaccaaca | 240 |
| ggccctgtgg | gaccaaaggg | agagaatgga | agcgccggag | agccaggacc | taagggagag | 300 |
| aggggcctgt | ccggccccc | tggcctgcct | ggcatcccag | ccccgccgg | caaggagggc | 360 |
| ccttctggca | gcagggcaa | catcggacca | cagggcaagc | ctggaccaaa | gggagaggca | 420 |
| ggaccaaagg | gagaagtggg | agcacccggc | atgcagggca | gcaccggagc | aaagggatcc | 480 |
| accggcccta | agggagagag | aggagcacct | ggagtgcagg | gcgccccagg | caatgcagga | 540 |
| gcagcaggac | cagcaggacc | tgcaggccca | cagggcgccc | caggcagccg | ggcccaccc | 600 |
| ggcctgaagg | gcgacagggg | agtgccaggc | gatagggca | tcaagggaga | gtccggactg | 660 |
| ccagactctg | ccgccctgag | gcagcagatg | gaggccctga | agggcaagct | gcagaggctg | 720 |
| gaggtggcct | tctcccacta | ccagaaggcc | gccctgtttc | cagacggaca | caggagactg | 780 |
| gataaggtgg | aggaggaggt | gaacctgcac | gaggatttcg | tgttcatcaa | gaagctgaag | 840 |
| aggtgcaaca | agggcgaggg | cagcctgtcc | ctgctgaatt | gtgaggagat | gcggcgccag | 900 |
| ttcgaggacc | tggtgaagga | tatcaccctg | aacaaggagg | agaagaagga | gaattctttt | 960 |
| gagatgcaga | gggcgacga | ggatcctcag | atcgcagcac | acgtggtgtc | cgaggcaaac | 1020 |
| tctaatgccg | ccagcgtgct | gcagtgggcc | aagaagggct | actataccat | gaagtctaac | 1080 |
| ctggtcatgc | tggagaatgg | caagcagctg | acagtgaaga | gagagggcct | gtactacgtg | 1140 |
| tacacccagg | tgacattctg | cagcaacaga | gagcccagct | cccagcggcc | ttttatcgtg | 1200 |
| ggcctgtggc | tgaagccctc | tatcggaagc | gagaggatcc | tgctgaaggc | agccaatacc | 1260 |
| cactctagct | cccagctgtg | cgagcagcag | tccgtgcacc | tgggaggcgt | gttcgagctg | 1320 |
| caggcaggag | caagcgtgtt | cgtgaacgga | cagaggccag | ccaggtcatc | cacagagtgg | 1380 |
| gcttctctag | ctttggcctg | ctgaagctgt | ga | | | 1412 |

```
<210> SEQ ID NO 32
<211> LENGTH: 470
<212> TYPE: PRT
<213> ORGANISM: Mus musculus

<400> SEQUENCE: 32
```

```
Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Gly Leu Pro Gly Ile
                100                 105                 110

Pro Gly Pro Ala Gly Lys Glu Gly Pro Ser Gly Lys Gln Gly Asn Ile
            115                 120                 125

Gly Pro Gln Gly Lys Pro Gly Pro Lys Gly Glu Ala Gly Pro Lys Gly
    130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
            195                 200                 205

Pro Gly Asp Arg Gly Ile Lys Gly Glu Ser Gly Leu Pro Asp Ser Ala
    210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Val Glu Glu Val Asn Leu His Glu Asp
    260                 265                 270

Phe Val Phe Ile Lys Lys Leu Lys Arg Cys Asn Lys Gly Glu Gly Ser
    275                 280                 285

Leu Ser Leu Leu Asn Cys Glu Glu Met Arg Arg Gln Phe Glu Asp Leu
    290                 295                 300

Val Lys Asp Ile Thr Leu Asn Lys Glu Glu Lys Glu Asn Ser Phe
305                 310                 315                 320

Glu Met Gln Arg Gly Asp Glu Asp Pro Gln Ile Ala Ala His Val Val
                325                 330                 335

Ser Glu Ala Asn Ser Asn Ala Ala Ser Val Leu Gln Trp Ala Lys Lys
            340                 345                 350

Gly Tyr Tyr Thr Met Lys Ser Asn Leu Val Met Leu Glu Asn Gly Lys
            355                 360                 365

Gln Leu Thr Val Lys Arg Glu Gly Leu Tyr Tyr Val Tyr Thr Gln Val
    370                 375                 380

Thr Phe Cys Ser Asn Arg Glu Pro Ser Ser Gln Arg Pro Phe Ile Val
385                 390                 395                 400

Gly Leu Trp Leu Lys Pro Ser Ile Gly Ser Glu Arg Ile Leu Leu Lys
                405                 410                 415
```

```
Ala Ala Asn Thr His Ser Ser Gln Leu Cys Glu Gln Gln Ser Val
            420                 425                 430
His Leu Gly Gly Val Phe Glu Leu Gln Ala Gly Ala Ser Val Phe Val
                435                 440                 445
Asn Val Thr Glu Ala Ser Gln Val Ile His Arg Val Gly Phe Ser Ser
        450                 455                 460
Phe Gly Leu Leu Lys Leu
465                 470

<210> SEQ ID NO 33
<211> LENGTH: 786
<212> TYPE: DNA
<213> ORGANISM: Homo sapiens

<400> SEQUENCE: 33
atgatcgaaa catacaacca aacttctccc cgatctgcgg ccactggact gcccatcagc      60
atgaaaattt ttatgtattt acttactgtt tttcttatca cccagatgat tgggtcagca     120 cttttttgctg tgtatcttca tagaaggttg gacaagatag aagatgaaag gaatcttcat     180
gaagattttg tattcatgaa aacgatacag agatgcaaca caggagaaag atccttatcc     240
ttactgaact gtgaggagat taaaagccag tttgaaggct tgtgaagga tataatgtta     300 aacaaagagg agacgaagaa agaaaacagc tttgaaatgc aaaaaggtga tcagaatcct     360
caaattgcgg cacatgtcat aagtgaggcc agcagtaaaa caacatctgt gttacagtgg     420
gctgaaaaag gatactacac catgagcaac aacttggtaa ccctggaaaa tgggaaacag     480
ctgaccgtta aaagacaagg actctattat atctatgccc aagtcacctt ctgttccaat     540
cgggaagctt cgagtcaagc tccatttata gccagcctct gcctaaagtc ccccggtaga     600
ttcgagagaa tcttactcag agctgcaaat acccacagtt ccgccaaacc ttgcgggcaa     660
caatccattc acttgggagg agtatttgaa ttgcaaccag gtgcttcggt gtttgtcaat     720
gtgactgatc aagccaagt gagccatggc actggcttca cgtcctttgg cttactcaaa     780
ctctga                                                                786

<210> SEQ ID NO 34
<211> LENGTH: 261
<212> TYPE: PRT
<213> ORGANISM: Homo sapiens

<400> SEQUENCE: 34

Met Ile Glu Thr Tyr Asn Gln Thr Ser Pro Arg Ser Ala Ala Thr Gly
1               5                   10                  15
Leu Pro Ile Ser Met Lys Ile Phe Met Tyr Leu Leu Thr Val Phe Leu
            20                  25                  30
Ile Thr Gln Met Ile Gly Ser Ala Leu Phe Ala Val Tyr Leu His Arg
        35                  40                  45
Arg Leu Asp Lys Ile Glu Asp Glu Arg Asn Leu His Glu Asp Phe Val
    50                  55                  60
Phe Met Lys Thr Ile Gln Arg Cys Asn Thr Gly Glu Arg Ser Leu Ser
65                  70                  75                  80
Leu Leu Asn Cys Glu Glu Ile Lys Ser Gln Phe Glu Gly Phe Val Lys
                85                  90                  95
Asp Ile Met Leu Asn Lys Glu Glu Thr Lys Lys Glu Asn Ser Phe Glu
            100                 105                 110
Met Gln Lys Gly Asp Gln Asn Pro Gln Ile Ala Ala His Val Ile Ser
        115                 120                 125
```

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 35
<211> LENGTH: 783
<212> TYPE: DNA
<213> ORGANISM: Mus musculus

<400> SEQUENCE: 35
atgatagaaa catacagcca accttccccc agatccgtgg caactggact tccagcgagc      60
atgaagattt ttatgtattt acttactgtt ttccttatca cccaaatgat tggatctgtg     120 cttttttgctg tgtatcttca tagaagattg gataaggtcg aagaggaagt aaaccttcat     180
gaagattttg tattcataaa aaagctaaag agatgcaaca aggagaagg atctttatcc     240 ttgctgaact gtgaggagat gagaaggcaa tttgaagacc ttgtcaagga tataacgtta     300
aacaaagaag agaaaaaaga aaacagctttt gaaatgcaaa gaggtgatga ggatcctcaa     360
attgcagcac acgttgtaag cgaagccaac agtaatgcag catccgttct acagtgggcc     420
aagaaaggat attataccat gaaaagcaac ttggtaatgc ttgaaaatgg gaaacagctg     480
acggttaaaa gagaaggact ctattatgtc tacactcaag tcaccttctg ctctaatcgg     540
gagccttcga gtcaacgccc attcatcgtc ggcctctggc tgaagcccag cagtggatct     600
gagagaatct tactcaaggc ggcaaatacc cacagttcct cccagctttg cgagcagcag     660
tctgttcact tgggcggagt gtttgaatta caagctggtg cttctgtgtt tgtcaacgtg     720
actgaagcaa gccaagtgat ccacagagtt ggcttctcat cttttggctt actcaaactc     780
tga                                                                   783

<210> SEQ ID NO 36
<211> LENGTH: 260
<212> TYPE: PRT
<213> ORGANISM: Mus musculus

<400> SEQUENCE: 36

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg

```
            35                  40                  45
Arg Leu Asp Lys Val Glu Glu Val Asn Leu His Glu Asp Phe Val
 50                  55                  60

Phe Ile Lys Lys Leu Lys Arg Cys Asn Lys Gly Gly Ser Leu Ser
 65                  70                  75                  80

Leu Leu Asn Cys Glu Glu Met Arg Arg Gln Phe Glu Asp Leu Val Lys
                 85                  90                  95

Asp Ile Thr Leu Asn Lys Glu Glu Lys Lys Glu Asn Ser Phe Glu Met
                100                 105                 110

Gln Arg Gly Asp Glu Asp Pro Gln Ile Ala Ala His Val Val Ser Glu
                115                 120                 125

Ala Asn Ser Asn Ala Ala Ser Val Leu Gln Trp Ala Lys Lys Gly Tyr
130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
                180                 185                 190

Trp Leu Lys Pro Ser Ser Gly Ser Glu Arg Ile Leu Leu Lys Ala Ala
                195                 200                 205

Asn Thr His Ser Ser Ser Gln Leu Cys Glu Gln Gln Ser Val His Leu
210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
                260

<210> SEQ ID NO 37
<211> LENGTH: 632
<212> TYPE: DNA
<213> ORGANISM: Artificial Sequence
<220> FEATURE:
<223> OTHER INFORMATION: CMV promoter

<400> SEQUENCE: 37
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa tt                                   632

<210> SEQ ID NO 38
<211> LENGTH: 394
```

```
<212> TYPE: DNA
<213> ORGANISM: Artificial Sequence
<220> FEATURE:
<223> OTHER INFORMATION: RSV promoter

<400> SEQUENCE: 38
tgtacgggcc agatatacgc gtatctgagg ggactagggt gtgtttaggc gaaaagcggg     60
gcttcggttg tacgcggtta ggagtccccct caggatatag tagtttcgct tttgcatagg   120 gaggggggaaa tgtagtctta tgcaatacac ttgtagtctt gcaacatggt aacgatgagt   180
tagcaacatg ccttacaagg agagaaaaag caccgtgcat gccgattggt ggaagtaagg    240
tggtacgatc gtgccttatt aggaaggcaa cagacaggtc tgacatggat tggacgaacc    300
actgaattcc gcattgcaga gataattgta tttaagtgcc tagctcgata caataaacgc    360
catttgacca ttcaccacat tggtgtgcac ctcc                                394

<210> SEQ ID NO 39
<211> LENGTH: 188
<212> TYPE: DNA
<213> ORGANISM: Artificial Sequence
<220> FEATURE:
<223> OTHER INFORMATION: BGH polyA

<400> SEQUENCE: 39
ctgtgccttc tagttgccag ccatctgttg tttgcccctc ccccgtgcct tccttgaccc     60
tggaaggtgc cactcccact gtcctttcct aataaaatga ggaaattgca tcgcattgtc    120
tgagtaggtg tcattctatt ctggggggtg gggtggggca ggacagcaag ggggaggatt    180
gggaagac                                                              188

<210> SEQ ID NO 40
<211> LENGTH: 249
<212> TYPE: DNA
<213> ORGANISM: Artificial Sequence
<220> FEATURE:
<223> OTHER INFORMATION: SV40 late polyA

<400> SEQUENCE: 40
gacatgataa gatacattga tgagtttgga caaaccacaa ctagaatgca gtgaaaaaaa     60
tgctttattt gtgaaatttg tgatgctatt gctttatttg tgaaatttgt gatgctattg    120
ctttatttgt aaccattata agctgcaata acaagttaa caacaacaat tgcattcatt     180
ttatgtttca ggttcagggg gaggtgtggg aggttttttta aagcaagtaa aacctctaca    240
aatgtggta                                                             249

<210> SEQ ID NO 41
<211> LENGTH: 99
<212> TYPE: DNA
<213> ORGANISM: Artificial Sequence
<220> FEATURE:
<223> OTHER INFORMATION: Rabbit beta-globulin polyA

<400> SEQUENCE: 41
gacctctggc taataaagga aatttatttt cattgcaata gtgtgttgga attttttgtg     60
tctctcactc ggaaggacat atgggagggc aaatcattt                            99

<210> SEQ ID NO 42
<211> LENGTH: 723
<212> TYPE: DNA
<213> ORGANISM: Artificial Sequence
<220> FEATURE:
```

<223> OTHER INFORMATION: GFP

<400> SEQUENCE: 42

| | | | | | |
|---|---|---|---|---|---|
| accatggtga | gcaagggcga | ggagctgttc | accggggtgg | tgcccatcct | ggtcgagctg | 60 |
| gacggcgacg | taaacggcca | caagttcagc | gtgtccggcg | agggcgaggg | cgatgccacc | 120 |
| tacggcaagc | tgaccctgaa | gttcatctgc | accaccggca | agctgcccgt | gccctggccc | 180 |
| accctcgtga | ccaccctgac | ctacggcgtg | cagtgcttca | gccgctaccc | cgaccacatg | 240 |
| aagcagcacg | acttcttcaa | gtccgccatg | cccgaaggct | acgtccagga | gcgcaccatc | 300 |
| ttcttcaagg | acgacggcaa | ctacaagacc | cgcgccgagg | tgaagttcga | gggcgacacc | 360 |
| ctggtgaacc | gcatcgagct | gaagggcatc | gacttcaagg | aggacggcaa | catcctgggg | 420 |
| cacaagctgg | agtacaacta | caacagccac | aacgtctata | tcatggccga | caagcagaag | 480 |
| aacggcatca | aggtgaactt | caagatccgc | cacaacatcg | aggacggcag | cgtgcagctc | 540 |
| gccgaccact | accagcagaa | cacccccatc | ggcgacggcc | ccgtgctgct | gcccgacaac | 600 |
| cactacctga | gcacccagtc | cgccctgagc | aaagacccca | acgagaagcg | cgatcacatg | 660 |
| gtcctgctgg | agttcgtgac | cgccgccggg | atcactctcg | gcatggacga | gctgtacaag | 720 |
| taa | | | | | | 723 |

<210> SEQ ID NO 43
<211> LENGTH: 454
<212> TYPE: DNA
<213> ORGANISM: Artificial Sequence
<220> FEATURE:
<223> OTHER INFORMATION: MoMuLV LTR

<400> SEQUENCE: 43

| | | | | | |
|---|---|---|---|---|---|
| ttaattaagt | aacgccattt | tgcaaggcat | ggaaaaatac | ataactgaga | atagagaagt | 60 |
| tcagatcaag | gtcaggaaca | gatggaacag | ctgaatatgg | gccaaacagg | atatctgtgg | 120 |
| taagcagttc | ctgccccggc | tcagggccaa | gaacagatgg | aacagctgaa | tatgggccaa | 180 |
| acaggatatc | tgtggtaagc | agttcctgcc | ccggctcagg | ccaagaaca | gatggtcccc | 240 |
| agatgcggtc | cagccctcag | cagtttctag | agaaccatca | gatgtttcca | gggtgcccca | 300 |
| aggacctgaa | atgaccctgt | gccttatttg | aactaaccaa | tcagttcgct | tctcgcttct | 360 |
| gttcgcgcgc | ttctgctccc | cgagctcaat | aaaagagccc | acaacccctc | actcggggcg | 420 |
| ccagtcctcc | gattgactga | gtcgcccgct | taag | | | 454 |

<210> SEQ ID NO 44
<211> LENGTH: 1349
<212> TYPE: DNA
<213> ORGANISM: Artificial Sequence
<220> FEATURE:
<223> OTHER INFORMATION: EF1alpha promoter

<400> SEQUENCE: 44

| | | | | | |
|---|---|---|---|---|---|
| ttaattaaga | gtaattcata | caaaaggact | cgcccctgcc | ttggggaatc | ccagggaccg | 60 |
| tcgttaaact | cccactaacg | tagaacccag | agatcgctgc | gttcccgccc | cctcacccgc | 120 |
| ccgctctcgt | catcactgag | gtggagaaga | gcatgcgtga | ggctccggtg | cccgtcagtg | 180 |
| ggcagagcgc | acatcgccca | cagtccccga | gaagttgggg | ggaggggtcg | gcaattgaac | 240 |
| cggtgcctag | agaaggtggc | gcggggtaaa | ctgggaaagt | gatgtcgtgt | actggctccg | 300 |
| cctttttccc | gagggtgggg | gagaaccgta | tataagtgca | gtagtcgccg | tgaacgttct | 360 |
| ttttcgcaac | gggtttgccg | ccagaacaca | ggtaagtgcc | gtgtgtggtt | cccgcgggcc | 420 |

```
tggcctctttt acgggttatg gcccttgcgt gccttgaatt acttccacgc ccctggctgc    480
agtacgtgat tcttgatccc gagcttcggg ttggaagtgg gtgggagagt tcgaggcctt    540
gcggttaagg agccccttcg cctcgtgctt gagttgaggc ctggcttggg cgctggggcc    600
gccgcgtgcg aatctggtgg caccttcgcg cctgtctcgc tgctttcgat aagtctctag    660
ccatttaaaa ttttgatga cctgctgcga cgctttttt ctggcaagat agtcttgtaa     720
atgcgggcca agatctgcac actggtattt cggttttgg ggccgcgggc ggcgacgggg    780
cccgtgcgtc ccagcgcaca tgttcggcga ggcggggcct cgagcgcgg ccaccgagaa     840 tcggacgggg gtagtctcaa gctggccggc ctgctctggt gcctggcctc cgccgccgt     900 gtatcgcccc gccctgggcg gcaaggctgg cccggtcggc accagttgcg tgagcggaaa    960 gatgccgct tccggccct gctgcaggga gctcaaaatg gaggacgcgg cgctcggag      1020 agcgggcggg tgagtcaccc acacaaagga aagggccttt ccgtcctca gccgtcgctt    1080 catgtgactc cacggagtac cgggcgccgt ccaggcacct cgattagttc tcgagctttt    1140
ggagtacgtc gtctttaggt tgggggagg ggttttatgc gatggagttt ccccacactg    1200
agtgggtgga gactgaagtt aggccagctt ggcacttgat gtaattctcc ttggaatttg    1260
ccctttttga gtttggatct tggttcattc tcaagcctca gacagtggtt caaagttttt    1320
ttcttccatt tcaggtgtcg tgacttaag                                      1349

<210> SEQ ID NO 45
<211> LENGTH: 345
<212> TYPE: DNA
<213> ORGANISM: Artificial Sequence
<220> FEATURE:
<223> OTHER INFORMATION: SV40 enhancer promoter

<400> SEQUENCE: 45
gctgtggaat gtgtgtcagt tagggtgtgg aaagtcccca ggctcccag caggcagaag     60 tatgcaaagc atgcatctca attagtcagc aaccaggtgt ggaaagtccc caggctcccc    120
agcaggcaga agtatgcaaa gcatgcatct caattagtca gcaaccatag tcccgcccct    180
aactccgccc atcccgcccc taactccgcc cagttccgcc cattctccgc cccatggctg    240
actaattttt tttatttatg cagaggccga ggccgcctcg gcctctgagc tattccagaa    300
gtagtgagga ggcttttttg gaggcctagg cttttgcaaa aagct                    345

<210> SEQ ID NO 46
<211> LENGTH: 481
<212> TYPE: DNA
<213> ORGANISM: Artificial Sequence
<220> FEATURE:
<223> OTHER INFORMATION: HGH polyA

<400> SEQUENCE: 46
gacgggtggc atccctgtga cccctcccca gtgcctctcc tggccctgga agttgccact    60
ccagtgccca ccagccttgt cctaataaaa ttaagttgca tcattttgtc tgactaggtg    120
tccttctata atattatggg gtggaggggg gtggtatgga gcaaggggca agttgggaag    180
acaacctgta gggcctgcgg ggtctattgg gaaccaagct ggagtgcagt ggcacaatct    240
```

```
tggctcactg caatctccgc ctcctgggtt caagcgattc tcctgcctca gcctcccgag    300
ttgttgggat tccaggcatg catgaccagg ctcagctaat tttttgttttt ttggtagaga    360 cggggtttca ccatattggc caggctggtc tccaactcct aatctcaggt gatctaccca    420
ccttggcctc ccaaattgct gggattacag gcgtgaacca ctgctccctt ccctgtcctt    480
t                                                                    481
```